(12) United States Patent
Ryan et al.

(10) Patent No.: US 11,413,023 B2
(45) Date of Patent: Aug. 16, 2022

(54) SYSTEM AND METHODS FOR SEALING A CHANNEL IN TISSUE

(71) Applicant: The Provost, Fellows, Scholars and Other Members of Board of Trinity College Dublin, Dublin (IE)

(72) Inventors: Garrett Ryan, Dublin (IE); Colm McGarvey, Dublin (IE)

(73) Assignee: THE PROVOST, FELLOWS, SCHOLARS AND OTHER MEMBERS OF BOARD OF TRINITY COLLEGE DUBLIN, Dublin (IE)

(*) Notice: Subject to any disclaimer, the term of this patent is extended or adjusted under 35 U.S.C. 154(b) by 0 days.

(21) Appl. No.: 16/961,224

(22) PCT Filed: Jan. 10, 2019

(86) PCT No.: PCT/EP2019/050597
§ 371 (c)(1),
(2) Date: Jul. 9, 2020

(87) PCT Pub. No.: WO2019/138019
PCT Pub. Date: Jul. 18, 2019

(65) Prior Publication Data
US 2021/0059654 A1    Mar. 4, 2021

(30) Foreign Application Priority Data
Jan. 10, 2018    (EP) ..................................... 18151100

(51) Int. Cl.
*A61B 17/00*    (2006.01)
*A61B 17/34*    (2006.01)
(Continued)

(52) U.S. Cl.
CPC .... *A61B 17/00491* (2013.01); *A61B 17/0057* (2013.01); *A61B 17/3421* (2013.01);
(Continued)

(58) Field of Classification Search
CPC .......... A61B 17/00491; A61B 17/0057; A61B 17/3417; A61B 17/3421;
(Continued)

(56) References Cited

U.S. PATENT DOCUMENTS 2,697,433 A    12/1954  Zehnder
3,021,842 A    2/1962   Flood
(Continued)

FOREIGN PATENT DOCUMENTS

EP    1958588 A2    8/2008
EP    3150150 A1    4/2017
(Continued)

OTHER PUBLICATIONS

"Burdick et al, Shear-Thinning Hydrogels for Biomedical Applications, Aug. 5, 2011, Soft Matter, 8, 260-272" (Year: 2012).*
(Continued)

*Primary Examiner* — Mohamed G Gabr
(74) *Attorney, Agent, or Firm* — Hamilton, Brook, Smith & Reynolds, P.C.

(57) ABSTRACT

A system for performing a minimally invasive percutaneous procedure comprises a medical device comprising a hydrogel delivery needle (4) with a tip and a hydrogel outlet (6), an injectable, shear-thinning, self-healing viscoelastic hydrogel that exhibits a storage modulus (G') of at least 600 Pa, and a tan δ (G"/G) from 0.1 to 0.6 in dynamic viscoelasticity measured by a rheometer at 1 Hz and 1% strain rate at 25° C. The system may also comprise a coaxial cannula (2) having a lumen configured for receipt of the hydrogel delivery needle (4), wherein the hydrogel delivery needle
(Continued)

comprises an adjustable positioning mechanism (8) configured to limit the advancement depth of the hydrogel delivery needle through the coaxial cannula to a predetermined depth distal to a distal-most end of the coaxial cannula.

18 Claims, 24 Drawing Sheets

(51) Int. Cl.
*A61L 24/00* (2006.01)
*A61L 24/04* (2006.01)
*A61M 5/178* (2006.01)
*A61M 5/46* (2006.01)
*A61B 90/00* (2016.01)

(52) U.S. Cl.
CPC ......... *A61L 24/0031* (2013.01); *A61L 24/043* (2013.01); *A61M 5/178* (2013.01); *A61M 5/46* (2013.01); *A61B 2017/00809* (2013.01); *A61B 2090/062* (2016.02); *A61B 2090/3966* (2016.02); *A61L 2400/06* (2013.01)

(58) Field of Classification Search
CPC .... A61B 2017/00809; A61B 2090/062; A61B 2090/3966; A61L 2400/06; A61L 24/0031; A61L 24/043; A61M 5/178; A61M 5/46

See application file for complete search history.

(56) References Cited

U.S. PATENT DOCUMENTS

| | | | |
|---|---|---|---|
| 3,487,837 A | | 1/1970 | Petersen |
| 5,201,742 A | | 4/1993 | Hasson |
| 5,263,956 A | | 11/1993 | Nobles |
| 5,354,283 A | | 10/1994 | Bark et al. |
| 5,405,330 A | | 4/1995 | Zunitch et al. |
| 5,658,272 A | | 8/1997 | Hasson |
| 5,776,144 A | | 7/1998 | Leysieffer et al. |
| 5,993,463 A | | 11/1999 | Truwit |
| 6,033,401 A | | 3/2000 | Edwards et al. |
| 6,770,070 B1 | * | 8/2004 | Balbierz ................ A61B 10/04 600/566 |
| 7,695,480 B2 | | 4/2010 | Solar et al. |
| 8,747,418 B2 | | 6/2014 | Qureshi et al. |
| 2002/0049451 A1 | | 4/2002 | Parmer et al. |
| 2004/0260312 A1 | | 12/2004 | Magnusson et al. |
| 2008/0006551 A1 | | 1/2008 | Tolley et al. |
| 2009/0306501 A1 | | 12/2009 | Flint |
| 2010/0331882 A1 | | 12/2010 | Bjork et al. |
| 2013/0190809 A1 | | 7/2013 | Vidlund et al. |
| 2013/0267834 A1 | | 10/2013 | McGee |
| 2014/0276559 A1 | | 9/2014 | Page |
| 2016/0089180 A1 | | 3/2016 | Entabi |
| 2016/0120706 A1 | | 5/2016 | Collinson et al. |
| 2016/0317621 A1 | * | 11/2016 | Bright ................ A61K 31/19 |
| 2021/0068917 A1 | | 3/2021 | Ryan et al. |

FOREIGN PATENT DOCUMENTS

| | | |
|---|---|---|
| WO | 94/04067 A1 | 3/1994 |
| WO | 2014140608 A1 | 9/2014 |
| WO | 2016/186937 A1 | 11/2016 |
| WO | 2019/138019 A2 | 7/2019 |
| WO | 2019/180154 A1 | 9/2019 |

OTHER PUBLICATIONS

Datta et al., "Bioprinting for vascular and vascularized tissue biofabrication," Acta Biomaterialia, vol. 51, Mar. 15, 2017, pp. 1-20.

Guvendiren et al., "Shear-thinning hydrogels for biomedical applications," Journal of Soft Matter, Issue 2, 2012, pp. 1-13.

Tseng et al., "Glucose-sensitive self-healing hydrogel as sacrificial materials to fabricate vascularized constructs," Biomaterials, vol. 133, Jul. 2017, pp. 20-28.

International Preliminary Report on Patentability for International Application No. PCT/EP2019/050597, entitled "System and Methods For Sealing a Channel In Tissue," dated Jan. 20, 2020.

International Search Report for International Application No. PCT/EP2019/050597, entitled "System and Methods For Sealing a Channel In Tissue," dated Sep. 27, 2019.

RAD-GUIDE™ Needle Guide for CT & Fluoroscopy, Retrieved from Internet at: http://civco.com/mmi/ultrasound/computed-tomography/needle-guide/radguide-610-1187.htm; Retrieved from Internet on: Oct. 30, 2020, 4 pages.

Simplify Needle Holder Brochure, Copyright 2014, 2 pages.

\* cited by examiner

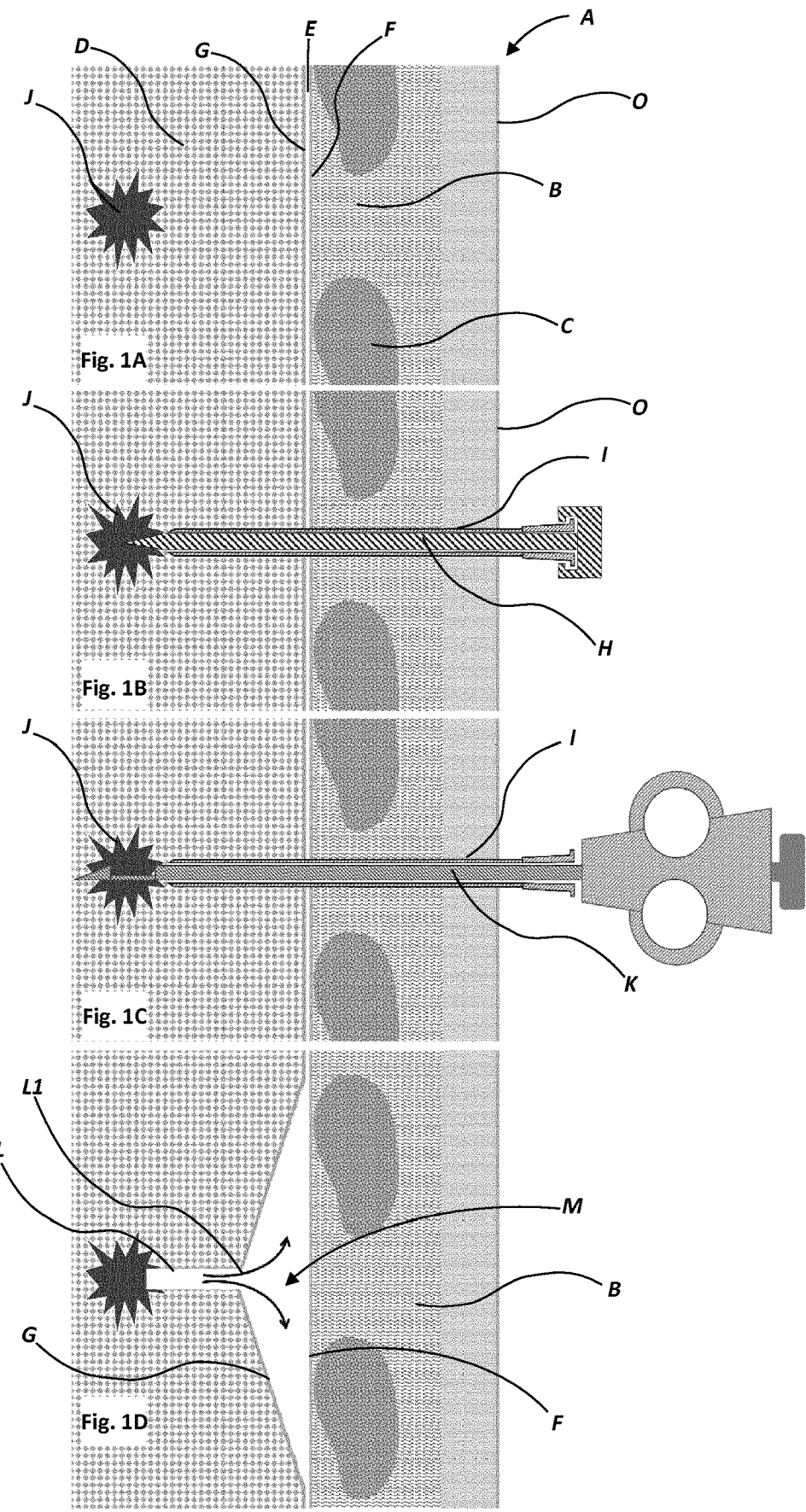

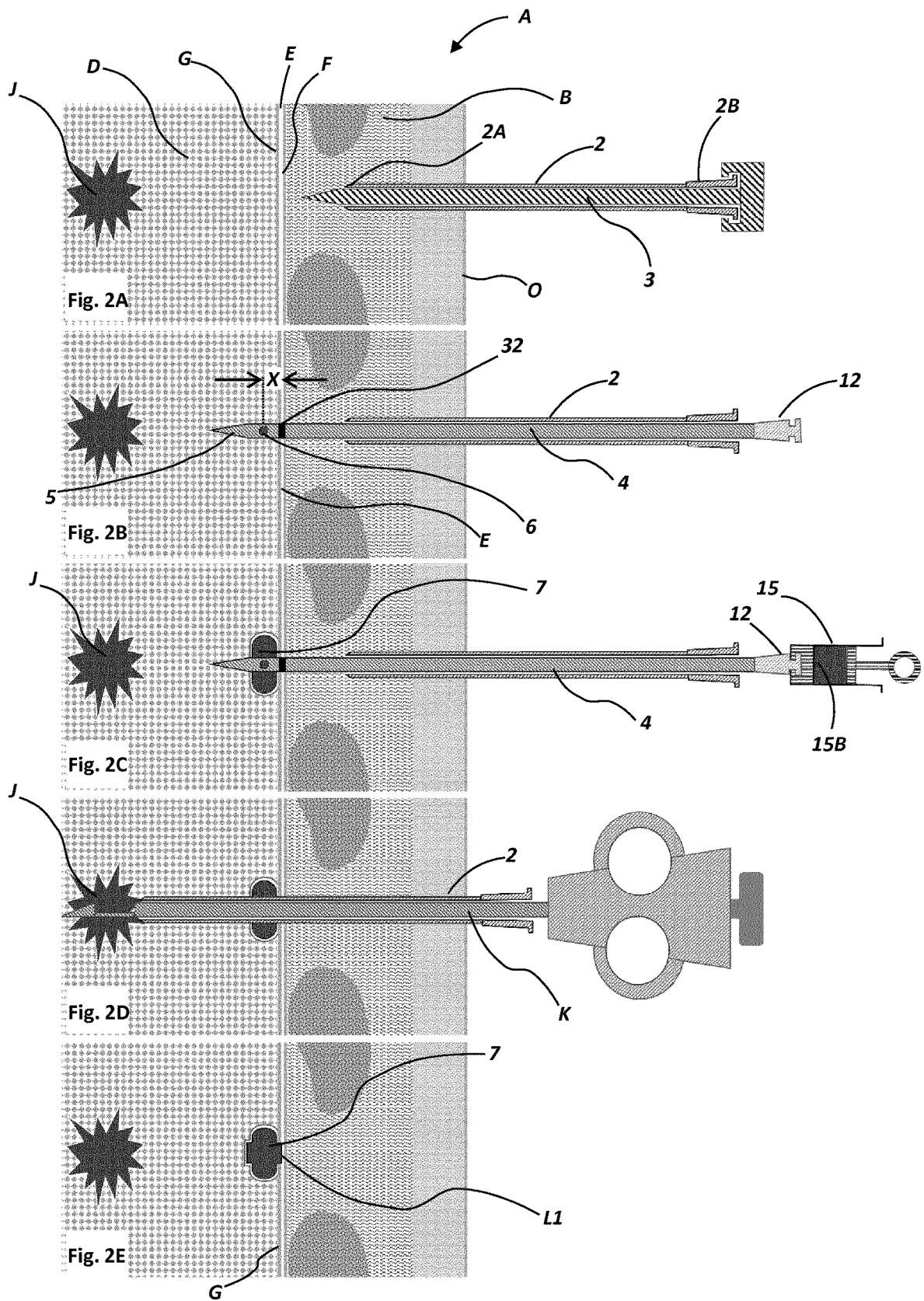

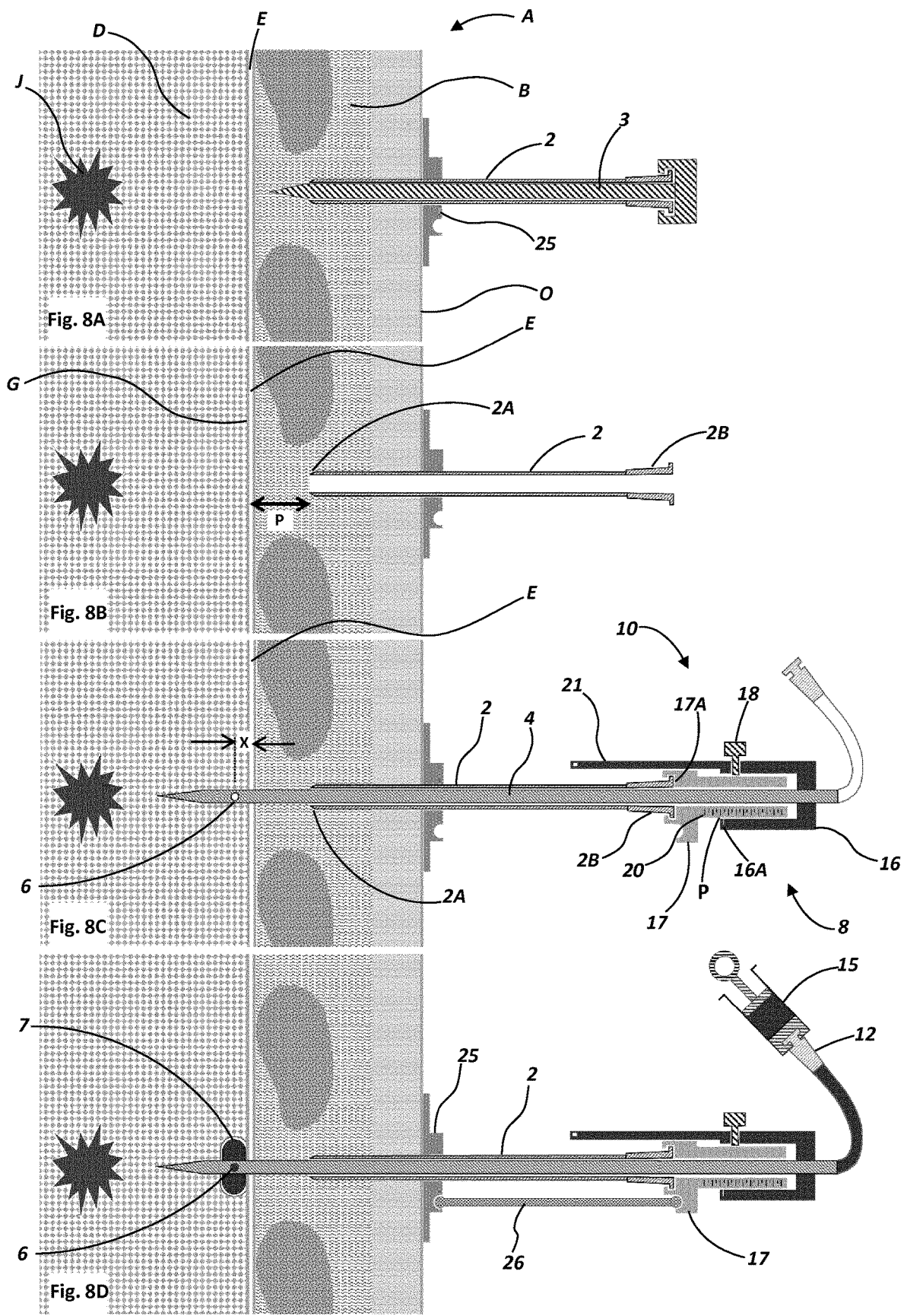

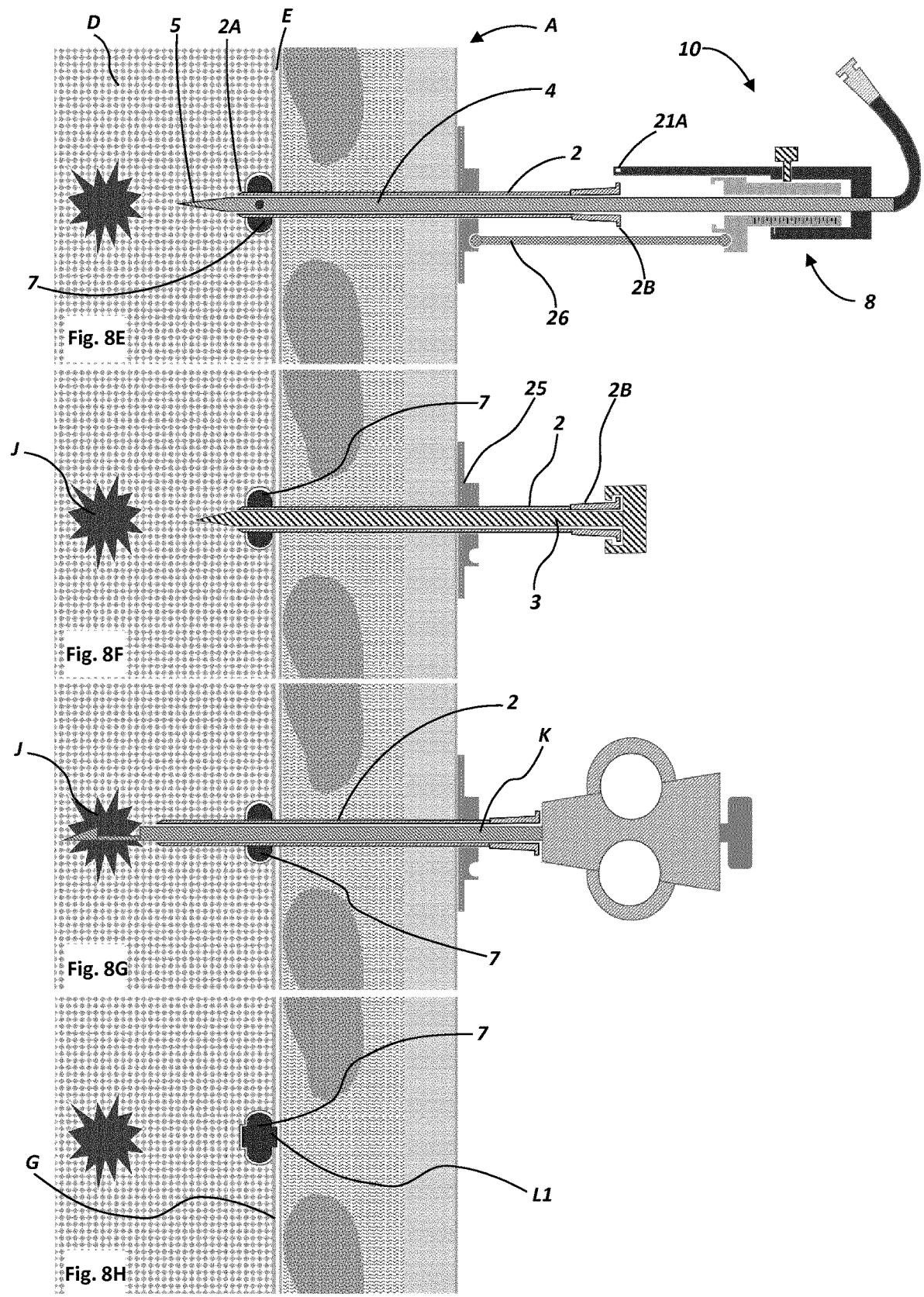

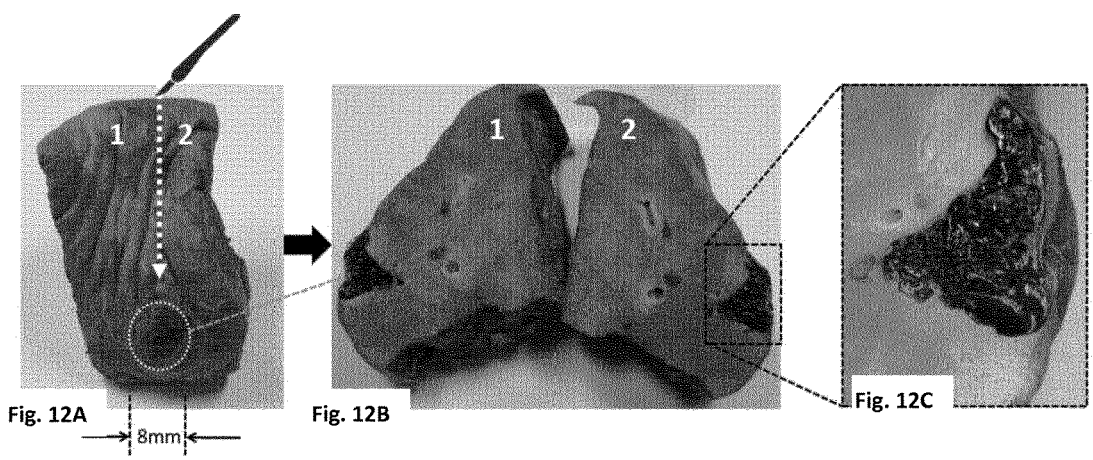
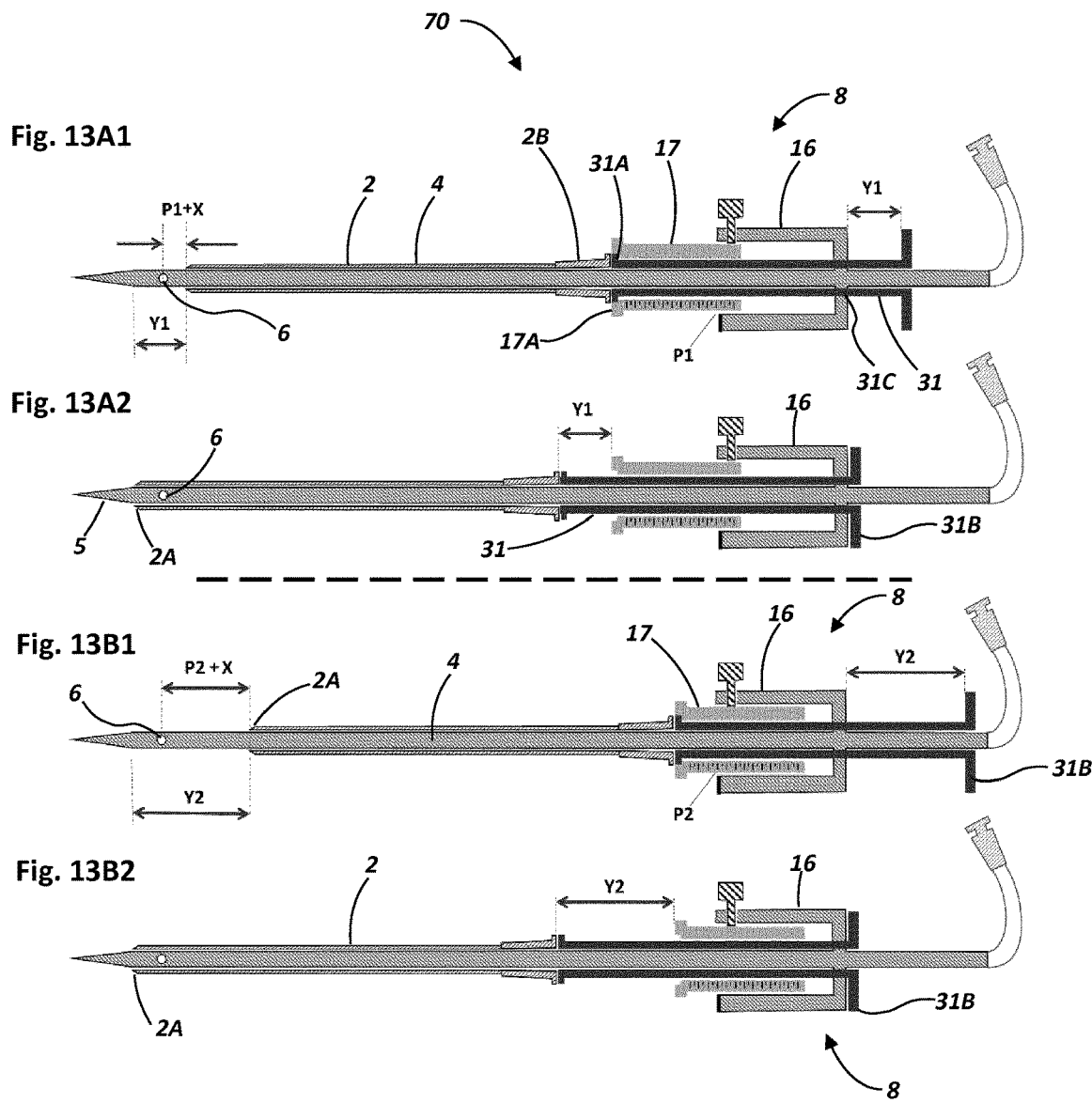

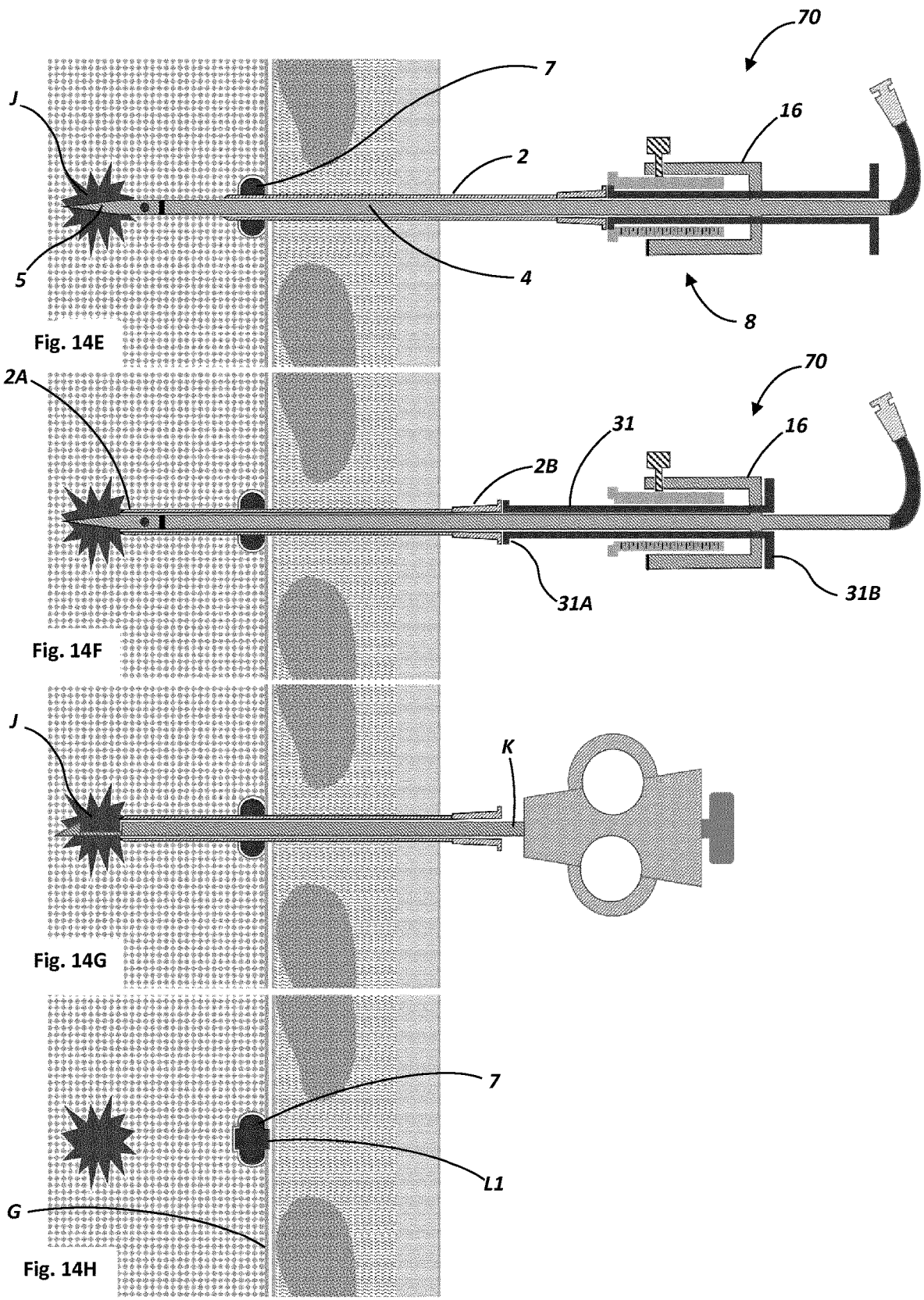

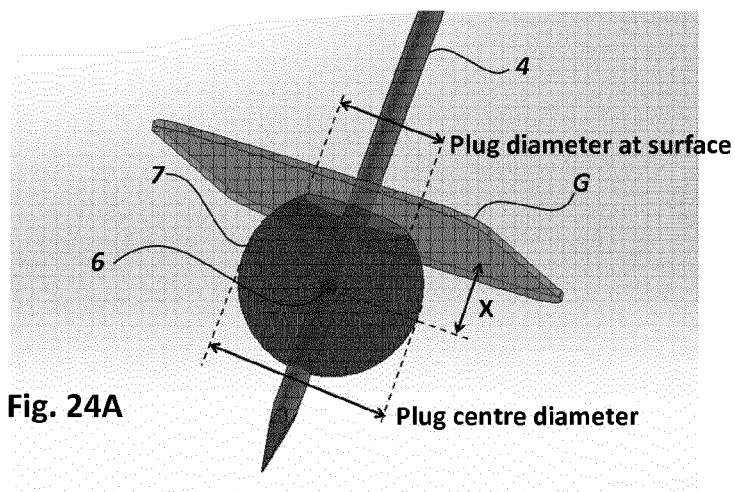
Fig. 24A
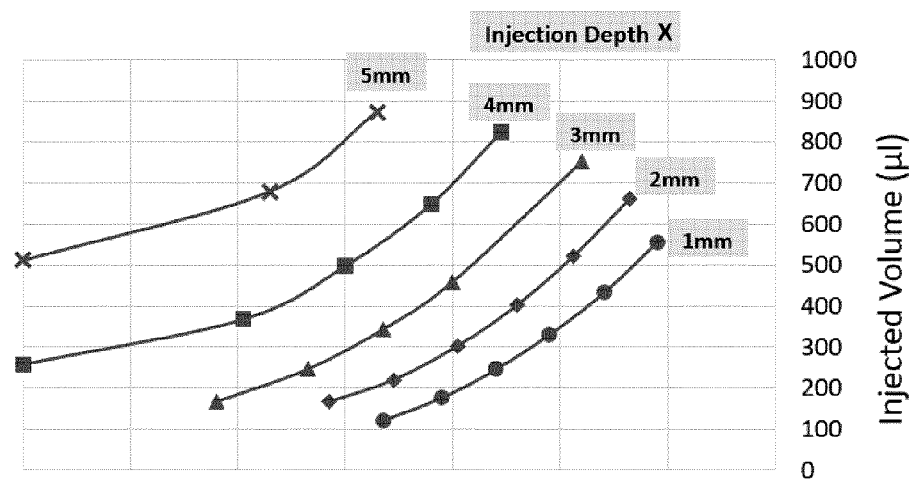
Fig. 24B  Plug diameter at surface of lung (mm)
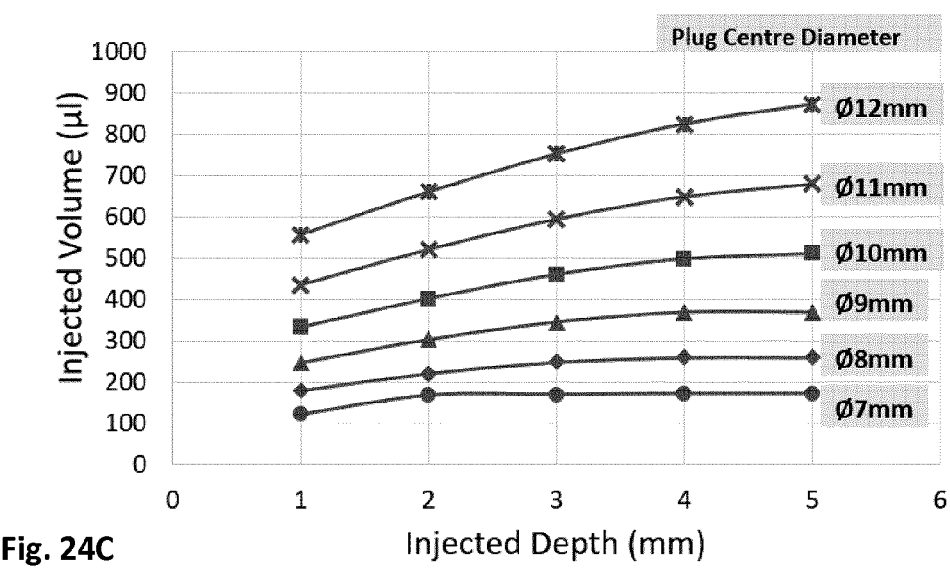
Fig. 24C  Injected Depth (mm)

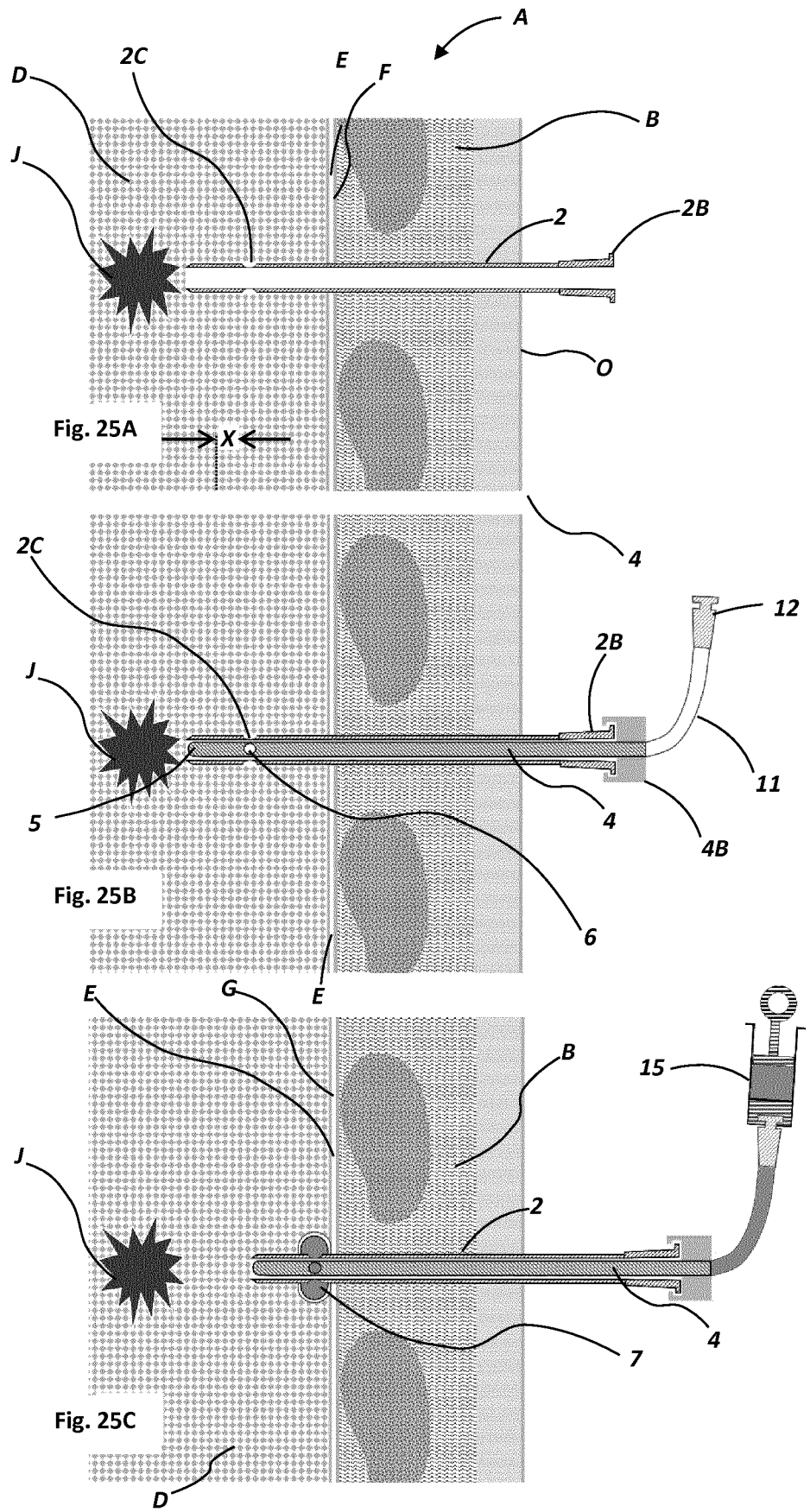

SYSTEM AND METHODS FOR SEALING A CHANNEL IN TISSUE

This application is the U.S. National Stage of International Application No. PCT/EP2019/050597, filed Jan. 10, 2019, which designates the U.S., published in English, and claims priority under 35 U.S.C. § 119 or 365(c) to European Application No. 18151100.7, filed Jan. 10, 2018. The entire teachings of the above applications are incorporated herein by reference.

FIELD OF THE INVENTION

The present invention relates to a system and medical device for safely performing minimally invasive percutaneous procedures. More specifically, it relates to a system and medical device to access internal organs, tissues and cavities without the risk of fluid and/or gas loss. In particular, it provides devices and methods of using these devices to prevent or reduce the risk of pneumothorax or haemothorax during procedures requiring transthoracic needle access. Also contemplated are methods of delivering a tissue apposing viscoelastic hydrogel plug to a target depth in a body organ, tissue or space.

BACKGROUND TO THE INVENTION

A number of surgical procedures require puncturing an instrument through the body to gain access to a target treatment region, such as puncturing the thoracic wall to gain access to the thoracic cavity. The most common example is transthoracic needle lung biopsy where a special needle is used to obtain a sample of tissue from a suspected cancerous tissue mass. This procedure, which is presented schematically in FIGS. 1A-1D (Prior art), is typically carried out by an interventional radiologist using CT (computed tomography) guidance. When the biopsy needle punctures the outer surface of the lung air can escape between the lung and the thoracic wall into a space known as the pleural cavity. The air gradually pushes the lung away from the thoracic wall causing the lung to collapse, a complication known as pneumothorax. If the pneumothorax is large, it can lead to severe pain and distress for the patient. An unresolved pneumothorax can lead to the patient being admitted to hospital for treatment and monitoring and often requires the surgical insertion of a chest drain to withdraw the air in the pleural cavity. Pneumothorax can result in considerable pain and morbidity to the patient, increased anxiety and stress to the attending clinician, and unnecessary and substantial costs to the hospital. Approximately 33% of patients undergoing a transthoracic lung biopsy procedure will develop a pneumothorax and approximately 1 in 3 of these patients will require a chest drain.

Methods to prevent pneumothorax are of great interest because of the concomitant morbidity and hospital expenditures. Numerous attempts have been described in scientific literature and have focussed on plugging the biopsy needle tract with an adhesive or plug as the biopsy needle is being withdrawn. A number of different substances have been injected with this purpose including gelatine sponge slurry, fibrin adhesive, autologous blood, supernatant serum and autologous blood mixture, and collagen foam. These efforts have proven ineffective and have not been widely adopted. Their lack of efficacy may be as a result of the physical properties of the substances injected and the lack of control over their injected location. Additional references which may be suitable for lung sealing are outlined in U.S. Pat. No. 6,592,608B2 and U.S. Pat. No. 6,790,185B1. This technology is commercially available as the Biosentry™ device from Surgical Specialties Corp (MA, USA www.biosentry-system.com). Other publications relevant to lung and tissue sealing include US2016120528A, US2006025815A, US2013338636A, US2006009801A, U.S. Pat. No. 6,770,070B, US2017232138A, US2002032463A, and US2009136589A.

There is a need in the art to provide a medical device, system and method which helps overcome at least one of the above-referenced problems. These challenges will be addressed by the devices, systems and methods disclosed herein.

SUMMARY OF THE INVENTION

The present invention provides a device and methods for sealing a channel in tissue created during a minimally invasive procedure including minimally invasive percutaneous needle access and keyhole surgery. The invention may provide a device and methods for sealing a channel in tissue during procedures requiring percutaneous needle access of body tissues for diagnosis or treatment. The present invention may address the need for a device and method for reducing the risk of fluid and/or gas leak during procedures requiring percutaneous needle access, including needle biopsy, tissue localisation, fiducial marker placement and ablation procedures including microwave, radiofrequency and cryo-ablation, Particular organs of interest prone to fluid and air leak include the lung, the liver and the kidney. The present invention may address the need for a device and method for reducing the risk of bleeding during liver and kidney access for diagnosis and/or treatment. The present invention may address the need for preventing or reducing the risk of pneumothorax and haemothorax during transthoracic needle access procedures.

Optionally in any aspect, the methods involve delivering an injectable viscoelastic shear-thinning hydrogel to a target location in the lung tissue just distal of the visceral pleura. The physical properties of the viscoelastic hydrogel prevent it from infiltrating the lung tissue and instead the hydrogel pushes the tissue away from the delivery needle, forming a closed annular sealing plug which embraces the delivery needle close to or abutting the visceral pleura within the lung. The hydrogel plug is generally annular when delivered but can have other shapes, depending on the shape, number and positioning of the hydrogel outlets on the needle. The use of a hydrogel outlet on the side of the needle is desirable for achieving the annular sealing plug. Shear thinning viscoelastic hydrogels have been found to be ideal for this purpose when they exhibit the required stiffness after needle delivery to avoid tissue infiltration. A coaxial cannula may then be advanced along the delivery needle and through the sealing plug so that the sealing plug forms an airtight seal against the coaxial cannula. A lung biopsy needle may then be passed through the coaxial cannula and a biopsy taken of a suspected lesion without any leakage of air from the lung. Upon withdrawal of the coaxial cannula from the lung, the viscoelasticity of the sealing plug causes it to quickly fill the tract left by withdrawal of the cannula and press against the visceral pleura sealing the hole in the pleura.

According to a first aspect of the present invention, there is provided a system for sealing a channel in tissue (for example a channel created during a minimally invasive percutaneous procedure) comprising:

a medical device comprising a hydrogel delivery needle (4) with a tip (5) (generally a piercing tip) and a hydrogel outlet (6), and
an injectable viscoelastic hydrogel.

In one embodiment, the viscoelastic hydrogel exhibits a storage modulus (G') of at least 400 Pa in dynamic viscoelasticity measured by a rheometer at 1 Hz and 1% strain rate at 25° C.

In one embodiment, the viscoelastic hydrogel exhibits a tan δ (G"/G') from 0.1 to 0.8 in dynamic viscoelasticity measured by a rheometer at 1 Hz and 1% strain rate at 25° C.

In one embodiment, the viscoelastic hydrogel is configured to exhibit an in-vivo residence time of at least 1, 2 or 3 weeks. This enables the gel to persist in tissue, while the tissue needle tract in the tissue heals. Generally, one week is sufficient, but at least two weeks in-vivo residence time is preferred. Hydrogels formed from, or comprising, cross-linked polymers help with in-vivo residence time. For example, by creating a composite hydrogel containing 4-5% non-crosslinked hyaluronic acid and crosslinked gelatin particles (crosslinked by dehyrothermal treatment) an in-vivo residence time of at least two weeks in a lung needle biopsy tract was achieved.

The injectable viscoelastic hydrogel (hereafter "viscoelastic hydrogel" or "hydrogel" or "gel") is generally a tissue apposing hydrogel of sufficient properties that limits its infiltration of tissue so that it pushes the tissue away. In this way the hydrogel can create its own discrete space inside a tissue or organ. To achieve this the properties must be present on entering the target injection site. Typically, the viscoelastic hydrogel exhibits a storage modulus (G') of at least 400 Pa (e.g. 800-6000 Pa), and a tan δ (G"/G') from 0.1 to 0.8 in dynamic viscoelasticity measured by a rheometer at 1 Hz and 1% strain rate at 25° C.

For improved tissue opposing properties and to form a uniform plug surrounding the needle, it is also preferable that the viscoelastic hydrogel portrays an axial compressive stiffness of equal to or greater than lung parenchymal tissue, as measured using an axial compression testing machine, for example by using a Zwick universal testing machine with a 5N load cell at a strain rate of 3 mm/min. The viscoelastic hydrogel should preferably have a compressive modulus of greater than 200 Pa, preferably greater than 400 Pa, and more preferably greater than 800 Pa.

Optionally in any embodiment, the injectable viscoelastic hydrogel is a shear thinning gel. For example, the viscoelastic hydrogel may be configured to have a low viscosity under higher shear stress or shear rates (i.e. during injection through a needle), and a higher viscosity (under lower shear stresses or shear rates) after removal of shear stress (i.e. once delivered to a target location in the body. This enables these materials to create a singular hydrogel plug at the site of delivery. Materials which possess these properties are outlined in the review articles 'Shear-thinning hydrogels for biomedical applications', Soft Matter, (2012) 8, 260, 'Injectable matrices and scaffolds for drug delivery in tissue engineering' Adv Drug Deliv Rev (2007) 59, 263-272, and 'Recent development and biomedical applications of self-healing hydrogels' Expert Opin Drug Deliv (2017) 23: 1-15. Typically, the shear thinning viscoelastic hydrogel exhibits a storage modulus (G') of less than 200 Pa, preferably less than 100 Pa in dynamic viscoelasticity at a frequency of 1 Hz and 100% strain.

Optionally, in any embodiment, the hydrogel is self-healing. This refers to the hydrogel's ability to spontaneously form new bonds between molecules when old bonds are broken within the material.

Optionally in any embodiment, the viscoelastic hydrogel comprises about 2-6% hydrogel forming polymer (w/v). This concentration has been found to be ideal to allow injectability through a lung needle and provide tissue apposition properties, especially when the polymer is hyaluronan.

Optionally in any embodiment, the hydrogel forming polymer is a glycosaminoglycan. Optionally in any embodiment the glycosaminoglycan is a hyaluronan or a salt thereof.

Optionally in any embodiment, the hyaluronan is a high molecular weight hyaluronan with a molecular weight in excess of 1000 kDa (1 MDa).

Optionally in any embodiment, the hydrogel is not cross-linked.

Optionally in any embodiment, the hydrogel is cross-linked.

Optionally in any embodiment, the viscoelastic hydrogel is a colloidal hydrogel. Optionally in any embodiment, the colloidal hydrogel is formed by hydrating biocompatible polymer particles which are preferably insoluble in biological fluid. Optionally in any embodiment, the degradation period of the polymer particles is preferably less than 1 year, more preferably less than 6 months, and more preferably less than 2 months. Optionally in any embodiment, the colloidal hydrogel is comprised of a polymer of biological origin, for example gelatin, collagen, fibrin or hyaluronic acid. Optionally in any embodiment, the polymer is crosslinked. Optionally in any embodiment, the colloidal hydrogel comprises about 0.2-30%, 15-28%, or 20-27% hydrogel forming polymer (w/v). Optionally in any embodiment, the colloidal hydrogel exhibits a storage modulus (G') of greater than 400 Pa, more preferably greater than 800 Pa, more preferably greater than 1000 Pa in dynamic viscoelasticity measured by a rheometer at 1 Hz and 1% strain rate at 25° C.

Optionally in any embodiment, the viscoelastic hydrogel is a multi-phase, for example a biphasic hydrogel, comprised of a colloidal hydrogel dispersed in a continuous phase hydrogel. Optionally in any embodiment, the continuous phase hydrogel may be formed by a hyaluronan hydrogel, and may be present at a concentration of 1-6%, preferably 2-5%. Optionally in any embodiment the hyaluronan hydrogel may be non-crosslinked or lightly crosslinked. Optionally in any embodiment, the colloidal hydrogel may be present at concentrations of 0.2 to 30%, 8 to 20%, 8 to 15%, 8 to 12%, or about 10% hydrogel forming polymer (w/v). Optionally in any embodiment, the colloidal hydrogel is formed from hydrated polymer particles of <100 μm in average particle size (for example 5-99, 20-80, or 30-80 microns. Optionally in any embodiment the colloidal hydrogel is insoluble in aqueous solution. Optionally in any embodiment the colloidal hydrogel is formed from cross-linked polymer particles. Optionally in any embodiment, the colloidal hydrogel is a gelatin hydrogel comprising dehydrothermally (DHT) crosslinked gelatin powders having an average particle size (D50) of about 10-100, 20-50 or 30-40 microns. Optionally in any embodiment, the biphasic hydrogel exhibits a storage modulus (G') of greater than 400 Pa, more preferably greater than 800 Pa, more preferably greater than 1000 Pa, and a tan δ (G"/G') from 0.1 to 0.6 in dynamic viscoelasticity measured by a rheometer at 1 Hz and 1% strain rate at 25° C. Optionally in any embodiment, the biphasic hydrogel portrays an axial compressive stiffness of equal to or greater than lung parenchymal tissue, as measured using an axial compression testing machine Optionally in any embodiment, the viscoelastic hydrogel is de-aerated which means it has been removed of air and/or gas or in other words de-gassed.

Optionally in any embodiment, the hydrogel comprises a therapeutic agent.

Optionally in any embodiment, the hydrogel is biodegradable.

Optionally in any embodiment, the hydrogel is comprised of 2-6%, preferably 3-5% high molecular weight hyaluronan (w/v). Optionally in any embodiment, the hyaluronan hydrogel may be combined with 0.2 to 30% colloidal hydrogel to form a biphasic hydrogel. Optionally in any embodiment, the colloidal hydrogel may be comprised of hydrogel forming polymer particles. Optionally in any embodiment, the hydrogel forming polymer particles are gelatin particles, collagen particles or hyaluronan particles.

Optionally in any embodiment, the hydrogel described herein may be provided in separate components, for example in multiple syringes and the means can be provided to allow mixing of the components prior to injection through the syringe.

Optionally in any embodiment, the system and methods described herein include an initial step of providing the viscoelastic hydrogel as a dehydrated or semi-dehydrated powder, and reconstitution of the powder in a suitable fluid to form the viscoelastic hydrogel.

Optionally in any embodiment, the viscoelastic hydrogel is a microporous hydrogel which can be described as hydrogels with interconnected pores that can mechanically collapse and recover reversibly. When the hydrogel is delivered via injection with a needle and syringe, water is squeezed out from the pores, which causes the hydrogel to collapse, allowing it to pass through the needle. Once the hydrogel has left the needle and the mechanical constraint imposed by the needle walls is removed, the hydrogel can recover its original shape almost immediately in the body. These hydrogels generally behave like a foam and can be reversibly compressed at up to 90% strain without any permanent damage to the network.

Optionally in any embodiment, the viscoelastic hydrogel is provided in a syringe configured for fluidic connection to a proximal end of the hydrogel delivery needle.

Optionally in any embodiment, the syringe comprises 200 μL to 5000 μL of viscoelastic hydrogel, 200 μL to 2000 μL of viscoelastic hydrogel, or 200 μL to 1000 μL of viscoelastic hydrogel.

Optionally in any embodiment, the hydrogel delivery needle diameter can range from 10-24 gauge, preferably from 16-20 gauge. This is the typical needle size range for lung diagnostic procedures. Larger delivery needles (10-16 gauge) may be employed for other procedures including therapeutic procedures such as lung, live and kidney ablation. Smaller needles greater than 20 gauge or larger than 10 gauge may be used for other medical procedures.

Optionally in any embodiment, the hydrogel outlet is spaced proximal to the piercing tip of the needle. The position of the hydrogel outlet on a side of the needle enables formation of a closed annular sealing plug around the needle, and the viscoelastic properties of the hydrogel allow the annular sealing plug to re-shape upon removal of the device whereby the hole in the middle of the sealing plug is filled in. Optionally in any embodiment, the hydrogel outlet is spaced from preferably 1 to 15 mm or more preferably 3-8 mm, from a piercing tip of the needle.

Optionally in any embodiment, the hydrogel delivery needle comprises a plurality of hydrogel outlets disposed on a side of the needle. The hydrogel outlets may be disposed in a radial fashion around the circumference of the needle. The hydrogel outlets may be circular in profile, in which case their size can range from 0.3-1.5 mm in diameter depending on the diameter of the hydrogel delivery needle. The hydrogel outlets may also take non-circular and elongated profiles.

Optionally in any embodiment, the hydrogel outlet consists of a radiolucent region on the delivery needle where sufficient material has been removed through cutting or erosion process to provide a contrast in radiopacity between the delivery needle and the hydrogel outlet.

Optionally in any embodiment, the coaxial cannula consists of an aperture proximal to its distal tip. This aperture may form a radiolucent region on the coaxial cannula by removing sufficient material about the circumference of the cannula.

Optionally in any embodiment, radiolucent regions of both the delivery needle and coaxial cannula are aligned when the delivery needle and cannula are engaged. This will provide a marking function about this radiolucent region during radiographic guidance and allows the viscoelastic hydrogel to be injected at this location.

Optionally in any embodiment, the hydrogel outlet and coaxial cannula aperture may be created using a laser cut profile or pattern which removes a portion of material from the delivery needle wall to create a pathway through which the hydrogel material can flow to the intended target. Removal of a significant amount of material will provide radiolucency to this portion of the device and will provide visual feedback on the position of the hydrogel outlet under CT guidance or other imaging modality. The radiolucency (less radiopaque) is achieved by removal of a significant amount of material from the needle walls using the laser cut pattern without affecting the structural integrity of the needle. Laser cut profiles comprising circumferential triangles and similar structures to those employed in coronary stents can be employed to maintain structural stability. Alternative material eroding technology may also be employed to create the cut pattern.

Optionally in any embodiment, the medical device comprises an adjustable positioning mechanism configured to limit the advancement depth of the hydrogel delivery needle through the coaxial cannula as indicated by a measurement scale forming part of the medical device, and typically forming part of the positioning mechanism.

Optionally in any embodiment, the positioning mechanism comprises a fixed housing attached to the hydrogel delivery needle, a movable hub mounted to the needle for axial movement along the hydrogel delivery needle relative to the fixed housing and having a distal-most face configured to abut a proximal face of the coaxial cannula luer lock.

Optionally in any embodiment, the graduation scale is provided with the adjustable positioning mechanism and is configured to indicate an injection depth P of the hydrogel outlet, and whereby the hydrogel outlet is positioned a distance P+X distal to the distal-most tip of the coaxial cannula when the distal-most face of the positioning mechanism fully abuts the proximal face of the coaxial cannula.

Optionally in any embodiment, the positioning mechanism comprises a cannula depth guide configured to indicate an insertion depth of the coaxial cannula relative to the delivery needle at which insertion depth the distal-most end of the cannula is advanced over the delivery needle by a distance Y to cover the hydrogel outlet, wherein the positioning mechanism is configured such that adjustment of the positioning mechanism to define a predetermined insertion depth of the hydrogel outlet P+X proportionally adjusts the predetermined cannula insertion depth Y indicated by the cannula depth guide.

Optionally in any embodiment, the cannula depth guide comprises an arm that is axially coupled to the fixed housing of the positioning mechanism for movement therewith and that extends distally of the movable hub.

Optionally in any embodiment, a visible mark is provided on the delivery needle proximally to the piercing tip, where the distance between the visible mark and the tip (distance denoted as H) is equal to the length of the coaxial cannula (length of coaxial cannula=H). This visible mark may be used to indicate when the distal end of the coaxial cannula is adjacent to the piercing tip when the delivery needle is inserted through the lumen of the coaxial cannula.

Optionally in any embodiment, the system further comprises a core needle with penetrating distal tip configured for insertion through the inner lumen of the coaxial cannula and attachment to the coaxial cannula luer lock.

Optionally in any embodiment, the system further comprises a syringe configured for fluidic connection to the hydrogel delivery needle, and in which the viscoelastic hydrogel is provided in the syringe.

According to an aspect of the present invention, there is provided a medical device suitable for delivering a substance to a target location within tissue comprising a coaxial cannula having a lumen and a hydrogel delivery needle configured for advancement through the lumen of the coaxial cannula, the hydrogel delivery needle comprising a distal piercing tip, a hydrogel outlet, and a positioning mechanism associated with the hydrogel delivery needle that is axially adjustable to define a predetermined insertion depth of the needle outlet relative to distal most end of the coaxial cannula.

Optionally in any embodiment, the positioning mechanism may be retro-fitted to the hydrogel delivery needle.

Optionally in any embodiment, the medical device is provided with a measurement device including a measurement scale configured to provide a means of determining the insertion depth of the needle outlet relative to the distal-most end of the coaxial cannula. The measurement device can include a ruler, scale, callipers, micrometre or other mechanical or digital measurement mechanism.

Optionally in any embodiment, the positioning mechanism comprises a fixed housing attached to the hydrogel delivery needle, a movable hub mounted to the fixed housing for axial movement along the axis of the needle and fixed housing and having a distal-most end configured to abut a proximal end of the coaxial cannula, wherein the fixed housing is configured to cooperate with the movable hub for relative axial movement to define the predetermined needle adjustment depth.

Optionally in any embodiment, the fixed housing and/or movable hub comprise a measurement scale and graduations configured to allow the user adjust the predetermined needle insertion depth. A micrometer scale or Vernier scale may be employed with the positioning mechanism with one element of the scale provided to the fixed housing and the second element of the scale provided to the movable hub.

Optionally in any embodiment, the fixed housing and movable hub are coaxially coupled together, typically in a threaded engagement.

Optionally in any embodiment, the positioning mechanism includes a locking screw (mechanism) operable to lock the fixed housing and movable hub together.

Optionally in any embodiment, the positioning mechanism is associated with a proximal end of the delivery needle and is axially adjustable to define a predetermined insertion depth of the delivery needle outlet relative to the coaxial cannula at which insertion depth the hydrogel outlet is spaced a predetermined distance from a distal-most end of the coaxial cannula, wherein the positioning mechanism comprises a cannula depth guide configured to indicate an insertion depth of the cannula relative to the needle at which insertion depth the distal-most end of the cannula is advanced over the needle by a predetermined distance to cover the hydrogel outlet, wherein the positioning mechanism is configured such that adjustment of the positioning mechanism to define a predetermined insertion depth of the needle proportionally adjusts the predetermined cannula insertion depth and is indicated by the cannula depth guide.

Optionally in any embodiment, the cannula depth guide comprises an arm that is attached to the fixed housing of the positioning mechanism for movement therewith and that extends distally of the movable hub.

Optionally in any embodiment, a length of the arm distal of the movable hub is preferably equal to the cannula insertion depth.

Optionally in any embodiment, the cannula depth guide is configured to act as a guide for distal axial movement of the cannula over the delivery needle when the predetermined cannula insertion depth has been reached.

Optionally in any embodiment, the cannula depth guide comprises an axially adjustable cannula extension member having a distal-most end that abuts the proximal end of the cannula and a proximal end that extends proximally of the movable hub of the positioning mechanism, whereby distal movement of the cannula extension member effects distal movement of the cannula over the needle. The positioning mechanism is configured such that when the fixed housing and movable hub are adjusted to define the predetermined needle insertion depth, the distance between the proximal end of the movable hub of the positioning mechanism and the proximal end of the cannula depth guide is preferably equal to the predetermined cannula insertion depth. The cannula extension member is coaxially mounted on the needle for axial movement relative to the needle and includes an elongated slot to accommodate coupling between the fixed housing and movable hub of the positioning mechanism.

Optionally, in any aspect, the invention employs imaging, for example a CT (computed tomography) scan, to correctly position the hydrogel delivery needle to deliver hydrogel just distal of the surface of the lung (the visceral pleura). A coaxial cannula may be inserted into the intercostal muscle of the chest wall with its distal-most end proximal of the parietal pleura. After the core of the coaxial cannula has been removed, an image may be taken which provides a distance P from the distal-most end of the cannula to the surface of the lung (or the pleural cavity). A hydrogel delivery needle having an adjustable depth positioning mechanism may then, prior to insertion into the cannula, be adjusted so that when fully advanced through the cannula the hydrogel outlet will be spaced a distance P+X from the distal-most end of the cannula, where the distance X is a predetermined distance within the lung tissue distal to the surface of the lung (the visceral pleura). The hydrogel delivery needle is then fully advanced through the cannula and hydrogel is delivered at the target location forming a closed annular seal around the needle. The coaxial cannula may then be advanced along the needle and through the seal with the cannula preferably covering the hydrogel outlet in the advanced position. The position mechanism of the hydrogel delivery needle may have a cannula depth guide to help a user advance the cannula over the needle such that it covers the hydrogel outlet by advancing the cannula a distance Y which is greater than P+X. The positioning mechanism may be configured so that its adjustment to correctly position the needle during advancement of the needle through the cannula proportionally adjusts the cannula depth guide.

Optionally in any embodiment, the positioning mechanism is configured to position the hydrogel outlet on the needle a distance (P+X) of preferably 3 to 30 mm or more preferably 5 to 20 mm from the distal-most end of the cannula when the needle is fully advanced into the cannula.

Optionally in any embodiment, the device comprises a cannula depth lock configured to fix the axial position of the coaxial cannula relative to the patient. The cannula depth lock can be positioned adjacent to the patient's skin and may be fixed to the patient's skin using skin adhesive. The coaxial cannula can be inserted through the cannula depth lock and the cannula depth lock can be locked to the cannula by a tightening screw, collet or other means, which fixes the coaxial needle preventing it from being inserted any further into the patient.

Optionally in any embodiment, the device comprises a locking arm configured for coupling the cannula depth lock to the delivery device to fix the axial position of the delivery device relative to the patient. The locking arm may be attached to any part of the positioning mechanism, and may be removable.

Optionally in any embodiment, the proximal end of the hydrogel delivery needle comprises a luer lock configured for attachment to a substance delivery device, for example a pump or syringe containing a reservoir holding the substance such as a hydrogel.

In another aspect, there is provided a system comprising a medical device according to the invention and a core biopsy needle configured for advancement through the coaxial cannula.

Optionally in any embodiment, the system comprises a core needle configured for advancement through the coaxial cannula and for use in generating a biopsy track through tissue. The core needle is typically comprised of a single elongated rod with a piercing tip and comprises a male luer lock attached at its proximal end. The male luer lock is configured to attach to the female luer lock of the coaxial cannula. When the male and female luer locks are attached, the piercing tip of the core needle extends from the distal most tip of the coaxial cannula, typically by a distance of 1-6 mm.

Optionally in any embodiment, the system comprises a viscoelastic hydrogel (for example, a viscoelastic hydrogel of the invention) suitable for injection through the hydrogel delivery needle.

Optionally in any embodiment, the viscoelastic hydrogel is a shear thinning hydrogel.

Optionally in any embodiment, the viscoelastic hydrogel is a hyaluronan hydrogel.

Optionally in any embodiment, the viscoelastic hydrogel exhibits a storage modulus (G') of greater than 400 Pa, more preferably greater than 800 Pa, more preferably greater than 1000 Pa, and a tan δ (G"/G') from 0.1 to 0.6 in dynamic viscoelasticity measured by a rheometer at 1 Hz and 1% strain rate at 25° C.

Optionally in any embodiment, the viscoelastic hydrogel comprises about 3-6% hydrogel forming polymer (w/v).

The invention provides a method of delivering a viscoelastic hydrogel (for example, a viscoelastic hydrogel of the invention) to a target location in the lung of a patient adjacent the visceral pleura of the lung, the method comprising the steps of:

inserting a coaxial cannula into a thoracic wall of a patient such that a distal-most end of the coaxial cannula is disposed proximal of the parietal pleura;

taking a first image of a part of the lung of the patient showing the lung, thoracic wall and coaxial cannula disposed in the thoracic wall;

using the first image to determine a distance P from a distal-most end of the coaxial cannula to the target path in the lung;

providing a hydrogel delivery needle comprising a hydrogel outlet and a positioning mechanism configured to adjust the insertion depth of the needle when fully advanced through the coaxial cannula;

actuating the positioning mechanism of the hydrogel delivery needle to adjust the insertion depth of the needle such that when the needle is fully advanced in the coaxial cannula the hydrogel outlet is spaced a distance of P+X from the distal-most end of the cannula; advancing the needle fully through the cannula; and injecting a hydrogel plug through the needle at the target location to form a sealing plug that embraces the needle and optionally abuts the visceral pleura.

Optionally in any embodiment, the distance P is determined by measuring a distance from the distal-most end of the cannula to the pleural cavity. The pleural cavity can be defined by the interface between the lung and the chest wall. A predefined distance inside the lung X can be added to the measured distance P to target a known depth of injection inside the lung.

Optionally in any embodiment, the method may include an additional step of advancing the coaxial cannula distally over the hydrogel injection needle and through the sealing plug.

Optionally in any embodiment, the positioning mechanism may include a cannula depth guide configured to indicate a predetermined insertion depth of the cannula relative to the needle at which insertion depth the distal-most end of the cannula is advanced over the needle by a distance greater than X to cover the hydrogel outlet, in which the step of advancing the coaxial cannula distally over the hydrogel injection needle and through the sealing plug is guided by the cannula depth guide.

Optionally in any embodiment, the method may include an initial step of imaging the thoracic wall of the patient to determine a suitable depth for insertion of the coaxial cannula into the thoracic wall so that the needle resides between 1-15 mm from the parietal pleura.

Optionally in any embodiment, the hydrogel is a viscoelastic hydrogel.

Optionally in any embodiment, the hydrogel delivery needle comprises a hydrogel outlet disposed on a side of the needle.

In another aspect, the invention provides a method of performing a lung needle biopsy, comprising the steps of:

delivering a viscoelastic hydrogel (for example, a viscoelastic hydrogel of the invention) to a target location in the lung of a patient adjacent the visceral pleura of the lung;

advancing the coaxial cannula distally over the hydrogel injection needle and through the sealing plug;

removal of the hydrogel delivery needle through the cannula;

advancing a biopsy needle through the cannula to a biopsy site within the lung;

actuating the biopsy needle to take a sample of lung tissue at the biopsy site;
withdrawing the biopsy needle through the cannula; and
withdrawing the cannula whereby the sealing plug seals the visceral pleura.

Optionally in any embodiment, after the removal of the hydrogel delivery needle and prior to advancement of the biopsy needle, the method includes the steps of insertion of a core needle into the coaxial cannula, advancement of the core needle and coaxial cannula to the biopsy site within the lung, and removal of the core needle.

Optionally in any embodiment, prior to removal of the hydrogel delivery needle, the method includes the steps of advancing the hydrogel delivery needle to the biopsy site within the lung, and then advancing the coaxial cannula over the hydrogel delivery needle to the biopsy site within the lung.

Optionally in any embodiment, the step of advancing the coaxial cannula distally over the hydrogel injection needle to the biopsy site in the lung is guided by the cannula depth guide.

Optionally in any aspect, the invention provides a method of performing a lung needle biopsy procedure comprising the steps of:
injecting a viscoelastic hydrogel (for example, a viscoelastic hydrogel of the invention) through a hydrogel delivery needle into the lung adjacent the visceral pleura of the lung to form a sealing plug that embraces the needle and abuts the visceral pleura;
advancing a coaxial cannula along the hydrogel delivery needle and through the closed annular sealing plug;
removal of the hydrogel delivery needle through the cannula;
advancing a biopsy needle through the cannula to a target location within the lung;
actuating the biopsy needle to take a sample of lung tissue at the target location;
withdrawing the biopsy needle through the cannula; and
withdrawing the cannula whereby the sealing plug seals the visceral pleura preventing pneumothorax.

In another aspect, the invention provides a method of performing a lung nodule localisation procedure comprising the steps of:
injecting a viscoelastic hydrogel (for example, a viscoelastic hydrogel of the invention) through a hydrogel delivery needle into the lung adjacent the visceral pleura of the lung to form a sealing plug that embraces the needle and abuts the visceral pleura;
advancing a coaxial cannula along the hydrogel delivery needle and through the closed annular sealing plug;
removal of the hydrogel delivery needle through the cannula;
advancing a tissue stain delivery needle through the cannula to a target location within the lung;
actuating the tissue stain needle to take a sample of lung tissue at the target location;
withdrawing the tissue stain needle through the cannula; and
withdrawing the cannula whereby the sealing plug seals the visceral pleura preventing pneumothorax.

In another aspect, the invention provides a method comprising delivery of a viscoelastic hydrogel (for example, a viscoelastic hydrogel of the invention) into a lung of a patient adjacent the visceral pleura of the lung to form a sealing plug wholly within the lung that abuts the visceral pleura.

Optionally in any embodiment, the viscoelastic hydrogel is a shear thinning hydrogel.

Optionally in any embodiment, the viscoelastic hydrogel is a hyaluronan hydrogel.

Optionally in any embodiment, the viscoelastic hydrogel is a high molecular weight hyaluronan hydrogel with a molecular weight in excess of 1000 kDa.

Optionally in any embodiment, the hydrogel delivery needle comprises a hydrogel outlet disposed at the distal-most tip of the needle.

Optionally in any embodiment, the hydrogel delivery needle comprises a hydrogel outlet disposed on a side of the needle.

Optionally in any embodiment, the hydrogel delivery needle comprises a plurality of hydrogel outlets disposed on a side of the needle.

Optionally in any embodiment, the sealing plug has a volume of 100 to 3000 μl of hydrogel, 100 to 1000 μl of hydrogel, or 200 to 900 μl of hydrogel.

Optionally in any embodiment, the methods of the invention involve delivering a volume of 100 to 3000 μl of hydrogel. Optionally in any embodiment, the methods involve delivering a volume of 100 to 1000 μl of hydrogel. Optionally in any embodiment, the methods involve delivering a volume of 200 to 900 μl of hydrogel. Optionally in any embodiment, the methods involve delivering a volume of 200 to 500 μl of hydrogel.

Optionally in any embodiment, the viscoelastic hydrogel is delivered into the lung through a needle having a piercing tip and a hydrogel outlet disposed on a side of the needle spaced apart from piercing tip.

In another aspect, the invention provides a viscoelastic hydrogel (for example, a viscoelastic hydrogel of the invention) for use in forming a sealing plug in a lung of a patient to prevent pneumothorax during a lung needle biopsy procedure, in which the sealing plug is delivered to the lung adjacent and abutting a visceral pleura.

Optionally in any embodiment, the biopsy needle is passed through the sealing plug during the needle biopsy procedure.

Optionally in any embodiment, a coaxial cannula is passed through the sealing plug, and the biopsy needle is passed through the sealing plug via the coaxial needle.

Optionally in any embodiment, the target location in the lung is located 0.2 to 6.0 mm distal of the visceral pleura.

Optionally in any embodiment the target location for delivery of the hydrogel material is into the pleural cavity. In this instance the hydrogel outlet will reside inside or across the pleural cavity.

Optionally in any embodiment, the hydrogel delivery needle may have a hydrogel outlet at the tip of the needle as opposed to the side. It is also possible to have both a hydrogel outlet at the tip of the needle and/or on the side of the needle. The delivery device and system described herein may also provide an effective solution to prevent bleeding during procedures requiring minimally invasive percutaneous access to other organs such as the liver and kidney. These procedures may include diagnosis or treatment of part or all of these organs.

Optionally in any embodiment, the system and viscoelastic hydrogel described herein can be used to separate tissue during a surgical procedure. This may be required to create a pathway through tissue for an instrument or to protect tissue from unwanted stimuli which as tumour ablation or radiotherapy. For this purpose a greater volume of viscoelastic hydrogel may be delivered, for example 1-25 ml.

Optionally in any embodiment, the system and/or the viscoelastic hydrogel described herein can be used as to fill voids in tissue or organs.

Optionally in any embodiment, the system and/or the viscoelastic hydrogel described herein can be employed in the prevention of adhesion between adjacent tissues and organs.

Optionally in any embodiment, the system and/or viscoelastic hydrogel described herein can be employed as a drug delivery vehicle. The viscoelastic hydrogel may be loaded with a drug or any other substance having physiological activity which will slowly diffuse from the hydrogel after its implantation into the body and the diffusion rate can be conveniently controlled by changing the compositional parameters of the hydrogel.

Optionally in any embodiment, the system and viscoelastic hydrogel described herein can be used as an embolic agent for occlusion of an artery or vein. The viscoelastic hydrogel can be deployed into an artery or vein to occlude the flow of blood, either on a temporary or permanent basis. In this manner, the hydrogel can be used to treat venous diseases, for example aneurysm, varicose veins, insufficient veins, dilated veins and ectasias.

In an alternative embodiment, the delivery device may be employed to deliver non-viscoelastic hydrogels, or other substances, to a target location in the lung, the thoracic cavity or in other organs, cavities, and vessels of a patient. These substances can include biocompatible polymer agents, particles, spheres, small expandable balloons, cell laden constructs, therapeutic agents, chemotherapy agents and suspensions.

Optionally in any embodiment, the devices and components described herein may be created using biocompatible materials including polymers, metals and ceramics. Polymers can include Polyether ether ketone, Polyethylene terephthalate, Nylon, polyimides, polyurethanes, polyesters, Pebax® and copolymers thereof. Metals may include stainless steel, nitinol, titanium and cobalt chrome. The needles and cannula may also comprise fully or partially flexible laser cut sections and braided sections to provide flexibility. The needles and cannula may also be both elongated and flexible such as in catheter type assemblies.

In a preferred embodiment, the compositions of the system, or the system as a whole can be provided sterile for clinical use. The hydrogel filled syringe can be prepared through an aseptic formulation, mixing, filling and packaging process. The hydrogel filling syringe may also be terminally sterilized through a heat or steam sterilization process for e.g., autoclaving. Sterilization of the system can also be performed via sterilization processes known in the field including sterilization by ethylene oxide, hydrogen peroxide, gamma ray and electronic beam.

Optionally in any embodiment, the components of the system can be provided in packaging suitable for sterilization including, but not limited to, a pouch, a blister pack, a bag, a procedure set, a tub, a clamshell, a skin pack, a tray (including lid), a carton, a needle sheath. The components of the system can all be assembled as a single packaged device. Alternatively, multiple packages containing the different components of the system can be prepared and sterilized separately. The components of the system can include but are not limited to the coaxial cannula with core needle, the hydrogel delivery needle, the cannula depth lock, locking arm, one or more syringes filled with viscoelastic hydrogel, empty syringes, hypodermic needles, scalpels, skin markers, radiopaque guides, scissors, biopsy needles, surgical drapes, antiseptic solution, swabs, swab holders, sponges, saline solution and histology tissue containers.

Optionally in any embodiment, the cannula depth guide can be configured for retro-fitting to the hydrogel delivery needle. This is useful as it allows the cannula depth guide to be put on when needed and removed when not needed.

Optionally in any embodiment, the cannula depth guide may comprise an engagement or locking feature configured to lock the delivery needle to the coaxial cannula at its second position.

Optionally in any embodiment, the methods described herein include an initial step of flushing the syringe with gel (or saline or water) prior to insertion of the needle into the body. The syringe may also be flushed with the hydrogel prior to insertion into the body.

Optionally in any embodiment, the piercing tip of the delivery needle is designed to prevent bleeding on insertion into the lung, for example it may have a non-cutting atraumatic needle tip profile, for example a pencil tip style needle or similar will help prevent bleeding.

Optionally in any embodiment, the piercing tip is designed with a sharpened bevel profile to minimise disruption of the parietal and visceral pleural layers as the needle is being advance through to the lung.

Optionally in any embodiment, the tip of the delivery needle may be blunt. Optionally in any embodiment the hydrogel outlet may be positioned distal to the blunt tip. Optionally in any embodiment the tip of the delivery needle may be configured with a veress needle tip that combines a spring activated blunt core and a sharp piercing tip.

Optionally in any embodiment the delivery needle is a single lumen. Optionally in any embodiment the delivery needle is comprised of a multi-lumen tube. The multi-lumen tube may be a single tube, or may be comprised of multiple individual tubes within another lumen (for example a stainless steel needle). The tubes may be connected to different delivery outlets. For example, one tube may be connected to a delivery outlet that is distal to the needle tip, whereas the other lumen may be connected directly to the needle tip. Individual delivery lumens may be used to deliver the hydrogel, deliver instruments, take measurements (pressure, temperature, impedance), extract tissue (for example FNA or core biopsies). The tubes may also be used to delivery crosslinking agents, chemotherapy agents and cellular solution (for example stem-cells).

Optionally in any embodiment the delivery needle may be comprised of a single tube. Optionally the single tube may comprise a tissue penetrating tip. Optionally the delivery needle may be comprised of two or more tubes bonded together, whereby the distal tube may form a tissue penetrating tip. The various tubes used to comprise the delivery needle can be made from radiodensity contrasting materials, for example stainless steel or polymer.

Optionally in any embodiment, the delivery needle can be provided with a central lumen to allow it to pass over a guidewire. The guidewire can be provided for access to body cavities or lumens.

Optionally in any embodiment the delivery needle and coaxial cannula can be given atraumatic and friction prevention properties by use of surface coatings and surface modifications such as polytetrafluorinated ethylene and silicone-based coatings. Optionally in any embodiment, the coaxial cannula can be provided with a bevel cut profile, fillet cut or chamfer cut on its distal-most tip to ease the force of insertion through the bodies tissues.

Optionally in any embodiment, the hydrogel delivery needle and coaxial cannula can be provided with external graduation marks on their exterior surfaces to monitor the depth of insertion into tissue and also to determine the position of the coaxial cannula in relation to the delivery needle. These depth graduations can be created using laser marking or ink pad printing or similar. Spacing of 5-10 mm between graduation marks are typical.

Optionally in any embodiment, the methods described herein include an aspiration step to ensure no major blood vessel is punctured. This aspiration step may be conducted when the delivery needle is inserted into the target location and before the hydrogel plug is injected. This may be desirable so as to limit or prevent any hydrogel from entering into the vasculature which may result in a pulmonary embolism. Aspiration of dark blood would be an indication that a major blood vessel has been punctured.

Optionally in any embodiment, the hydrogel filled syringe employed can be configured to require aspiration before injection of the hydrogel material. To achieve this, a mechanism can be built into the syringe to restrict the forward actuation of the syringe plunger until a retracting aspiration actuation has been performed.

Optionally in any embodiment the system describe herein may include an additional empty syringe for the purpose of performing the aspiration step.

Optionally in any embodiment the device may contain a 2- or 3-way medical stopcock fluidically attached to the delivery device. Any or both of the hydrogel filled syringe and the aspiration syringe may be attached to the delivery device via the medical stopcock which can be actuated to change and restrict the fluid delivery path between aspiration syringe and hydrogel filled syringe. This may provide the advantage of allowing a faster aspiration and injection step and reduce the time spend in the lung prior to injection of the hydrogel plug.

Optionally in any embodiment, the syringe is an ergonomic syringe for improved deliverability. Examples are described in US20090093787 A1 'Ergonomic Syringe' and U.S. Pat. No. 6,616,634 B2 'Ergonomic Syringe'. The system may also include an ergonomic syringe adapter which can be mounted onto the syringe. An example is described in U.S. Pat. No. D675,317 S1 'Ergonomic syringe adapter'. The syringe may include a mechanism to inject the viscoelastic hydrogel under high pressure. This may be in the form of a syringe assist device Optionally in any embodiment, the coaxial needle may have an internal sealing/valve feature that prevents any gel from entering the coaxial needle.

Optionally in any embodiment, the hydrogel delivery needle can be employed as a core needle within the coaxial needle.

Optionally in any embodiment, the positioning mechanism also comprises a firing mechanism, for example a spring-loaded firing mechanism, to quickly advance the delivery needle through the coaxial cannula to a predetermined depth. The required distance can either be a set distance for penetration depth, or can be adjustable to take into account the coaxial cannula position in relation to the target injection site. The device can be positioned using measurements taken through imaging.

The system, device and methods of the invention may employ a coaxial needle with a core that has a radiolucent marker for more accurate determination of position.

Optionally in any embodiment, a locking feature may be provided with the positioning mechanism of the delivery needle to enable the positioning mechanism to be locked and unlocked from the delivery needle. This feature would allow the positioning mechanism to be independent of the delivery needle so that it can be used with delivery needles of different lengths and be compatible with coaxial cannulas of different lengths.

Optionally in any embodiment the delivery device can be provided in an elongated and flexible configuration so that it can be passed through an endoscope to perform injections at predetermined injection depths via an endoscope. The elongated members can include both the coaxial cannula and delivery needle elements of the delivery device.

Optionally in any embodiment the delivery device can be provided with one or multiple energy delivery elements that can deliver sufficient energy into a target location so as to bring about a therapeutic effect. The elements can be positioned at the distal-most tip of the needle, or proximal to the distal-most tip. The delivered energy can be in the form of electrical, radiofrequency, thermal (including heating and cooling effect), microwave, short wave or acoustic energy. The energy delivering device can be connected at its proximal end to a power source which can include control and feedback capabilities. Irrigation channels can be incorporated in the delivery device to provide coolant to the treatment site during treatment. A typical application of this treatment would include cancer ablation.

Optionally in any embodiment the delivery device can be provided with sensors to provide feedback as to the local and/or surrounding tissue parameters including electrical, chemical, optical, acoustic, mechanical and thermal. Sensors can be disposed proximate, distal to and proximal to the hydrogel outlet.

In another aspect, the invention provides a method of performing a lung procedure (for example a lung biopsy or a lung ablation procedure), comprising the steps of:
advancing a coaxial cannula into the lung, wherein a distal portion of the coaxial cannula has one or more apertures in a side wall thereof;
advancing a lung procedure needle through the cannula to a procedure site within the lung;
actuating the lung procedure needle to perform a lung procedure at the procedure site;
withdrawing the lung procedure needle through the cannula;
advancing a hydrogel delivery needle through the coaxial cannula, wherein a distal portion of the hydrogel delivery needle has one or more apertures in a side wall thereof corresponding to the one or more apertures in the side wall of the coaxial cannula;
aligning the one or more apertures of the coaxial cannula and hydrogel delivery needle;
injecting a viscoelastic hydrogel (for example, a viscoelastic hydrogel of the invention) through the one or more outlets in the hydrogel delivery needle and one or more outlets of the coaxial cannula into the lung to form a sealing plug that embraces the coaxial cannula and typically abuts the visceral pleura; and
withdrawing the coaxial cannula and hydrogel delivery needle through the sealing plug.

In one embodiment, the viscoelastic hydrogel is delivered adjacent the visceral pleura of the lung. In one embodiment, the lung procedure needle is a biopsy needle. In one embodiment, the lung procedure needle is a tissue ablation probe.

In another aspect, the invention provides a composite viscoelastic hydrogel comprising a continuous phase and a dispersed polymer phase. In one embodiment, the dispersed phase is colloidal polymer. Examples include gelatin or collagen. In one embodiment, the viscoelastic hydrogel comprises 2-20% colloidal polymer. In one embodiment, the viscoelastic hydrogel comprises 5-15% colloidal polymer. In one embodiment, the viscoelastic hydrogel comprises 8-12% colloidal polymer. In one embodiment, the viscoelastic hydrogel comprises about 10% colloidal polymer. In one embodiment, the colloidal polymer comprises gelatin or collagen. In one embodiment, the continuous phase polymer comprises or consists of HA (or another glycosaminoglycan). In one embodiment, the viscoelastic hydrogel comprises about 2-6% continuous phase polymer (i.e. HA). In one embodiment, the viscoelastic hydrogel comprises about 3-5% continuous phase polymer (i.e. HA). In one embodiment, the viscoelastic hydrogel comprises about 4-5% continuous phase polymer (i.e. HA). In one embodiment, the continuous phase polymer (i.e. HA) is not cross-linked, or is lightly cross-linked.

In one embodiment, the invention provides a composite viscoelastic hydrogel comprising a continuous polymer phase comprising 2-6% polymer (i.e. HA), and a dispersed polymer phase comprising 2-20% colloidal polymer (i.e. gelatin) in the form of crosslinked polymer microbeads typically having an average dimension of less than 100 microns.

In one embodiment, the invention provides a composite viscoelastic hydrogel comprising a continuous polymer phase comprising 2-6% HA, and a dispersed polymer phase comprising 5-15% colloidal polymer in the form of cross-linked polymer microbeads having an average dimension of less than 100 microns.

BRIEF DESCRIPTION OF THE FIGURES

FIGS. 1A-1D. Series of lateral views illustrating a transthoracic needle biopsy procedure and demonstrating how a pneumothorax occurs (prior art).

FIGS. 2A-2E. Series of lateral views illustrating embodiments of the delivery device and a method of delivering a hydrogel plug to a target location in the lung.

FIGS. 8A-8H. A series of lateral views illustrating a method of delivering a hydrogel plug to a target location in the lung using the delivery device.

FIGS. 12A-12C. A series of images showing an ethanol fixed lung tissue specimen with hydrogel plug.

FIGS. 13A1-13B2. A series of lateral views showing an embodiment of the delivery device with cannula depth guide proximal to the measurement mechanism.

FIGS. 14A-14H. A series of lateral views illustrating a method for delivering a hydrogel plug to a target position in the lung using an embodiment of the delivery device.

FIGS. 24A-24C. Experimental set up and results from a hydrogel plug positioning and volumetric analysis generated using a 3D CAD model.

FIGS. 25A-25C. A series of lateral views illustrating a method of delivering a hydrogel plug to a target location in the lung after a biopsy procedure.

DETAILED DESCRIPTION OF THE INVENTION

Figures 3A, 3B:
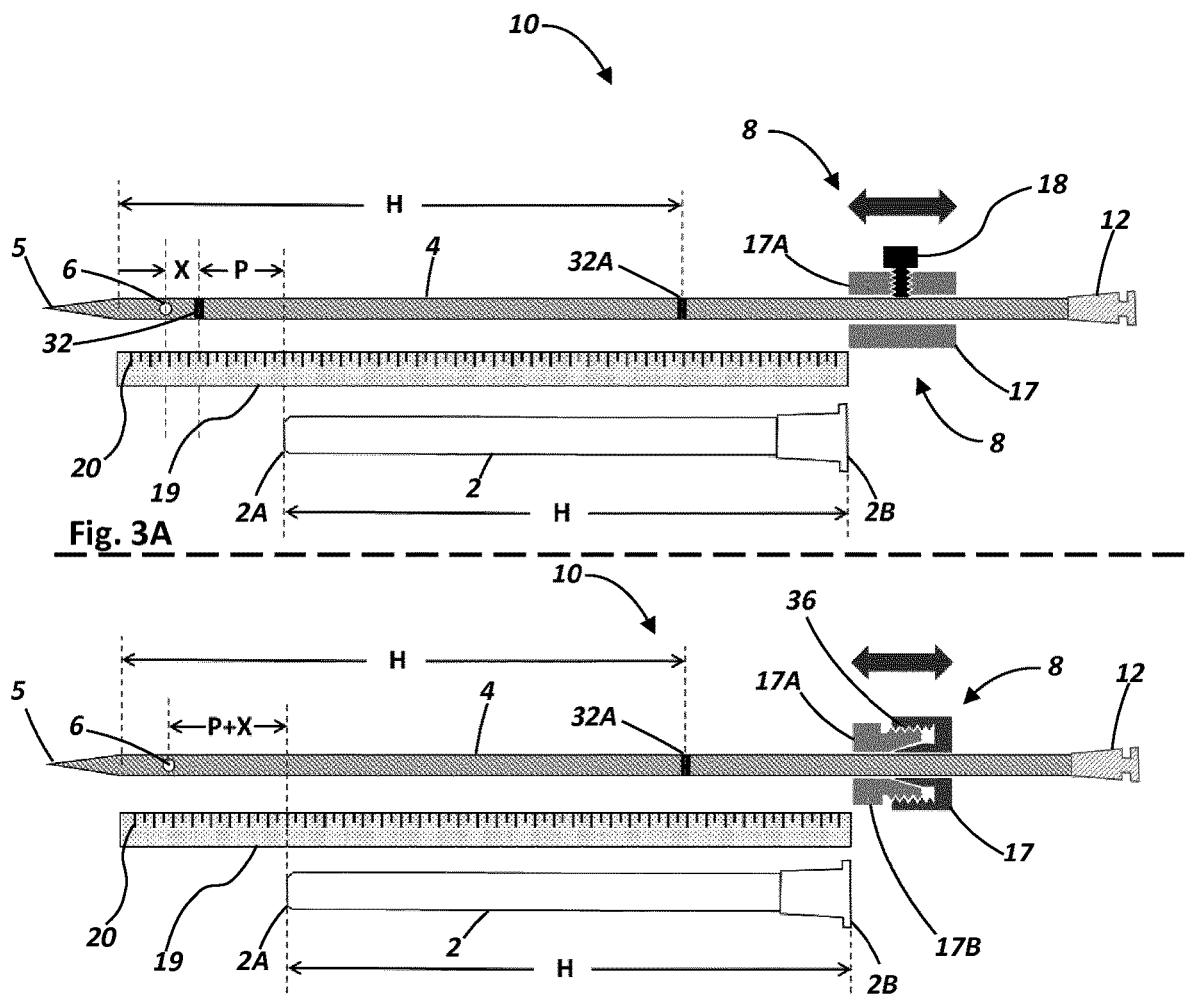
FIGS. 3A-3B. Series of lateral view illustrating embodiments of the delivery device.

All publications, patents, patent applications and other references mentioned herein are hereby incorporated by reference in their entirety for all purposes as if each individual publication, patent or patent application were specifically and individually indicated to be incorporated by reference and the content thereof recited in full.

The high efficacy demonstrated by exemplary embodiments disclosed herein is due to the unique viscoelastic properties of the hydrogel delivered. A hydrogel has both flow and elastic properties. Elasticity is reversible deformation; i.e. the deformed body recovers its original shape. The mechanical properties of an elastic solid may be studied by applying a stress and measuring the deformation of strain. Flow properties are defined by resistance to flow (i.e. viscosity) and can be measured by determining the resistance to flow when a fluid is sheared between two surfaces. The physical properties of a gel by viscoelasticity can be expressed by dynamic viscoelastic characteristics such as storage modulus (G'), loss modulus (G"), tangent delta (tan δ) and the like. Storage modulus characterizes the firmness of a composition and describes the storage of energy from the motion of the composition. Viscous modulus is also known as the loss modulus because it describes the energy that is lost as viscous dissipation. Tan δ is the ratio of the viscous modulus and the elastic modulus, tan δ=G"/G'. A high storage modulus and a low loss modulus indicate high elasticity, meaning a hard gel. Reversely, a high loss modulus and a low storage modulus mean a gel with high viscosity.

When the hydrogel described herein is used as a biomedical material, e.g., a biodegradable hydrogel plug for use in the periphery of the lung to prevent pneumothorax, it is considered that the increased stiffness and storage modulus of the gel can bring about improvement in sealing and barrier effect between tissues. It would also contribute to a prolonged duration (increased retention) at the target site, especially if the elasticity is greater than the elasticity of the surrounding tissues. The flowable nature of the hydrogel is due to its high Tan δ and at rest this allows for improvement in apposition with the surrounding tissue. This flow property also provides the hydrogel with its self-healing ability.

Therefore, it is preferably desirable that the gel for such use have well-balanced elasticity and viscosity. If the hydrogel zero shear viscosity is too high and if the gel does not portray sufficient shear thinning properties, it may become too difficult to inject through the delivery device into the target site. The gel may not readily appose surrounding tissue to form a barrier against fluid leak. Also, the gel may not readily flow back into the needle tract once the needle has been removed. On the other hand, if tan δ exceeds 0.8, the gel behaves like a solution, and it may infiltrate the surrounding tissue or be ejected from the needle tract. That is, the hydrogel described herein is regarded to have the most suitable physicochemical and rheological properties as a viscous plug for lung biopsy.

The term "viscoelastic hydrogel" therefore refers to a hydrogel that exhibits viscoelastic properties. It generally has a storage modulus (G') of preferably greater than 400 Pa, more preferably greater than 800 Pa and even more preferably greater than 1000 Pa. The viscoelastic hydrogel may exhibit a tangent delta (tan δ; G"/G') of from 0.01 to 0.8, preferably from 0.1 to 0.5 and more preferably from 0.2-0.5 in dynamic viscoelasticity at a frequency of 1 Hz. Preferably, the viscoelastic hydrogel exhibits a loss modulus (G") of from 200 to 6000 Pa, more preferably from 400 to 2000 Pa, in dynamic viscoelasticity at a frequency of 1 Hz at 25° C. The viscoelastic hydrogel may be free of crosslinking, lightly crosslinked, or strongly crosslinked to provide appropriate characteristics, for example to increase its storage modulus (G') or to increase its in vivo residence time.

As used herein, the term "shear thinning" as applied to a hydrogel means that when shear stress is applied to the hydrogel, the storage modulus (G') reduces, the tan δ increases and the overall viscosity reduces. This property provides injectable properties to the hydrogel. And allows it to be injected through a narrow-gauge needle, such as used in minimally invasive procedures such as lung biopsy (17-20 gauge) or lung ablation (10-14 gauge). The shear thinning hydrogel described herein typically exhibits a range of a storage modulus (G') of 1-100 Pa, preferably from 1-50 Pa in dynamic viscoelasticity at a frequency of 1 Hz and 100% strain. Furthermore, the hydrogel described herein has self-healing properties and retain their high storage modulus (G') and loss modulus (G") when the shear strain is removed.

The hydrogel described herein possess shear thinning capabilities. That is, when shear stress is applied, the storage modulus (G') reduces, the tan δ increases and the overall viscosity reduces. This property allows the gels to be injected through a narrow gauge needle, such as used in minimally invasive procedures such as lung biopsy. The gel described herein portrays the physical properties with ranges of a storage modulus (G') of less than 100 Pa, preferably less than 50 Pa in dynamic viscoelasticity at a frequency of 1 Hz and 100% strain. Furthermore, the gels described herein portrays rapid thixotropic recovery properties and retain their high storage modulus (G') and loss modulus (G") immediately on removal of the high shear rate.

The measurement of the dynamic viscoelasticity and dynamic viscosity was made with a rheometer Model AR2000 manufactured by TA Instruments under the following conditions.
Method of measurement: oscillation test method, strain control
Measuring temperature: 25° C.
Geometry: 4° cone plate angle
Measuring geometry: 4 cm
Truncation gap: 112 μm
Frequency: 1 Hz As used herein, the term "self-healing" as applied to a viscoelastic hydrogel of the invention refers to the ability of the hydrogel to reform together. "Self-healing" may also be described as the ability of the hydrogel to spontaneously form new bonds when old bonds are broken within the material. As an example, when an annular sealing plug of viscoelastic hydrogel is delivered around a delivery needle, a self-healing viscoelastic hydrogel will flow back together once the needle is removed to form a non-annular sealing plug, typically consisting of a single-bodied cohesive matrix.

Optionally in any embodiment the sealing hydrogel plug should be able to self-heal a channel through its centre independent of its in vivo environment. By this we refer to the ability of the hydrogel to fill the channel through a time dependent viscoelastic flow mechanism.

Optionally in any embodiment the sealing hydrogel plug should be able to self-heal a channel through its centre dependent on its in vivo environment. Stresses from the in vivo environment imposed on the hydrogel plug may improve its ability to self-heal in a shorter duration compared to an uninterrupted plug.

Optionally in any embodiment, the hydrogel should be able to self-heal under its own weight without any influence from the surrounding environment. This may be demonstrated by creating a singular mass of the hydrogel, for example a sphere of the hydrogel created using approximately 0.5 ml of hydrogel. A cylindrical channel can be created through the centre of the sphere by passing a 17 gauge needle through its centre and retracting the needle. The sphere with the cylindrical channel through its centre can be placed at rest on a bench with the axis of the cylindrical channel perpendicular to the bend. The size of the channel can be monitored over time. Referring to the viscoelastic hydrogels described in this invention, specifically hydrogels comprising 2-6% hyaluronic acid, the following are the observations: initially the channel in the ball will be visible, but over time (1-15 mins, depending on the hydrogel formulation) this channel will close over as the hydrogel self-heals. This is as a result of the time dependent flow of the hydrogel.

Optionally in any embodiment, part or all of the viscoelastic hydrogel is comprised of a hyaluronan hydrogel. The hyaluronan polymer forms a continuous phase throughout the three-dimensional matrix. Optionally in any embodiment, the viscoelastic hydrogel is a high molecular weight hyaluronan hydrogel. Optionally in any embodiment, the viscoelastic hydrogel is a shear thinning hydrogel (viscosity decreases under shear strain). Examples of polymer materials that may be employed to make a viscoelastic hydrogel include hyaluronan, especially high molecular weight hyaluronan. Other hydrogel materials suitable for use in the present invention are outlined in the review articles 'Shear-thinning hydrogels for biomedical applications', Soft Matter, (2012) 8, 260, 'Injectable matrices and scaffolds for drug delivery in tissue engineering' Adv Drug Deliv Rev (2007)

59, 263-272, and 'Recent development and biomedical applications of self-healing hydrogels' Expert Opin Drug Deliv (2017) 23: 1-15.

As used herein, the term "hyaluronan" or "hyaluronic acid" or "HA" refers to the anionic non-sulphated glycosaminoglycan that forms part of the extracellular matrix in humans and consists of a repeating disaccharide→4)-β-d-GlcpA-(1→3)-β-d-GlcpNAc-(1→, or any salt thereof. Hyaluronan is the conjugate base of hyaluronic acid, however the two terms are used interchangeably. When a salt of hyaluronic acid is employed, the salt is generally a sodium salt, although the salt may be employed such a calcium or potassium salts. The hyaluronic acid or hyaluronan may be obtained from any source, including bacterial sources. Hyaluronic acid sodium salt from *Streptococcus equi* is sold by Sigma-Aldrich under the product reference 53747-1G and 53747-10G. Microbial production of hyaluronic acid is described in Liu et al (Microb Cell Fact. 2011; 10:99). The term also includes derivatives of hyaluronic acid, for example hyaluronic acid derivatised with cationic groups as disclosed in US2009/0281056 and US2010/0197904, and other types of functionalised derivatives, such as the derivatives disclosed in Menaa et al (J. Biotechnol Biomaterial S3:001 (2011)), Schante et al (Carbohydrate Polymers 85 (2011)), EP0138572, EP0216453, EP1095064, EP0702699, EP0341745, EP1313772 and EP1339753.

Hyaluronic acid can be categorised according to its molecular weight. High molecular weight (preferably >1000 kDa (1 Mda)), medium molecular weight (preferably 250-1000 kDa), low molecular weight (preferably 10-250 kDa), and oligo hyaluronic acid (preferably <10 kDa). The effect of molecular weight on hyaluronic acid hydrogel viscosity has previously been reported. The stiffness and viscosity of the final gel is dependent on both molecular weight and solution concentration. In studying the rheological properties of hyaluronic acid with different molecular weights, Rheological and cohesive properties of hyaluronic acid J Biomed Mat Res, 76A, 4, Pg 721-728, Falcone et al found that high molecular weight hyaluronic acid is considerably more cohesive than low molecular weight hyaluronic acid. It has been shown that the presence of high molecular weight hyaluronic acid hydrogels at a wound site leads to reduction in scarring. High molecular weight hyaluronic acid has been shown to be anti-inflammatory, enhanced angiogenesis and enhanced immunosuppression. Jiang et al found that high molecular weight hyaluronic acid has been shown to protect from epithelial apoptosis in lung injury "Regulation of lung injury and repair by Toll-like receptors and hyaluronan" Nature Medicine (2005) 11, 11 1173-1179. Furthermore, inhalation of high molecular weight hyaluronic acid has been used to treat lung conditions such as bacterial rhinopharyngitis, chronic bronchitis, cystic fibrosis and asthma. In some embodiments, the hyaluronic acid compositions of the hydrogel are free from crosslinking and are free from other therapeutic agents. Hyaluronic acid based hydrogels with characteristics potentially suitable for this application are described in U.S. Pat. No. 9,492,474B2. 'Compositions of' hyaluronan with high elasticity and uses thereof. This document describes a material, Elastovisc™, comprised of high concentration and molecular weight hyaluronic acid. Its intended use is for injection into joints to relieve pain and treat osteoarthritis.

As used herein, the term "hyaluronan hydrogel" preferably includes a three-dimensional network of hyaluronan polymers in a water dispersion medium. The hyaluronan polymer forms a continuous phase throughout the three-dimensional matrix. Optionally in any embodiment, the hyaluronan polymers are non-crosslinked. Optionally in any embodiment, the hydrogel is free of a crosslinking agent. Optionally in any embodiment, the matrix is formed with a homopolymer, typically a hyaluronic acid homopolymer. Optionally in any embodiment, the hydrogel is a single gel system that is substantially free of other polymers. Optionally in any embodiment, the hydrogel is pH balanced or buffered to match the pH of the physiological environment. Optionally in any embodiment, the matrix is lightly cross-linked. Any crosslinking agent known to crosslink hyaluronic acid may be used for this purpose. Crosslinking agents may include epichlorohydrin, divinyl sulfone, I, 4-bis (2,3-epoxypropoxy) butane (or I, 4-bis (glycidyloxy) butane or 1,4 butanediol diglycidyl ether=BDDE), the I, 2-bis (2,3-epoxypropoxy) ethylene, I-(2,3-epoxypropyl)-2, 3-epoxy cyclohexane.

Optionally in any embodiment, the viscoelastic hydrogel may be comprised of 'multi-component' hydrogel which refers to at least two hydrogels that are evenly blended and dispersed together to form a homogenous hydrogel mixture. Each hydrogel will form a continuous phase throughout the hydrogel mixture. This construct may also be referred to as a semi-interpenetrating polymer (hydrogel) network or interpenetrating polymer (hydrogel) network comprised of two or more hydrogels. As an example, a hyaluronan hydrogel (concentration may range from 1-5%) may be blended with a methylcellulose hydrogel (concentration may range from 3-15%). In the same manner, more than two hydrogels may be combined to form a single cohesive network whereby each hydrogel provides improved properties to the overall network. The properties of each hydrogels may be provided to increase stiffness and viscosity, to provide improved injectability (shear thinning), to provide improved self-healing, to prolong the residence (biodegradation) time of the hydrogel in vivo, to provide haemostatic properties, to provide antibacterial properties, to provide anti-inflammatory properties, to provide anti-coagulant properties, to provide pro-coagulant properties, to provide colour and marking capability (under visible and radiographic detection), to provide some diagnostic or therapeutic effect (for example chemotherapy), to provide resistance to extremes of heat (hot and cold), to provide improved biocompatibility, and to improve manufacturability and preparation of the overall hydrogel. One or more of these hydrogels may be crosslinked to provide improved properties, for example to increase the residence time of the hydrogel in vivo Optionally in any embodiment, the viscoelastic hydrogel is a "colloidal hydrogel", which refers to a composition comprised of small hydrogel sub-units that combine to form a homogenous cohesive matrix. In a colloidal hydrogel the solution or dispersion medium that is referred to is typically water or saline but may be another biocompatible fluid. The colloidal hydrogel is typically formed by hydrating nano-sized or micronized biocompatible polymer particles, for example nano-particles, micro-particles, micro-capsules, micro-fibres, micro-spheres, and/or fragmented particles. The particles may be regular or irregular in shape and size. Exemplary polymers include proteins selected from gelatin, collagen (e.g. soluble collagen), albumin, haemoglobin, dextran, fibrinogen, fibrin, fibronectin, elastin, keratin, laminin, casein and derivatives and combinations thereof. The polymer may comprise a polysaccharide, such as a glycosaminoglycan (e.g., hyaluronic acid, hylan or chondroitin sulphate), a starch derivative, a cellulose derivative, a hemi-cellulose derivative, Xylan, agarose, alginate, chitosan, and combinations thereof. As a further alternative, the polymer may comprise a non-biologic hydrogel-forming polymer, such as polyethylene glycols, polyacrylates, polymethacrylates, polyacrylamides, polyvinyl polymers, polylactide-glycolides, polycaprolactones, polyoxyethylenes, and derivatives and combinations thereof. These particles may be capable of being crosslinked by varies means known in the art including both physical (heat, cold, radiation) and chemical crosslinking. As an example, the crosslinked polymer may comprise of a dehydrothermally crosslinked gelatin powder whereby the gelatin is rendered insoluble by dehydration at elevated temperatures for a prolonged period. Typically temperatures in excess of 100° C. are used for this process and dry heat or vacuum heating can be employed. The degree of crosslinking resulting from increased dehydration of the gelatin powder influences the degree of swelling by water absorption. Optionally in any embodiment, the viscoelastic hydrogel comprises about 0.2-30%, 15-28%, or 20-25% hydrogel forming polymer (w/v).

Optionally in any embodiment, the viscoelastic hydrogel is a "biphasic" hydrogel, which refers to a hydrogel formed by combining (through mixing or blending) a colloidal hydrogel with a continuous phase hydrogel. The colloidal hydrogel will form an evenly dispersed phase in the continuous hydrogel phase. A variety of natural and synthetic biodegradable polymers can be used to form the continuous hydrogel phase. Glycosaminoglycans, for example hyaluronan and its derivatives form one example. The hyaluronan may be preferably non-crosslinked or possibly lightly crosslinked so as to retain its viscoelastic properties, especially its shear thinning and self-healing ability. Optionally in any embodiment, the hyaluronan may be provided at concentrations of 1-6%, preferably 3-5%. Optionally in any embodiment, the hyaluronan would dominate the rheological properties of the biphasic hydrogel. A variety of biodegradable polymers are also suited to form the colloidal hydrogel phase as outlined previously (collagen and gelatin are two examples). The colloidal hydrogel phase can be added in sufficient quantities to provide the advantage of increased residence time of the hydrogel in vivo. This can allow the necessary time to provide for healing of the tissue. An additional benefit is that an increased residence time can provide a long-term marking function of the biopsy side for use under video-assisted thoracoscopic (VATS) surgery. A suitable polymer is one that is insoluble in an aqueous environment and can be achieved by crosslinking of the polymer through conventional means. An example would be dehydrothermally crosslinked gelatin. It should be noted that by introducing a too large amount of the colloidal hydrogel phase, it may jeopardize the injectability and self-healing ability of such compositions. Optionally in any embodiment, the "biphasic" hydrogel can comprise a colloidal hydrogel at concentrations of 0.2-30%, 15-28%, or 20-25% of hydrogel forming polymer (w/v).

Optionally in any embodiment, the viscoelastic hydrogel exhibits a storage modulus (G') of greater than 400 Pa, more preferably greater than 600 Pa, more preferably greater than 800 Pa, more preferably greater than 1000 Pa. Optionally in any embodiment, the viscoelastic hydrogel exhibits tan δ (G''/G') from 0.01 to 0.8, more preferably 0.1 to 0.6 in dynamic viscoelasticity measured by a rheometer at 1 Hz and 1% strain rate at 25° C.

Optionally in any embodiment, the viscoelastic hydrogel may be provided as a powder that is reconstituted in a physiologically acceptable fluid, for example water, saline, autologous blood, or autologous plasma prior to the surgical procedure. Synthetic fluids such as low molecular weight PEG and glycerol may also be employed. The powder may be comprised of any suitable biocompatible polymer or combinations of polymers. In one embodiment, the powder may be provided in the hydrogel delivery needle. In one embodiment, the powder may be provided in a syringe with a suitable reconstitution fluid provided in a second syringe. In one embodiment, the powder has an average particle size of 1-500, 10-100 or 30-40 microns. The powder may be both regular or irregular in both shape, morphology and size distribution and may be formed through milling or other means known in the art. In certain instances, powder hydration can be controlled by varying the level of de-hydration of the powder particles such as in the case of collagenous based materials, for example collagen or gelatin.

Optionally in any embodiment, the hydrogel described herein may be provided in separate components, for example in multiple syringes and the means can be provided to allow mixing of the components prior to injection through the syringe. Crosslinking agents can be provided in one or more of these components to provide the material characteristics necessary to achieve a shear thinning and self-healing hydrogel. Mixing can be achieved by reciprocating the contents between the syringes and a static mixer can be employed to speed up this process.

In any embodiment the viscoelastic hydrogel composition can be provided in a physiological buffer, e.g., a phosphate buffer or a bicarbonate buffer. In some embodiments, the pH of the composition is between pH 7 and pH 9 or between pH 7.5 and pH 8.5. In some embodiments, the pH of the composition is 8.0. In some embodiments, the pH of the composition is 7.5. In some embodiments, the pH of the composition is 8.5. If needed, acid (such as HCL) or base (such as NaOH) can be added to the composition to attain the desired pH. In a specific embodiment, the hyaluronic acid hydrogel described herein consists essentially of hyaluronic acid present at a concentration of 50 mg/ml (or about 5% W/V, and having an average molecular weight of between 1-2 Mda. Ranges intermediate to the recited values are also intended to be part of this invention. For example, hyaluronan content in the compositions described herein may be between about 3% and about 15% (weight/volume), between about 3% and about 10% (weight/volume), about 3.5% and about 9% (weight/volume), about 4% and about 8% (weight/volume), or about 5% and about 7% (weight/volume). It should further be appreciated that the amount of hyaluronan in a particular volume may also be expressed by alternative means (e.g., gram/litre or mol/litre). A person of ordinary skill in the art would know how to convert the various means of expressing the amount of hyaluronan in a particular volume As used herein, the term "sealing plug", "hydrogel plug" or "gel plug" refers to a single body of viscoelastic hydrogel, for example hyaluronic acid hydrogel, that is suitable for delivery through a needle to a locus in the lung and which has sufficient viscoelasticity to push away the tissue surrounding the needle and coalesce to form a single closed annular sealing plug around the needle. The viscoelastic properties and stiffness of the gel prevents infiltration of the tissue, allowing the gel to precisely oppose the tissue and form an effective seal around the needle and subsequently cannula thereby preventing air from lungs leaking past the plug. The viscoelastic behaviour of the hydrogel allows the annular plug to coalesce upon removal of the cannula filling the hole in the annular plug and bearing against the visceral pleura to seal it after withdrawal of the coaxial cannula.

Optionally in any embodiment, the hydrogel plug should exhibit "limited-swelling" behaviour which means that its bulk size should not increase by any profound extent when placed in vivo, for example below the surface of the lung to prevent pneumothorax. A hydrogel plug that swells by a significant degree may cause unwanted physiological or biological effect. Some swelling of hydrogels in vivo is to be expected but in order to preserve the native tissue, swelling of the hydrogel plug should be limited. Swelling can be characterised by forming a predetermined size of hydrogel sphere, for example rolling 500 µl of hydrogel into a sphere, and by placing this ball of hydrogel into an aqueous solution. This volume 500 µl will initially equate to a sphere with a diameter of approx. 10 mm. The aqueous solution may be a saline or simulated body fluid solution and it may also contain the correct enzyme activity that is found in vivo. The size and shape and dissolution of the ball of hydrogel can then be monitored over a prolonged period of time. The swelling ratio can be determine from:

Swelling (%)=$(Ws-Wd)/Wd \times 100$

[Wd=Weight of polymer; Ws=weight of swollen polymer]

Preferably the selling ratio should not exceed 250%, more preferably it should not exceed 150%, and more preferably it should not exceed 130%. Sample degradation can be determined by comparing the dry weight of the polymer over time. Dry weight can be determined by lyophilising the samples. The degradation rate can be inferred from the remaining weight of the hydrogel:

Remaining Hydrogel (%)=$(W2-W1)/W1 \times 100$

[W1=Original dry weight of polymer; W2=time dependent dry weight of polymer]

Different polymeric materials with thermo-responsive, shear-thinning, shape memory and biological properties can be combined to yield composite hydrogels with improved properties for this application. Improvements can include enhanced biocompatibility, injectability, viscosity, altered biodegradation, drug attachment, tissue adhesion, cohesiveness, sealing ability stability, hydrophilicity. Gelatin and hyaluronic acid are two examples. Substances which can be combined with these polymer include methylcellulose, oxidized cellulose, carboxylmethyl cellulose, and carboxylic acid.

Optionally in any embodiment, the viscoelastic hydrogel is formed from a thermoresponsive substance. A range of thermoresponsive hydrogels suitable for this purpose have been described previously by Klouda: 'Thermoresponsive hydrogels in biomedical applications: a seven year update' Eur J Pharm Biopharm 2015 97(PtB) 339-49, and by Ruel-Gariépy: 'In situ-forming hydrogels—review of temperature-sensitive systems' Eur J Pharm Biopharm 2005 58 409-426. Of particular note are Poloxamers, a family of nonionic triblock copolymers with a centre block of hydrophobic polypropylene oxide (PPO) flanked by two hydrophilic polyethyleneoxide (PEO) blocks. The Food and Drug Administration has designated poloxamer 407 as an inactive ingredient for different types of preparations. At solution concentrations above 20%, poloxamer 407 undergo thermoreversible gelation between room and body temperatures. The addition of hyaluronic acid to poloxamer solutions to form thermoresponsive hydrogels for drug delivery applications has been described by Moyol et al: 'A novel poloxamer/hyaluronic acid in situ forming hydrogel for drug delivery: rheological, mucoadhesive and in vitro release properties' Eur J Pharm Biopharm 2008 70 199-206.

Optionally in any embodiment, the viscoelastic hydrogel can be formed by mixing a quantity of a thermoresponsive hydrogel with a quantity of shear thinning hydrogel such as hyaluronic acid to increase the final stiffness of the hydrogel, influence its biodegradation and its biocompatibility. This addition will provide the additional benefit that it will have little impact on the injection force required to inject the hydrogel through the delivery needle.

Optionally in any embodiment, the viscoelastic hydrogel can include contrast medium which refers to an additive that can be included in the gel in an appropriate amount that allows the hydrogel to be contrasted against the surrounding tissue. In this way, the hydrogel plug and injected location can be visually identified and/or targeted for example during the surgical procedure or during a follow up surgical procedure. Identification can be visual or through guidance systems such as CT scans, ultrasound or fluoroscopy. Additives which can be added to the hydrogel in varying concentrations to achieve effective visual contrast include ionic and non-ionic contrast medium, methylene blue, indigo carmine, toluidine blue, lymphazurine, hemotoxylin, eosin, indocyanine green (ICG), India ink, carbon based powders such as carbon black, carbon nanotubes and graphene, and ceramic powders such as aluminium oxide, titanium dioxide, and calcium phosphates. The hydrogel may also comprise additional detectable marking agents. The detectable marking agent suitable for use in the hydrogel described herein may include any composition detectable by spectroscopic, photochemical, biochemical, immunochemical, electrical, optical or chemical means. A wide variety of appropriate detectable markers are known in the art, which include luminescent labels, radioactive isotope labels, and enzymatic labels. These marking agents can be mixed with the hydrogel or chemically conjugated to the hydrogel molecules.

Optionally in any embodiment, the viscoelastic hydrogel can comprise of a therapeutic agent or biologically active agent. Therapeutic agents which may be linked to, or embedded in, the hydrogel include, but are not limited to, analgesics, anaesthetics, antifungals, antibiotics, anti-inflammatories, anthelmintics, antidotes, antiemetics, antihistamines, antihypertensives, antimalarials, antimicrobials, antioxidants, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, sedatives, stimulants, sympathomimetics, tranquilizers, urinary anti-infectives, vasoconstrictors, vasodilators, vitamins, xanthine derivatives, and the like. Optionally in any embodiment, the hydrogel described herein comprises one or more anesthetics. Exemplary anesthetics include, but are not limited to, proparacaine, cocaine, procaine, tetracaine, hexylcaine, bupivacaine, lidocaine, benoxinate, mepivacaine, prilocalne, mexiletene, vadocaine and etidocaine. Optionally in any embodiment, the viscoelastic hydrogel can further comprise foaming agents, foam stabilizers, surfactants, thickeners, diluents, lubricants, wetting agents, plasticizers.

Optionally in any embodiment, part or all of the viscoelastic hydrogel can be "biodegradable" and configured to degrade over time in-vivo. Different phases or components of the viscoelastic hydrogel can be configured to degrade at different rates. Biodegradable substances are preferably eliminated by the body without causing an inflammatory or immune response. For the viscoelastic hydrogel described herein, the period of time for full biodegradation can be less than 1 year, preferably less than one month, more preferably less than 1 week, and more preferably less than 72 hours. The added benefit of a quick degradation period is that it allows the lung tissue to return to normal and prevents excess scar tissue formation at the delivery site. Also, limiting residence time and scar tissue formation ensures that the delivery of the hydrogel plug does not interfere with follow up radiological analysis of the suspected lung lesion. Non-crosslinked systems may result in a faster in vivo residence period compared to crosslinked systems. The high molecular weight (>1000 kDa) and high concentration (40-60 mg/ml) hyaluronic acid hydrogels described herein have a degradation period of less than 1 week and also less than 72 hours. Longer degradation periods are possible by modifying the native hyaluronic acid molecular structure via crosslinking or by other means. Longer degradation periods are also possible by combining the hyaluronic acid hydrogel with one or more hydrogels or colloidal hydrogels to form a composite hydrogel. One of the hydrogels will remain at the target site for a longer period while the other is removed. For example, the hyaluronic acid hydrogel may be combined with a crosslinked polymer (for example hyaluronan, hylan, collagen or gelatin) to form a composite hydrogel. The cross-linked polymer can be configured to have a residence time of greater than 1 week, and often greater than 2 weeks by the use of various crosslinking modalities known in the art. Cross-linkers employed as part of the implantable material precursors can include aldehydes, polyaldehydes, esters, and other chemical functionality suitable for cross-linking protein(s). Physical crosslinking methods can also be employed, for example subjecting the polymers to heat, cold or radiation. Crosslinking agents can be added to improve cohesion, rigidity, mechanical strength and barrier properties.

As used herein, the term "in-vivo residence time" as applied to a sealing plug of viscoelastic hydrogel refers to the period of time that sealing plug of 0.1-1 ml, preferably 0.2-0.8 ml and more preferably 0.3-0.5 ml that persists in lung tissue in-vivo without any significant loss of structure integrity. The in-vivo residence time should be sufficient to allow healing of the hole in the visceral pleura to occur, and ideally to allow for healing in the surrounding lung tissue to occur. Methods of approximating the in-vivo residence time of hydrogels are described below. To achieve an appropriate in-vivo residence time to allow healing to occur, the hydrogel can be comprised of certain unmodified materials (including proteins) that have a longer residence time. Examples include collagen, oxidised cellulose, starch, extracellular matrix (ECM). Crosslinked hydrogels as described herein have been found to have an in-vivo residence time of more than two weeks. Optionally, the shear-thinning viscoelastic hydrogel may have an in-vivo residence time of at least 1 week, preferably at least 2 weeks, and ideally at least 3 weeks.

In any embodiment, the positioning mechanism can be adjustable to vary the depth of insertion of the delivery needle through the coaxial cannula when fully advanced through the cannula (in a first adjustment), and then guide the insertion depth of the coaxial cannula over the needle (in a second subsequent adjustment). The first movement positions the needle in the tissue to deliver the substance (hydrogel) into the lung to form a sealing plug, and the second adjustment advances the cannula over the needle through the sealing plug covering the hydrogel outlet. The positioning mechanism can be pre-set to define a predetermined insertion depth X. The predetermined insertion depth X is generally the depth at which the hydrogel outlet on the needle is located at a target position in the lung tissue, for example just distal of the visceral pleura. The positioning mechanism generally includes a cannula depth guide that is configured to provide an indication to a user of a cannula insertion depth Y at which depth the distal-most end of the cannula has passed through the sealing plug. The positioning mechanism is configured such that when a user adjusts the depth of insertion of the needle, the cannula depth guide is also adjusted. In any embodiment, the positioning mechanism may comprise a movable hub that is axially movable along the needle from a distal position which provides a first insertion depth and a proximal position which allows a second insertion depth greater than the first insertion depth. The positioning mechanism may comprise a fixed housing attached to the hydrogel delivery needle, a movable hub mounted to the needle for axial movement along the needle and having a distal-most end configured to abut a proximal end of the coaxial cannula, wherein the fixed housing is configured to cooperate with the movable hub for relative axial movement to define the predetermined needle adjustment depth. The positioning mechanism may comprise a cannula depth guide comprised of an arm that is attached to the fixed housing of the positioning mechanism for movement therewith and that extends distally of the movable hub. The length of the arm distal of the movable hub is preferably equal to the cannula insertion depth. Generally, the cannula is first inserted into the muscle tissue proximal to the pleural cavity, and then an image is taken to determine the distance P between a distal-most end of the cannula and the pleural cavity along the target direction in the lung. This distance P is then used to adjust the positioning mechanism using a scale 20,16A on the positioning mechanism such that when the needle is fully inserted in the cannula the hydrogel outlet is disposed at the target position a distance P+X. This adjustment automatically adjusts the cannula depth guide to provide an indication to a user of a cannula insertion depth Y.

Optionally in any embodiment, the procedures described herein require imaging guidance, for example an image generated by CT scan, fluoroscopy or ultrasound. The methods described herein may involve taking one or more images of lung/intercostal muscle to assist with the procedure. An image may be initially taken to determine an initial insertion depth of the cannula. An image may be taken when the coaxial cannula is in its first position in order to determine a distance P from the distal-most end of the cannula to the intended organ along the desired needle trajectory. The methods described herein may involve taking an additional image of the lung, to determine the distance to advance the cannula into the target organ so that the cannula is positioned at the tip of the delivery needle. Generally, these images will be taken under the guide of an interventional radiologist and a radiographer.

EXEMPLIFICATION

The invention will now be described with reference to specific examples. These are merely exemplary and for illustrative purposes only: they are not intended to be limiting in any way to the scope of the monopoly claimed or to the invention described. These examples constitute the best mode currently contemplated for practicing the invention.

The mechanism of pneumothorax resulting from a transthoracic needle biopsy is illustrated in FIGS. 1A-1D (Prior art). FIG. 1A illustrates a cross section of the thoracic cavity A, which comprises the thoracic (chest) wall muscle B, ribs C, lung tissue D, and the pleural cavity E defined by the serous membrane of the thoracic wall (parietal pleura F) and the serous membrane of the lung (visceral pleura G). During a lung biopsy procedure (FIG. 1B), a core needle H and coaxial cannula I are advanced percutaneously through the skin O and through the pleural cavity E towards a suspected lung nodule J. In FIG. 1C the core needle H has been withdrawn and replaced with a biopsy needle K which is advanced through the cannula 2 and obtains a tissue sample from the suspected lung nodule J. As illustrated in FIG. 1D, removal of the biopsy needle K and cannula I leaves a void L in the lung tissue D and also leaves a hole L1 in the visceral pleura G. The dense muscular tissue of the thoracic wall B contracts around the void caused by removal of the needles. However, the holes L, L1 created by the biopsy needles in the lung tissue D and visceral pleura G do not completely seal over. Due to the pressure gradient between the lung tissue D and pleural cavity E, air escapes through the hole L1 created in the visceral pleura G and enters the pleural cavity E, creating a collection of air in the pleural cavity E known as a pneumothorax M. If a blood vessel of significant size is punctured during the biopsy procedure the pleural cavity may also fill with blood, a condition known as a haemothorax. The prevalence of haemothorax is not as high as pneumothorax. The haemothorax or pneumothorax M can grow in sufficient size to cause the lung to partially or fully collapse and bring about respiratory distress and the need for treatment.

Referring to FIGS. 2A-2E, a method for overcoming the shortcomings of the prior art is presented. In FIGS. 2A-2E, a method of delivering a viscoelastic hydrogel plug to a target location in the lung is described. This embodiment, employs a medical device system comprising a coaxial cannula 2 having a distal-most end 2A and a proximal connector such as a luer lock 2B, a core needle 3, and a hydrogel delivery needle 4 having a distal tissue piercing tip 5 and a hydrogel outlet 6 disposed on a side of the needle proximal of the piercing tip 5. Also contained in the system is a syringe 15 with reservoir 15b filled with viscoelastic hydrogel material including any of those described herein. The syringe may be replaced by any pump, plunger, fluid advancement mechanism or element suitable for delivering a viscous hydrogel.

As shown in FIG. 2A, the core needle 3 and cannula 2 assembly are inserted into the chest wall of the patient to a depth at which the assembly is located in the chest wall B and does not penetrate the lung D. A coaxial cannula 2 refers to a needle device having an inner lumen configured to receive a penetrating device, for example a core needle 3 where the assembled core needle and cannula 2 may be used to enter through the skin surface on the chest. Generally, the coaxial cannula has a gauge size of 10 to 19. In additional embodiments, the coaxial cannula may also be referred to as a sheath, an introducer, an obturator/stylet assembly, a guiding catheter, trocar, port device or other medical introductory device known in the art.

As shown in FIG. 2B, the core needle 3 has been withdrawn from the cannula 2 and a hydrogel delivery needle 4 is advanced through the cannula 2. The hydrogel delivery needle 4 typically has a piercing tip, and a hydrogel outlet 6 which is typically disposed on a side of the needle proximal of the piercing tip 5, for example 0.5-15 mm from the piercing tip 5. The delivery needle 4 has a distal-most end configured for insertion into the body, and a proximal end which during use is positioned outside of the body. The needle is generally formed from a metal, although the positioning (adjustment) mechanism may be formed from plastic or polymer or a metal. The needle may comprise polymer tubing at its proximal end and may include a luer lock to facilitate fluidically connecting the needle (or polymer tubing part) to a pump or syringe 15. Generally, the hydrogel delivery needle 4 has a gauge of 13 to 20. The hydrogel delivery needle 4 is inserted to a depth at which the hydrogel outlet 6 is positioned in the lung tissue distal of the pleural cavity E and visceral pleura G. Positioning of the hydrogel outlet 5 at this target location may be achieved under CT guidance by employing a radiopaque or radiolucent marker 32 on the delivery needle which can be positioned a known distance X from the hydrogel outlet 6. By overlaying the radiolucent marker 32 with the pleural cavity E, the hydrogel outlet can be positioned a predetermined distance X inside the lung D from the pleural cavity E. The pleural cavity E is a very thin space approximately 25 µm in width and is often referred to as a virtual cavity. As can be seen later in FIG. 7, the pleural cavity E can be distinguished under CT guidance as the transition between the lung (dark area) and chest wall (bright area). Positioning of the radiolucent marker 32 over the pleural cavity E may be achieved by stepwise scanning and fine adjustment of the needle 4, or with fine adjustment under continuous fluoroscopic guidance.

As shown in FIG. 2C, a syringe 15 with hydrogel filled reservoir 15B is attached to the delivery needle 4 via a luer lock 12. A predefined quantity of viscoelastic hydrogel is then injected into the lung through the hydrogel outlet 6 to form a closed annular viscoelastic sealing plug 7 around the delivery needle 4. Subsequent to this step, the coaxial cannula 2 is advanced over the delivery needle 4 through the sealing plug 7 and towards the suspected lung nodule J. The hydrogel delivery needle 4 is withdrawn leaving the cannula 2 with surrounding hydrogel sealing plug 7 in place for receipt of a lung biopsy needle K. As shown in FIG. 2D a lung biopsy needle K can be then advanced through the cannula 2 and a lung biopsy carried out, The biopsy needle K and cannula 2 are both withdrawn after the biopsy has been taken. As shown in FIG. 2E the sealing plug 7 remains in position in the lung tissue after the needles have been withdrawn. Due to the physical properties of the viscoelastic hydrogel material, the sealing plug 7 reflows into the space left behind by the needles, as well as sealing the hole L1 left in the visceral pleura G by the coaxial cannula 2. These steps describe a method of performing a lung biopsy with diminished chance of causing a pneumothorax. The efficacy of the sealing plug 7 is dependent on its ability to block any air in the aerated lung tissue D from exiting the hole L1 in the visceral pleura G.

For a number of reasons it may be difficult to position the delivery device as outlined above. Firstly, fluoroscopic guidance may not be available to the clinician so that the delivery needle 4 with marker band 32 cannot be accurately positioned. Secondly, it may be harmful to expose the patient to too many CT scans and resulting high radiation dose to achieve accurate placement of the needle marker band 32. Furthermore, delayed placement of the hydrogel plug may lead to potential pneumothorax while the needle is in the lung tissue unprotected. In order to quickly, easily and accurately target the required depth of injection in the lung for the viscoelastic hydrogel to achieve an effective seal, a positioning mechanism is provided with the hydrogel delivery needle 4 as will be described hereafter.

Referring to FIGS. 3A-3B and FIGS. 4A-4F there is illustrated a medical device in which parts identified with reference to the previous embodiments are assigned the same reference numerals. FIG. 3A shows the medical device, indicated generally by the reference numeral 10, and comprises a single lumen hydrogel delivery needle 4 having a distal piercing tip 5, a hydrogel outlet 6 disposed on a side of the needle proximal of the piercing tip 5, a marker band 32 disposed on the needle proximal to the hydrogel outlet 6, a positioning mechanism 8 disposed along the delivery needle 4, and a luer lock 12 attached to the proximal end of the delivery needle 4. A visible mark 32A is provided on the delivery needle 4 proximally to the piercing tip 5, where the distance between the visible mark 32A (distance denoted as H) is equal to the length of the coaxial cannula 2. This visible mark 32A may be used to indicate when the distal end of the coaxial cannula 2 is adjacent to the piercing tip 5 when the delivery needle 4 is inserted through the lumen of the coaxial cannula 2. The components of the positioning mechanism 8 are shown in cross-sectional view for illustration purposes and include a movable hub 17 that is free to slide along the axis of the delivery needle 4. The movable hub 17 is a single body of material that comprises a central channel through which the delivery needle 4 passes. A threaded locking screw 18 is mounted on the side of the movable hub 17 perpendicular to the axis of the delivery needle 4 and passes through the movable hub 17 to access the delivery needle 4. Rotation of the threaded locking screw 18 will secure the axial position of the positioning mechanism 8 at a chosen point along the delivery needle 4. Also included with the medical device 10 is a coaxial cannula 2 which includes a central lumen passing from the proximally located female luer lock 2B to its distal most face 2A. The lumen of the coaxial cannula 2 is configured to accept the central passage of the delivery needle 4. Also included in the medical device is a measurement device 19 including a graduated measurement scale 20. The measurement device 19 may include a ruler, a calipers, a micrometer device or any other form of mechanical or digital measurement mechanism. The purpose of the measurement device 19 is to position the hydrogel outlet 6 a predetermined target distance from the distal most face 2A of the coaxial cannula 2 when the delivery needle 4 is advanced through the coaxial cannula 2 and when the distal most face 17A of the positioning mechanism 8 abuts the luer lock 2B of the coaxial cannula 2. The positioning mechanism 8 can be locked at this target distance using the threaded locking screw 18. As the total length of the coaxial cannula 2 is known, the measurement device 19 can take this length into account when setting a target distance of the hydrogel outlet from the distal most face 17A of the positioning mechanism 8. The measurement device 19 may configured to be engaged and disengaged with the delivery needle 4 and positioning hub 8 for ease of use. (The significance of the distances P and X are outlined further in FIGS. 4A-4F).

FIG. 3B shows the medical device, indicated generally by the reference numeral 10, with features generally similar to those presented in FIG. 3A. The positioning mechanism 8 is comprised of two engaged parts (17, 17B) with both parts free to travel along the axis of the delivery needle 4. The movable parts (17, 17B) are shown in cross section for illustration purposes and possess a central lumen for passage of the delivery needle. The parts (17, 17B) possess a threaded engagement feature 36 and comprise a collet type assembly whereby rotation of one part relative to the other locks the positioning mechanism 8 onto the delivery needle 4 thereby restricting it's movement. The delivery needle may not possess a marker band.

Referring to FIGS. 4A-4F, the use of the device of FIGS. 3A-3B in a transthoracic biopsy procedure is illustrated.

Figure 4A:
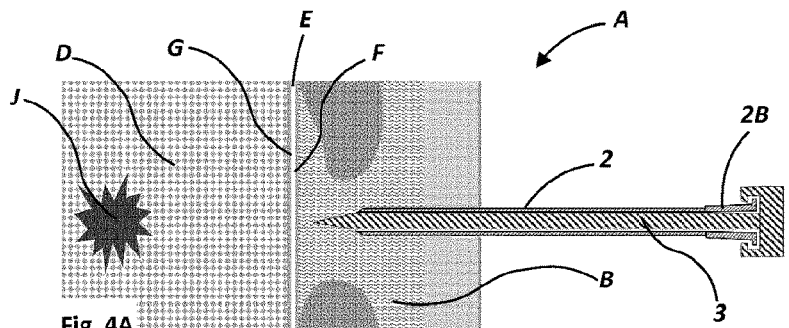
FIGS. 4A-4F. A series of lateral views illustrating a method of delivering a hydrogel plug to a target location in the lung using the delivery device.

FIG. 4A: Under imaging such as CT guidance, a coaxial cannula 2 containing a core needle 3 is aligned with a suspected lung nodule J and advanced percutaneously into the chest wall by a defined distance so that the tip of the core needle 3 is disposed in the thoracic muscle B proximal of the pleural cavity E. The required advancement distance of the needle may be determined in advance by CT imaging of the chest wall.

Figure 4B:
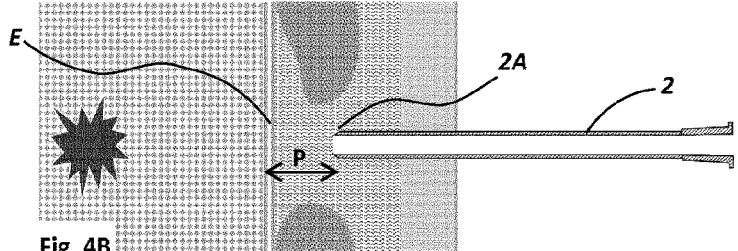

FIG. 4B: Once positioned and aligned with the target direction the core needle 3 is removed from the coaxial cannula 2, and a CT image of the chest wall is taken along the central lateral plane of the cannula 2 (see FIG. 9). Using the CT scanning software, the distance (P) from the distal-most end of the cannula 2A to the pleural cavity E is determined. This distance typically ranges from 4-20 mm. The distance P can also be measured from the distal-most end of the cannula 2A to the surface of the lung (the visceral pleura G) if it is visible in the CT scan.

Figure 4C:
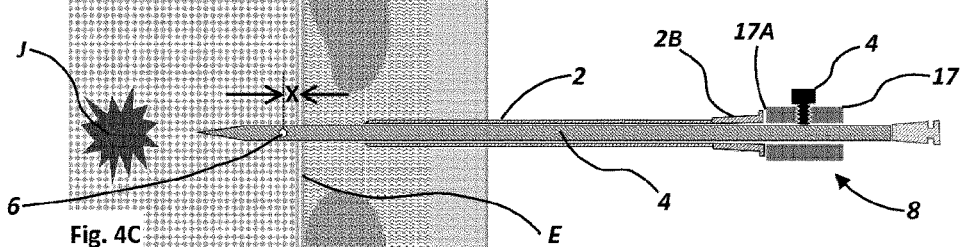

FIG. 4C: The positioning mechanism 8 of the delivery device 10 (as presented in FIG. 3A) is manually adjusted external to the coaxial cannula by moving the movable hub 17 relative to the delivery needle 4. Using the measurement device 19 as described in FIG. 3A, the distance of the hydrogel outlet 6 from the distal most face 17A of the positioning mechanism 8 can be adjusted to be equal to: ((length of coaxial cannula)+P+X), where X is the desired injection depth within the lung tissue distal to the pleural cavity E. The positioning mechanism 8 can be locked in position using the locking screw 18. Once the required injection depth has been set, the hydrogel delivery needle 4 of the medical device 10 is fully advanced through the coaxial cannula 2 until the distal-most face 17A of the movable hub 17 of the positioning mechanism 8 abuts the proximal luer lock 2B of the coaxial cannula 2. At this depth, the hydrogel outlet 6 of the delivery needle 4 is positioned a distance from the distal-most tip of the cannula 2A calculated by P+X where X is the desired injection depth within lung tissue distal to the pleural cavity E. For this particular application the desired depth within the lung tissue distal to the pleural cavity may be from 0.1-10 mm, preferably 1-3 mm.

Figure 4D:
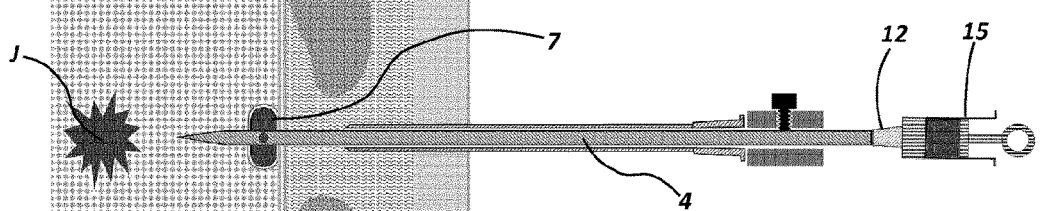

FIG. 4D: A syringe 15 with high viscosity hydrogel is attached to the device luer lock 12 and a volume of high viscosity hydrogel is injected through the delivery needle 4 and out through the hydrogel outlet 6. The viscoelastic hydrogel surrounds the needle and pushes the lung tissue out of the way to form a singular annular viscoelastic sealing plug 7 surrounding the needle. The delivery needle 4 and coaxial cannula 2 are both advanced through the viscoelastic sealing plug 7 towards and adjacent to the lung nodule J under CT guidance (step not shown).

Figure 4E:
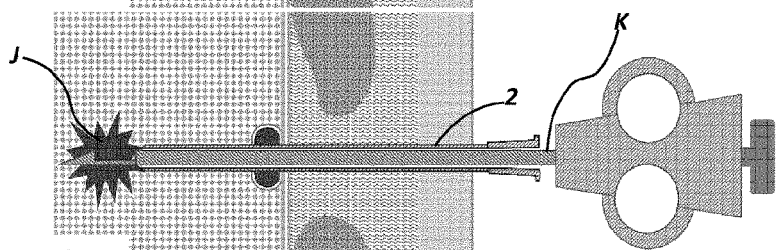

FIG. 4E: The delivery needle 4 has been removed from the coaxial cannula 2 and replaced with a core biopsy needle K so that the suspected lung nodule J can be biopsied.

Figure 4F:
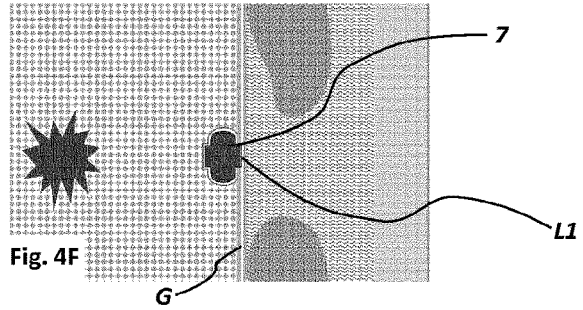

FIG. 4F: The biopsy needle K and coaxial cannula 2 are removed from the patient and the viscoelastic sealing plug 7 fills the hole L1 left by the device 10 distal of the visceral pleura G.

Figure 5A:
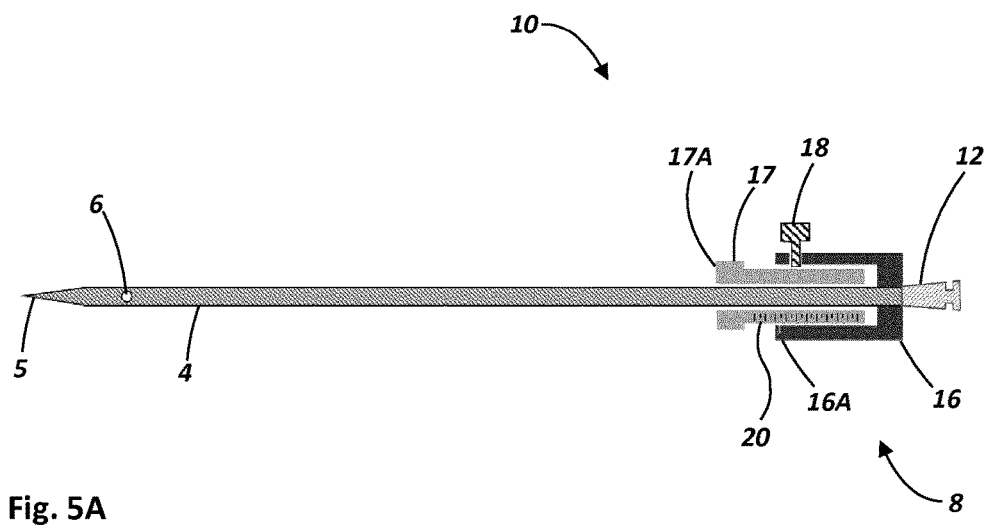
FIGS. 5A-5B. Series of lateral view illustrating embodiments of the delivery device.
Figure 5B:
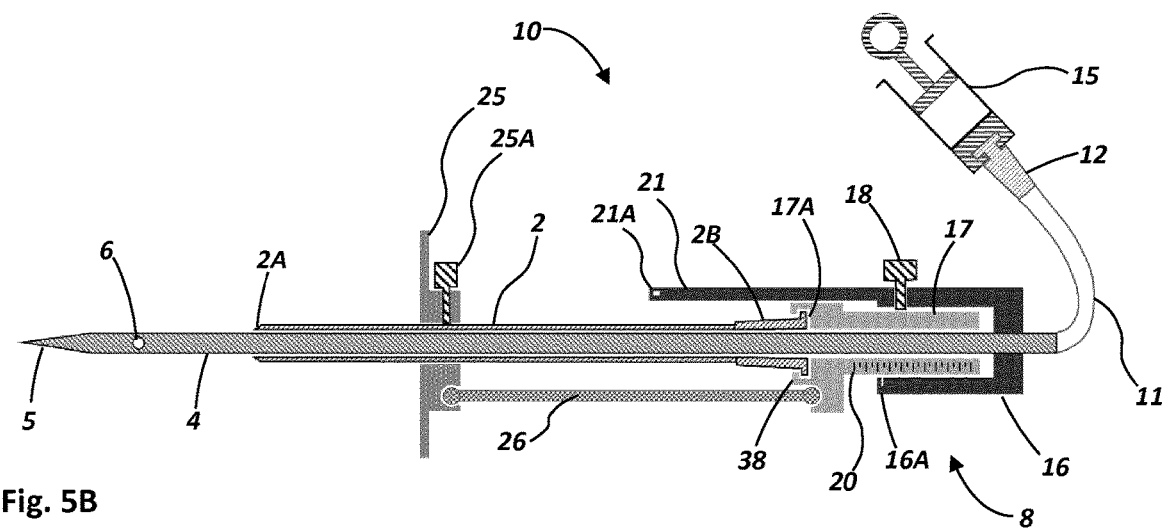

Referring to FIGS. 5A-5B, FIGS. 6A-6B and FIGS. 7A-7B, there is illustrated a medical device in which parts identified with reference to the previous embodiments are assigned the same reference numerals. FIG. 5A shows the medical device, indicated generally by the reference numeral 10, comprises a single lumen hydrogel delivery needle 4 having a distal piercing tip 5, a hydrogel outlet 6 disposed on a side of the needle proximal of the piercing tip 5, a positioning mechanism 8 disposed on a proximal end of the delivery needle 4, and a luer lock 12 at the proximal end of the delivery needle 4. The positioning mechanism 8 is mounted to the proximal side of the delivery needle 4 just distal to the luer lock 12. The components of the positioning mechanism 8 are shown in cross-sectional view for illustration purposes and include a fixed housing 16 that is bonded to the delivery needle 4, and a movable hub 17 that engages with the fixed housing 16 and is free to slide along the axis of the delivery needle 4 but is prevented from rotation and movement perpendicular to the axis of the delivery needle 4 (A detailed description of the components of the positioning mechanism 8 is presented later in FIGS. 6A-6B). A threaded locking screw 18 is provided that can be rotated and tightened to hold the position of the movable hub 17 relative to the fixed housing 16 (and the delivery needle 4). A graduated scale 20 is present on the movable hub 17 that aligns with a graduation mark or scale 16A on the fixed housing 16. (By positioning the graduated scales 20, 16A on the positioning mechanism 8, it is possible to eliminate the external measurement device 19 as described in FIG. 3A) FIG. 5B shows the medical device, indicated generally by the reference numeral 10, which comprises additional features to the device presented in FIG. 5A. The device comprises a hydrogel delivery needle 4 having a distal piercing tip 5, a hydrogel outlet 6 disposed on a side of the needle proximal of the piercing tip 5, a positioning mechanism 8 disposed on a proximal end of the delivery needle 4, and a polymer tubing 11 fluidically connected to the proximal end of the needle that terminates in a connector such as a luer lock 12 configured for attachment to a hydrogel delivery syringe 15. The delivery needle 4 is configured to be advanced through a coaxial cannula 2. The coaxial cannula is typically comprised of a single lumen stainless steel tube with a proximal luer lock 2B and is presented in cross-sectional view for illustration purposes. The delivery device 10 may also include a cannula depth lock 25 through which the coaxial cannula 2 can be inserted. The cannula depth lock 25 is a multi-part assembly that can be locked to the cannula 2 and abuts the patient's skin on its distal-most face to prevent axial movement of the cannula 2. A threaded locking screw 25A can be included with the cannula depth lock 25 that can be tightened onto the cannula 2 to hold its position relative to the cannula depth lock 25. A removable locking arm 26 is attached to the depth lock and is configured for fixing the axial position of the delivery device 10 with respect to the depth lock 25. The locking arm 26 can take the form of an narrow elongated rod or tube and can have cylindrical or spherical features at both ends that can 'snap-fit' to both the cannula depth lock 25 and the positioning mechanism 8. This enables it to be coupled and decoupled from the assembly. The device 10 may also include a polymer tubing 11 intermediate to and connecting the delivery needle 4 to the luer lock 12. The polymer tubing 11 can be made of a braided or rigid polymer tubing and be heat-set and oriented at an angle to the delivery needle 4, preferably at a right angle with the delivery needle 4. This feature provides the advantage that attachment or detachment of the syringe 15 to the luer lock 12, as well as actuation of the syringe 15 to inject the hydrogel material will not direct force along the axis of the delivery needle 4 and will thereby not greatly displace the injection depth of the hydrogel outlet 6. Referring to the positioning mechanism 8 as shown in FIG. 5B, it comprises the following features; a fixed housing 16 is attached to the hydrogel delivery needle 4, a movable hub 17 is mounted to the delivery needle 4 for axial movement along the delivery needle 4 and relative to the fixed housing 16. The movable hub 17 is configured to having a distal-most face 17A configured to abut a proximal luer lock 2B of the coaxial cannula 2. Axial movement of the fixed housing 16 relative to the movable hub 17 varies the distance that the hydrogel outlet 6 extends from the distal-most end of the coaxial cannula 2A. A series of measurement graduations 20 are provided along a surface of the movable hub 17 which align with a graduation mark 16A on the fixed housing 16 to allow a user to adjust the positioning mechanism 8 to reflect the desired hydrogel outlet 6 depth relative to the distal-most tip 2A of the coaxial cannula 2. The movable hub 17 may contain a distally disposed male luer lock 38 capable of interlocking with the proximal female luer lock 2B of the coaxial cannula 2.

Figure 6A:
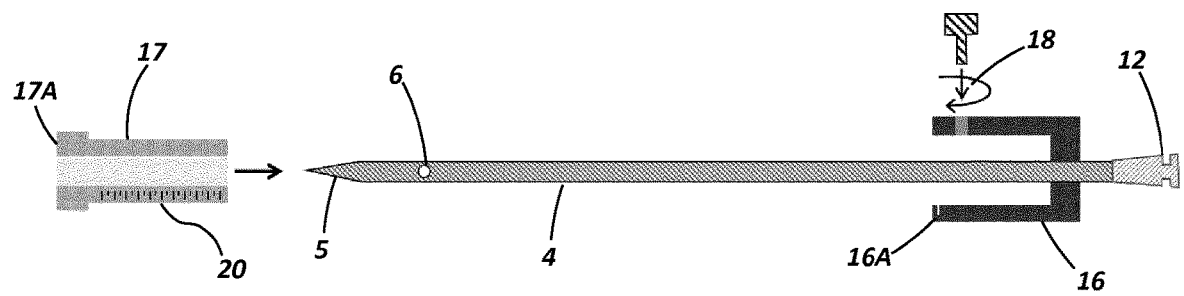
FIGS. 6A-6B. Series of lateral views showing various embodiments of the delivery device.
Figure 6B:
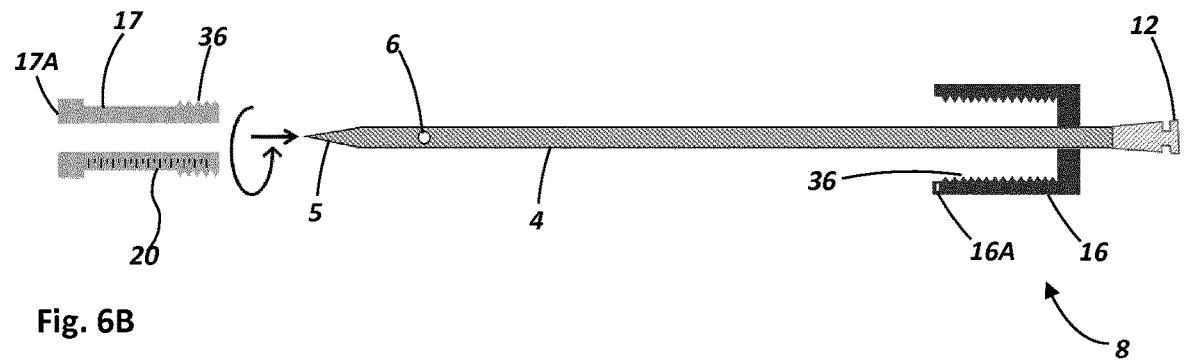

FIGS. 6A-6B presents an exploded view of components of the delivery device 10, specifically the positioning mechanism 8 and how it engages with the delivery needle 4. The components of the positioning mechanism 8 are shown in cross sectional view for illustration purposes. The positioning mechanism 8 is comprised of the fixed housing 16 which is attached to the delivery needle 4. FIG. 6A shows that the fixed housing 16 is permanently fixed or bonded to the delivery needle 4 by an adhesive, screw, weld, over-molding process or other means. The fixed housing 16 would preferably comprise an injection molded component. The movable hub 17 is free to move along the axis of the delivery needle 4 relative to the fixed housing 16. The movable hub 17 may contain a through-hole or channel to allow the delivery needle 4 to pass through it. It may also be offset from the delivery needle 4. The movable hub 17 slidably engages to overlap the fixed housing 16 through an interlocking feature. The interlocking feature can have a 'T' profile in cross-section and it prevents the displacement of the movable hub 17 in any direction except for the axial direction (along the axis of the delivery needle 4). The interlocking feature also prevents rotation of the movable hub 17. This mechanism is similar in function and form to a Vernier callipers—the movable hub 17 is axially slidable relative to the fixed housing 16. Graduation marks 16A, 20 on both the fixed housing 16 and the movable hub 17 overlap and align to provide an indication of the hydrogel outlet 6 delivery depth in relation to the distal-most face 17A of the movable hub 17. The movable hub 17 can be locked to the fixed housing 16 by a locking feature 18 which can be mounted on either the fixed housing 16 or the movable hub 17. The locking feature 18 can also comprise a collet style mechanism or other means of restricting movement between the fixed housing 16 and movable hub 17. In an additional embodiment it is also suitable to temporarily attach the fixed housing 16 to the delivery needle 4. Temporarily attaching the fixed housing 16 to the delivery needle 4 may be achieved with an additional mechanism such as a tightening screw or collet.

FIG. 6B shows an embodiment of the positioning mechanism 8 whereby both fixed housing 16 and movable hub 17 comprise cylindrical or tubular type structures that are configured to engage with each other along the axis of the delivery needle 4. Both structures contain an inner lumen through which the delivery needle 4 passes. Again, the parts of the positioning mechanism 8, namely the fixed housing 16 and movable hub 17 are shown in cross-section for illustration purposes. The fixed housing 16 and movable hub 17 both possess a threaded engagement feature 36 (forming a series of precisely spaced series of circumferential notches) whereby rotation of the movable hub 17 relative to the fixed housing 16 effects relative axial movement of the parts along the delivery needle 4. Rotation of the movable hub 17 relative to the fixed housing 16 alters the distance of the hydrogel outlet 6 from the distal-most face 17A of the movable hub 17. The threaded engagement feature 36 can be positioned on either the internal or external surfaces of both part, but typically the location will be opposite between parts for engagement purposes. This positioning mechanism 8 may not require a locking mechanism 18 to hold the axial position of the delivery needle 4 due to the interlocking of the threaded engagement feature 36 but it is also possible to include a locking feature with this assembly. Graduation marks 16A, 20 on both the fixed housing 16 and the movable hub 17 overlap and align to provide an indication of the hydrogel outlet 6 delivery depth in relation to the distal-most face 17A of the movable hub 17.

Figure 7A:
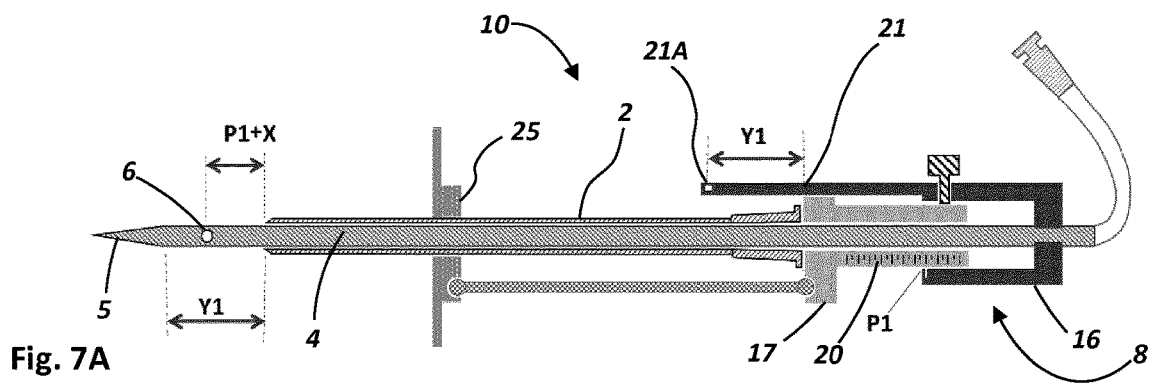
FIGS. 7A-7B. Series of lateral views illustrating different positioning configurations of the delivery device.
Figure 7B:
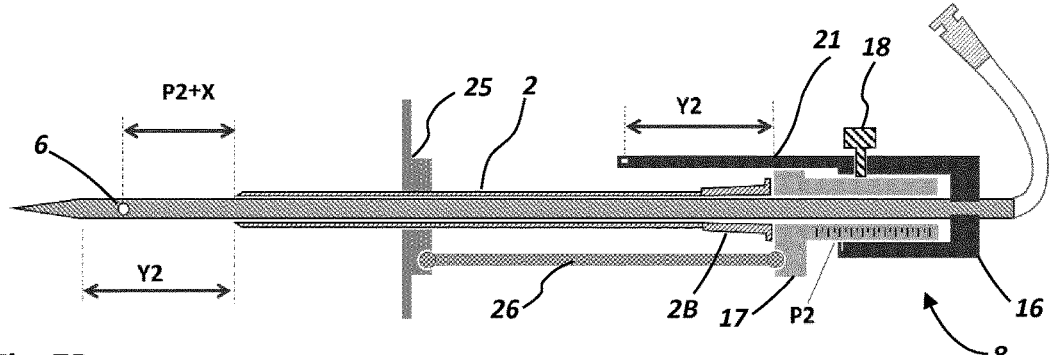

FIGS. 7A-7B presents two different position depths for the positioning mechanism 8 and demonstrates how the positioning mechanism 8 is configured for axial adjustment so that it can vary the distance the delivery needle hydrogel outlet 6 extends from the coaxial cannula 2. For example, from a first configuration as presented in FIG. 7A in which the hydrogel outlet 6 is spaced a first distance P1+X from the distal-most end of the cannula 2A, to a second configuration as presented in FIG. 7B in which the hydrogel outlet 6 is spaced a second distance P2+X from the distal-most end of the cannula 2A in which case P2>P1. It is evident that the movable hub 17 will more fully engage and overlap the fixed housing when the value of P is greater. The positioning mechanism 8 may also include a cannula depth guide 21 and optional depth marking 21A at its distal end which provides an indication of the depth the coaxial cannula 2 is to be advanced over the delivery needle 4 such that the distal-most end of the cannula 2A is positioned just proximal to the needle tip 5. The cannula depth guide 21 comprises an extension arm 21 mounted to the fixed housing 16 for movement therewith that extends distally over the proximal female luer lock of the cannula 2B by a distance of Y1 in FIG. 7A and Y2 in FIG. 7B. The extension arm of the cannula depth guide 21 is designed to extend outside of, and be narrower than the proximal luer lock 2B of the cannula 2 so that it does not interfere with handling and advancement of the proximal luer lock 2B and cannula 2. The depth marking 21A can include a visual aid such as a contrasting colour mark or a physical indentation of the extension arm 21 to amplify its depth marking capability. The positioning mechanism is configured so that movement of the delivery needle 4 and fixed housing 16 with respect to the movable hub 17 proportionally adjusts the cannula depth guide 21. Thus, referring to FIG. 7A, when the positioning mechanism 8 is adjusted to advance the delivery needle 4 through the cannula 2 by a distance of P1, the cannula depth guide 21 is adjusted to indicate a depth of Y1. Likewise, in FIG. 7B, when the positioning mechanism 8 is adjusted to advance the delivery needle 4 through the coaxial cannula 2 by a distance of P2—greater than P1—the cannula depth guide 21 is adjusted to indicate a depth of Y2 which is proportionally greater than Y1.

Referring to FIGS. 8A-8H, the use of the device of FIGS. 5A-5B, FIGS. 6A-6B and FIGS. 7A-7B in a transthoracic biopsy procedure is illustrated.

FIG. 8A: Under CT guidance, a coaxial cannula 2 containing a core needle 3 is aligned with a suspected lung nodule J and advanced percutaneously into the chest wall by a defined distance so that the tip of the core needle 3 is disposed in the thoracic muscle B proximal of the pleural cavity E. The advancement distance of the needle may be determined in advance by CT imaging of the chest wall. Once positioned and aligned with the target direction, the cannula depth lock 25 is moved axially along the cannula to a position where it abuts the patient's skin O, and is locked to the cannula 2 in this position by tightening a screw that is integral to the cannula depth lock 25 (not shown). If sufficient traction between the coaxial cannula 2 and surrounding tissue is present, locking to the depth lock 25 may not be required.

FIG. 8B: The core needle 3 is removed from the coaxial cannula 2, and a CT image of the chest wall is taken along the central lateral plane of the cannula 2 (see FIG. 9). Using the CT scanning software, the distance (P) from the distal-most end of the cannula 2A to the pleural cavity E is determined. This distance typically ranges from 4-20 mm. The distance P can also be measured from the distal-most end of the cannula 2A to the surface of the lung (the visceral pleura G) if it is visible in the CT scan.

FIG. 8C: The positioning mechanism 8 of the delivery device 10 (as presented in FIG. 5A) is manually adjusted by moving the movable hub 17 relative to the fixed housing 16 so that the graduation mark 16A lines up with the distance P (as previously measured) on the graduated scale 20. The positioning mechanism 8 can be locked in position using locking feature 18 if locking is required. The hydrogel delivery needle 4 of the medical device 10 is fully advanced through the coaxial cannula 2 until the distal-most face 17A of the movable hub 17 of the positioning mechanism 8 abuts the proximal luer lock 2B of the coaxial cannula 2. At this depth, the hydrogel outlet 6 of the delivery needle 4 is positioned a distance from the distal-most tip of the cannula 2A calculated by P+X where X is the desired injection depth within lung tissue distal to the pleural cavity E. For this particular application the desired depth within the lung tissue distal to the pleural cavity is from 0.1-6 mm, preferably 1-3 mm.

FIG. 8D: The removable locking arm 26 is fixed in position between the cannula depth lock 25 and movable hub 17 of the positioning mechanism, thereby fixing the depth of the needle 4. A syringe 15 with viscoelastic hydrogel is attached to the device luer lock 12 and a volume of viscoelastic hydrogel is injected through the delivery needle 4 and out through the hydrogel outlet 6. The viscoelastic hydrogel surrounds the needle and pushes the lung tissue out of the way to form a singular annular viscoelastic sealing plug 7 surrounding the needle.

FIG. 8E: The cannula depth lock 25 is loosened to allow movement of the cannula 2. The cannula 2 is advanced over the delivery needle 4 to a depth indicated by the cannula depth indicatory 21A, at which position the distal-most end of the cannula 2A is advanced through the sealing plug 7 to just before the distal tip 5 of the delivery needle 4 and also covering the hydrogel outlet 6 on the needle. At this point, the closed annular sealing plug 7 forms a seal around the cannula 2.

FIG. 8F: The locking arm 26 is detached from the cannula depth lock 25 and the delivery device 10 is retracted from the cannula 2. It is replaced with the core needle 3 which can be attached to the luer lock 2B of the cannula 2.

FIG. 8G: The core needle 3 and cannula 2 are advanced to the suspected lung nodule J through the sealing plug 7. Again, this step is performed under CT guidance. The core needle 3 is removed from the cannula 2 and the core biopsy needle K (or alternatively a fine needle aspiration needle) is advanced through the cannula and a biopsy of the suspected lung nodule J is performed through the cannula 2.

FIG. 8H: The biopsy needle K and coaxial cannula 2 are removed from the patient and the viscoelastic sealing plug 7 fills the hole L1 left by the device 10 distal of the visceral pleura G.

Figure 9:
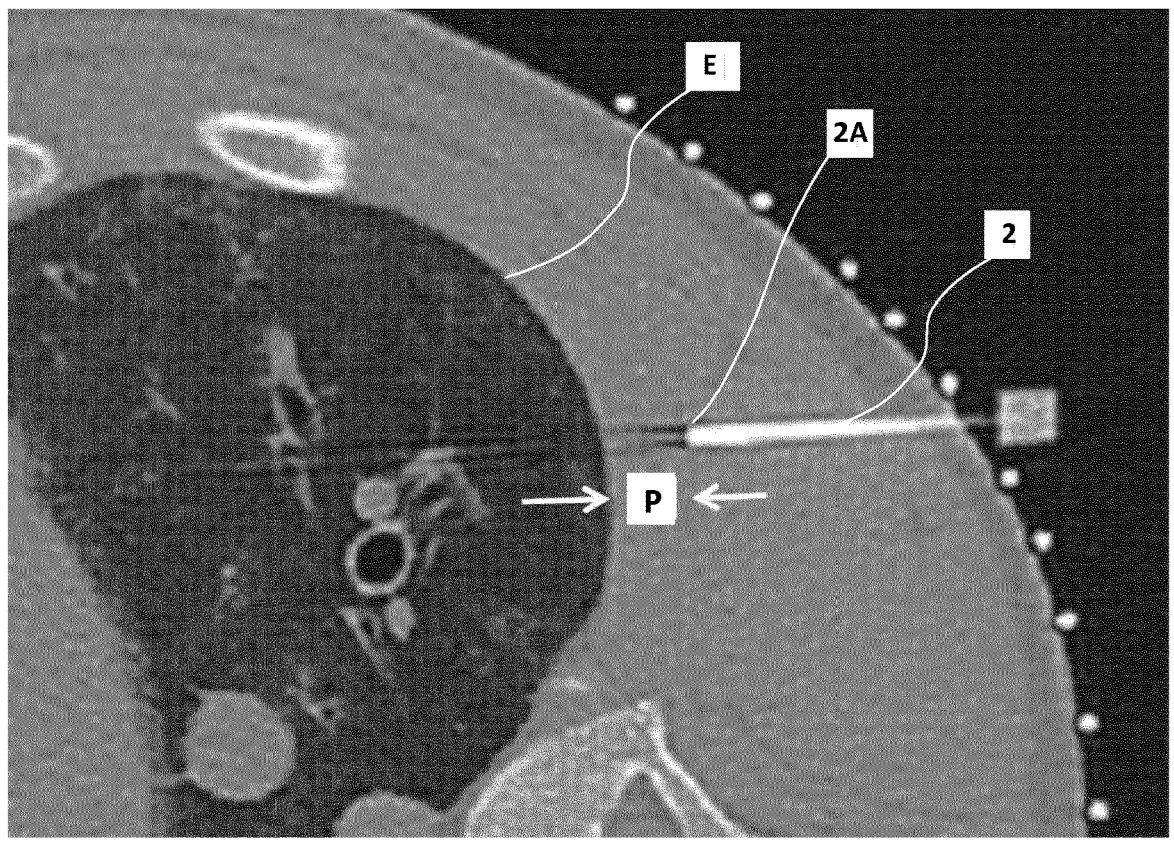
FIG. 9. A section of a CT Scan showing a coaxial cannula in the chest wall proximal to the pleural cavity in a pig.

FIG. 9 is a partial section of an image from a CT scan showing alignment of the coaxial cannula 2 in the chest wall towards an intended biopsy site. The core needle has been removed from the coaxial cannula 2 as previously described in FIG. 8B so that a flat edge is visible at the distal tip 2A of the coaxial cannula 2. The CT scan is taken perpendicular to the central axis of the coaxial cannula 2. The pleural cavity E is easily defined as the boundary of the dark region—the lung, and the grey region—the chest wall. Using the CT scanner software, the distance P—from the distal-most tip of the coaxial cannula to the centre of pleural cavity E—can be determined. The flat edge of the distal tip 2A of the coaxial cannula 2 enables an accurate distance P to be determined. On other occasions, when the pleural cavity E gap is increased so that the physical gap (typically >0.5 mm) is more noticeable by a black band or space around the lung, it may be possible to identify the surface of the lung (the visceral pleura) from the surface of the chest wall (the parietal pleura). On these occasions, it is more appropriate to measure the distance P to the surface of the lung (the organ). The surface of the lung can also be referred to as the visceral pleura.

Figure 10:
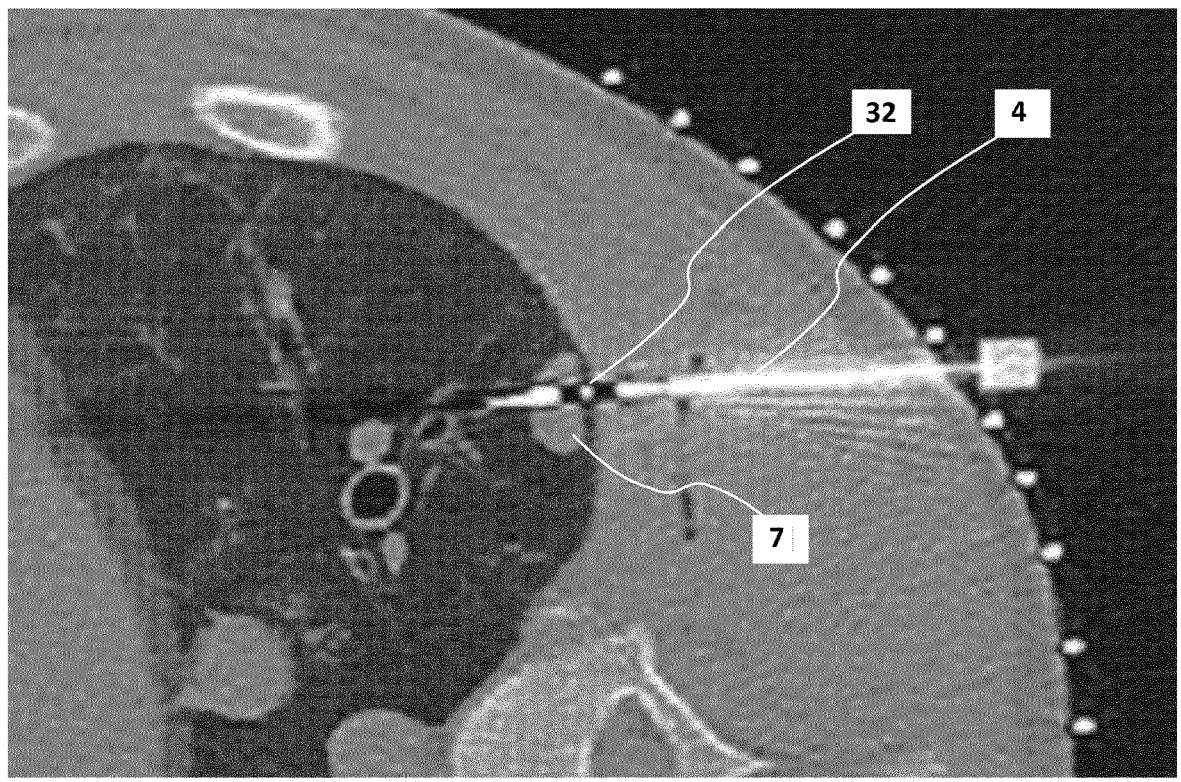
FIG. 10. A section of a CT-Scan showing a delivery needle and injected hydrogel plug in the lung of a pig.

FIG. 10 is a section of a CT-Scan showing an 18G hydrogel delivery needle 4 having delivered a hydrogel plug 7 to the periphery of the lung beneath the visceral pleura G pre-biopsy in a porcine in vivo study. The pig weight was approximately 30 kg and the viscous plug comprised of approximately 500 µl of 50 mg/ml sodium hyaluronate in water with the sodium hyaluronate having an average molecular weight of 1.8-2 MDa. This hydrogel delivery needle 4 is constructed radiolucent sections and a radiopaque marker band 32 to aid in the identification of the location of the hydrogel outlet 6 in relation to the pleural cavity or the surface of the lung.

Figure 11A:
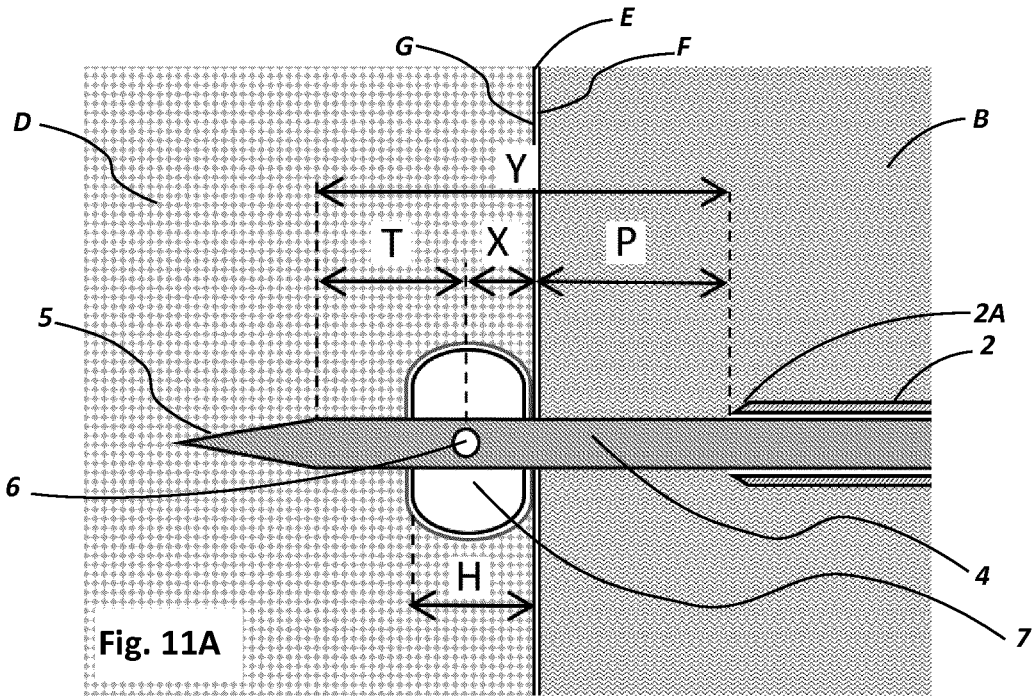
FIGS. 11A-11B. Lateral views of the hydrogel plug position in relation to different embodiments of the delivery device and the pleural cavity.

FIG. 11A is a detailed schematic illustration of the hydrogel delivery needle 4 in-situ in the patient after delivering the hydrogel plug 7. The distal-most tip 2A of the coaxial cannula 2 is positioned a distance P from the pleural cavity in the thoracic wall B. Typical distances for P are 3-20 mm.

In other instances and for other surgical procedures, for example when targeting different organs, P can represent the distance from the distal-most tip of the coaxial cannula to any tissue interface, body cavity, organ or vessel exterior surface.

The delivery needle 4 is inserted through the coaxial cannula 2 into the lung tissue D. The hydrogel outlet 6 is positioned a distance X distal of the pleural cavity E, or a distance P+X from the distal-most tip of the coaxial cannula 2A. Typical distances for X are 0.1-6 mm, preferably 1-4 mm, The hydrogel outlet 6 is also located a distance T from the proximal side of the needle piercing tip 5, equivalent to the proximal side of the ground region of the piercing needle tip. Typical distances for T are 0.5-15 mm, preferably 1-7 mm.

The distal-most tip 2A of the coaxial cannula 2 is positioned a distance Y from proximal side of the needle tip 5 equivalent to the proximal side of the ground region of the needle tip. The total distance for Y≈P+X+T.

There are a number of advantages of having the hydrogel outlet 6 located a distance from the needle tip 5 in relation to procedures requiring transthoracic needle access. If the hydrogel outlet 6 was at the end of a conventional needle with bevel point tip, the sharp point of the needle would lie very close to the visceral pleura and periphery of the lung in order to deliver the hydrogel plug to the correct position. During this time, there would be a high chance that the sharp bevel tip could lacerate the visceral pleura and lung tissue which is constantly moving due to respiration. It is therefore necessary to position the sharp needle tip some distance from the visceral pleura E. Additionally, having the hydrogel outlet 6 a distance from the distal tip 5 also has the advantage of creating a uniform and concentric gel plug 7 seal around the delivery needle 4.

Figure 11B:
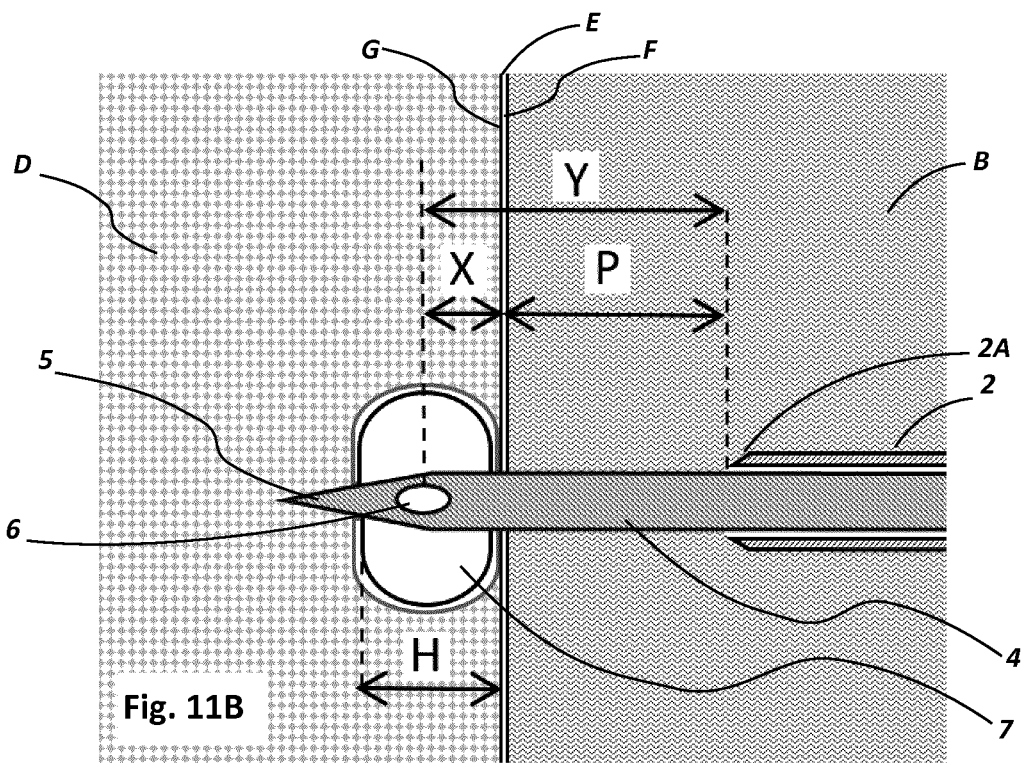

FIG. 11B shows another embodiment which can be included in any of the embodiments presented herein. In this embodiment the hydrogel outlet 6 is positioned at the distal-most tip 5 of the delivery needle 4 and can be formed through a standard multi-bevel grind or similar. For this scenario Y≈P+X FIGS. 12A-12C are images of an excised and ethanol fixed lung tissue section after injection of a hydrogel plug during a percutaneous biopsy procedure. The injected hydrogel plug consists of 500 µl of 50 mg/ml sodium hyaluronate in water with the sodium hyaluronate having an average molecular weight of 1.8-2 MDa. The gel has been created with 5% India ink stain in water for visualisation purposes. FIG. 12A shows the gel plug visible under the surface of the lung (surrounded by a dashed circle). In FIG. 12B the section has been dissected along the mid plane of the gel plug using a scalpel. FIG. 12C shows a close-up view of the dissected gel plug. The fixing process has left the gel plug largely intact. It is evident that the gel plug forms a singular body of material. There is a clear demarcation between the lung tissue and the plug implying that the viscous gel material does not infuse into the lung tissue either at the point of injection or at any point during or after the procedure.

FIGS. 13A1-13B2 illustrates a medical device according to an additional embodiment of the invention, indicated generally by the reference numeral 70, and in which parts identified with reference to the previous embodiment of FIGS. 8A-8H are assigned the same reference numerals. This embodiment is similar to the embodiment of FIGS. 8A-8H but has an alternative cannula depth guide provided by a cannula extension member 31 having a distal-most end 31A that abuts the proximal luer lock of the cannula 2B and a proximal end 31B that extends proximal to the fixed housing 16 of the positioning mechanism 8. The cannula extension member 31 is a body with central slot or lumen to accommodate the central passage of the delivery needle 4. It is coaxially mounted on the delivery needle 4 for axial movement relative to the delivery needle and positioning mechanism 8. The cannula extension member 31 also comprises an axially elongated slot to allow coupling between the fixed housing 16 and the delivery needle 4. In the first position shown in FIG. 13A1 the distal-most end of the cannula extension member 31A is in line with the distal-most end of the movable hub 17A. A snap fit or interference features at the distal end of the cannula extension feature 31A may hold it to the distal-most end of the movable hub 17A. In this position the proximal end of the cannula extension member 31B is spaced a distance Y1 from the fixed housing 16. In the second position shown in FIG. 13A2, the cannula extension member 31 has been advanced forward so that it pushes the cannula 2 forward. In its most forward position the proximal end 31B abuts the proximal-most end of the fixed housing 16. In this position, the distal-most end of the cannula 2A covers the delivery needle 4 and hydrogel outlet 6, up to but not covering its piercing distal tip 5. As illustrated in FIG. 13G1, the positioning mechanism 8 is adjusted by moving the movable hub 17 relative to the fixed housing 16 so that the delivery needle 4 is moved distally through the coaxial cannula 2 to distance P2 as indicated on the graduation scale 20 (where P2>P1). At position P2, the separation between the movable hub 17 and the distal-most end of the cannula extension member 31B increases proportionally to a distance of Y2 (where Y2>Y1). In the second position shown in FIG. 13B2, the cannula extension member 31 has been advanced forward so that it pushes the cannula 2 forward. In its most forward position the proximal end 31B abuts the distal-most end of the fixed housing 16. In this position, the distal-most end of the cannula 2A covers the delivery needle 4 and hydrogel outlet 6, up to but not covering its piercing distal tip 5. The mechanism described in FIGS. 13A-13B acts as a depth guide to allow the user to advance the cannula 2 to the correct position where the distal-most end of the cannula 2A is located at the needle tip 5 and covers the hydrogel outlet 6 without physically touching the cannula 2.

FIGS. 14A-14H illustrates a method of using the device of FIGS. 13A-13B which is substantially the same as the method described with reference to FIGS. 8A-8H. The following is a description of this procedure.

Figure 14A:
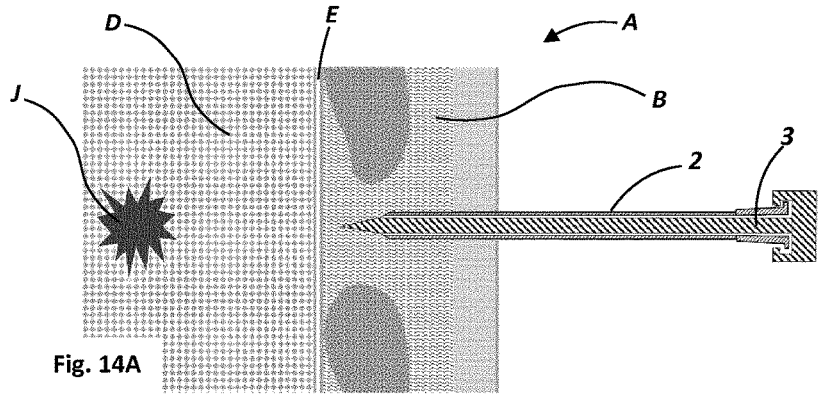

FIG. 14A: Under CT guidance, a coaxial cannula 2 containing a core needle 3 is aligned with a suspected lung nodule J and advanced percutaneously into the chest wall by a defined distance so that the tip of the needle is disposed in the thoracic muscle B proximal of the pleural cavity E.

Figure 14B:
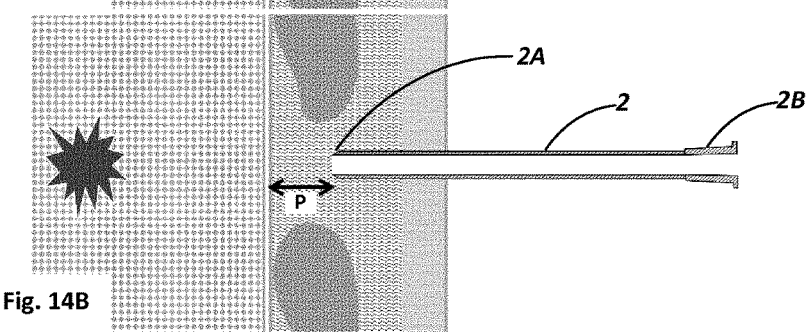

FIG. 14B: The core needle 3 is removed from the coaxial cannula 2, and a CT image of the chest wall is taken along the central lateral plane of the coaxial cannula 2. Using the CT scanning software, the distance (P) from the distal-most end of the cannula 2A to the pleural cavity E is determined.

Figure 14C:
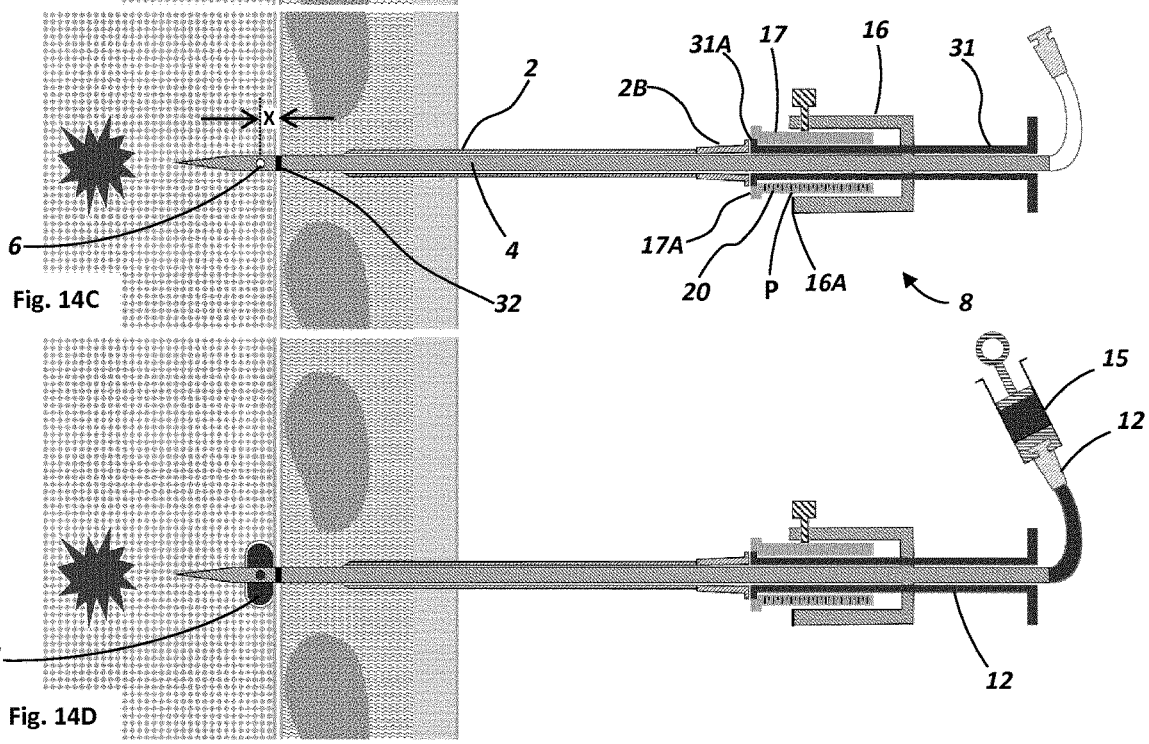

FIG. 14C: The positioning mechanism 8 of the delivery device 10 (as presented in FIG. 13A1) is adjusted by moving the movable hub 17 relative to the fixed housing 16 so that the graduation mark 16A lines up with the distance P (as previously measured) on the graduated scale 20. The hydrogel delivery needle 4 of the device 70 is fully advanced through the coaxial cannula 2 until the distal-most face 17A of the movable hub 17 abuts the proximal luer lock 2B of the coaxial cannula 2. The distal most face 31A of the cannula extension member 31 also abuts the proximal luer lock 2B. At this depth, the hydrogel outlet 6 of the delivery needle 4 is positioned a distance from the end of the cannula calculated by P+X. This equates to the desired depth of injection for the hydrogel outlet 6 within the lung tissue distal of the pleural cavity E. The positioning of a radiopaque marker band 32 attached to the delivery needle 4 in relation to the pleural cavity E can be used to make adjustments to the final depth of the hydrogel outlet 6 if required. This would be achieved by aligning the marker band 32 with the pleural cavity E.

Figure 14D:
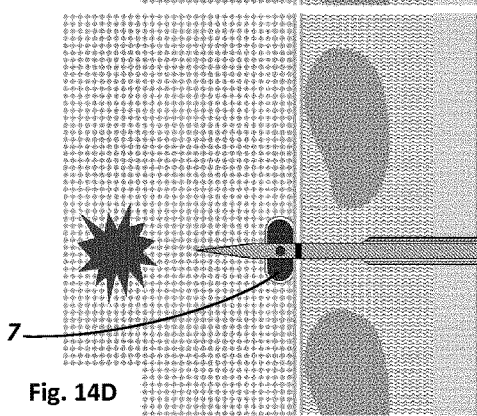

FIG. 14D: A syringe 15 filled with hydrogel material is attached to the device luer lock 12 and a volume of hydrogel is injected through the delivery needle 4 and out through the hydrogel outlet 6 at the target depth X, distal to the pleural cavity E in the lung. The viscoelastic hydrogel surrounds the needle and pushes the tissue out of the way to form a single closed annular viscoelastic sealing plug 7 surrounding the needle.

FIG. 14E: The entire medical device assembly 10, including the coaxial cannula 2 and delivery needle 4 with positioning mechanism 8 are advanced in unison towards the target biopsy lesion J under CT guidance. The piercing needle tip 5 is positioned adjacent to or in the lung nodule J. (During this process, a mechanism can be provided to engage the female luer lock 2B of the coaxial cannula 2 with a male luer lock at the distal end of the positioning mechanism 8—not shown).

FIG. 14F: The cannula extension member 31 is advanced so that its proximal end 31B abuts the proximal face of the fixed housing 16 of the positioning mechanism 8. As the cannula extension member 31 extends through the positioning mechanism 8, its distal-most end 31A abuts the cannula luer lock 2B and pushes the cannula 2 forward a predetermined distance. This results in the distal-most tip 2A of the coaxial cannula 2 being positioned just before the piercing needle tip 5 of the delivery needle 4 and covering the hydrogel outlet 6. This step is desirable as it positions the cannula distal-most tip 2A so that it is adjacent to or within the lung nodule J to be biopsied. These steps achieves the repositioning of the coaxial cannula 2 within the nodule J without any additional need for measurements from the CT-scanner.

FIG. 14G: The delivery device 70 has now been removed from the coaxial needle 2 and replaced with a biopsy needle K (in this case a core biopsy needle) to perform a biopsy of the lung nodule J.

FIG. 14H: The biopsy needle K and coaxial cannula 2 are both removed from the patient and the viscoelastic sealing plug 7 fills the hole L1 left by the device 10 distal of the visceral pleura G.

Figure 15A:
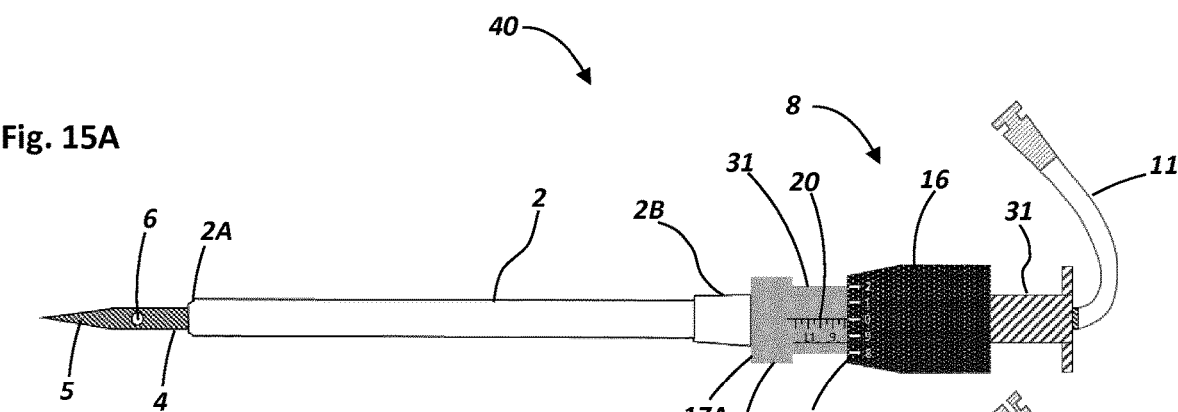
FIGS. 15A-15C. A series of lateral views illustrating an embodiment of the delivery device with threaded positioning mechanism.
Figure 15B:
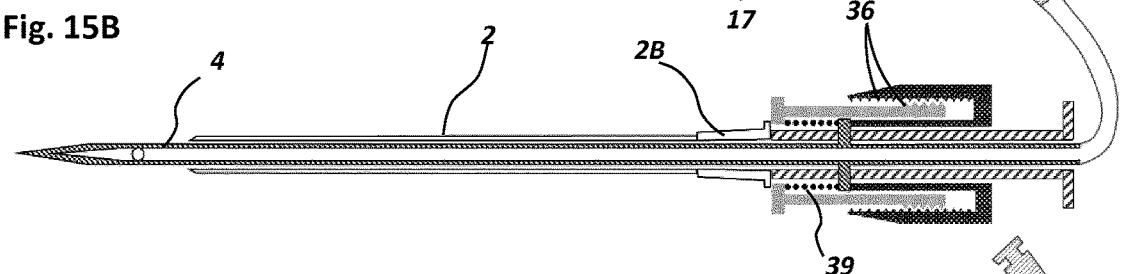
Figure 15C:
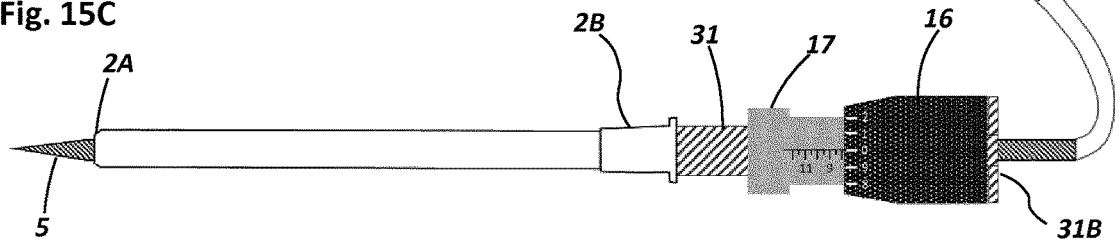

FIGS. 15A-15C illustrates an embodiment of the medical device which can be incorporated in any embodiment of the invention, indicated generally by the reference numeral 40, and in which parts identified with reference to the previous embodiment of FIGS. 13A-13B are assigned the same reference numerals. This embodiment can be used with any of the devices described herein and is similar to the embodiment of FIGS. 13A-13B except that the fixed housing 16 and movable hub 17 of the positioning mechanism 8 are provided with a threaded engagement feature 36 whereby rotation of the fixed housing 16 relative to the movable hub 17 effects relative axial movement of the parts, similar to a micrometer device. FIG. 15A shows an image of the device 40 with the cannula extension member 31 in a first position so that the proximal luer lock 2B of the coaxial cannula 2 abuts the distal-most face of the movable hub 17A. The distal-most face of the cannula extension member 31 is also in line with the distal-most face of the movable hub 17A. A graduated scale 20 is provided on the movable hub 17 and graduation marks 16A are also provided on the fixed housing 16. The coaxial cannula 2 is not shown in cross-section. FIG. 15B shows a cross-sectional view of the device 40 of FIG. 15A. A threaded engagement feature 36 disposed on the internal face of the fixed housing 16 and the external face of the movable hub 17 is visible. A spring 39 is provided to keep the delivery needle 4 abutting the fixed housing 16 of the positioning mechanism 8. The spring 39 also helps to eliminate any backlash in the threaded mechanism. The spring 39 also acts to provide a resistance to overcome in rotation of the fixed housing 16 relative to the movable hub 17. FIG. 15C shows an image of the device 40 with the cannula extension member 31 in a second position so that the coaxial cannula 2 has been advanced to the piercing distal tip 5 of the delivery needle 4 by advancing the cannula extension member 31 to its most forward position so that the proximal end 31B abuts the proximal-most end of the fixed housing 16

Figure 16:
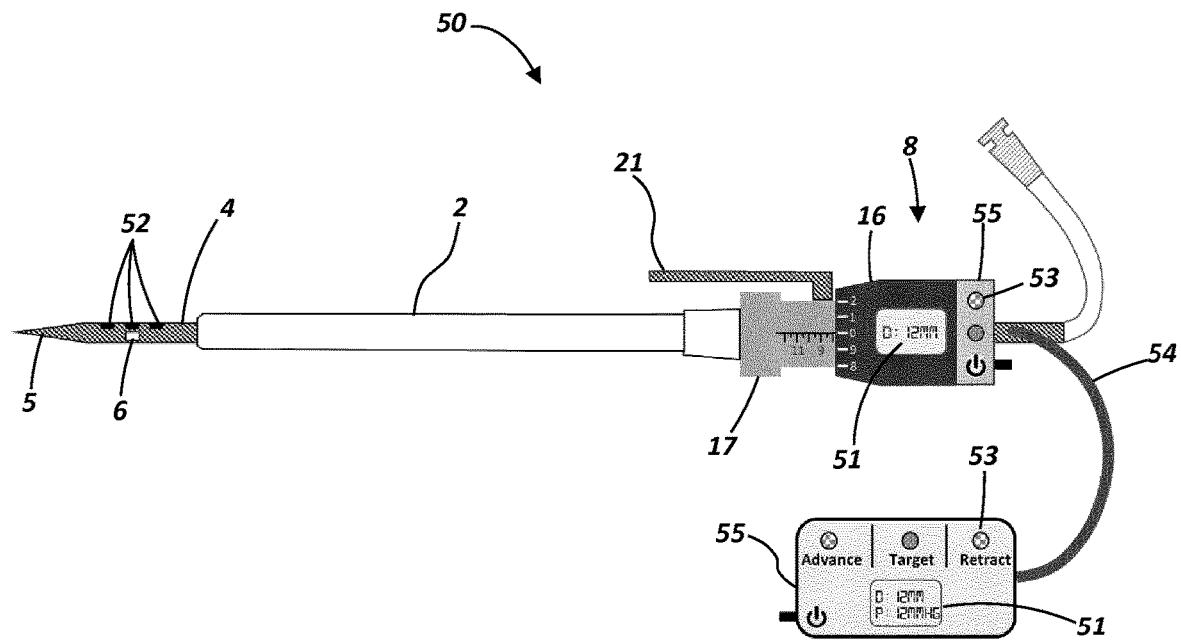
FIG. 16. A lateral view of an embodiment of the delivery device with electronic positioning and measurement features and indicators.

FIG. 16 illustrates a medical device according to an additional embodiment of the invention, indicated generally by the reference numeral 50, and in which parts identified with reference to the previous embodiment of FIGS. 8A-8H are assigned the same reference numerals. This embodiment is similar to the embodiment of FIGS. 8A-8H but additionally incorporates a digital depth gauge 51 and sensors 52 used to detect and comparing surrounding tissue properties as a means of positioning the hydrogel outlet 6 relative to the pleural cavity and chest wall. The property (parameter) measured by the sensors may be electrical, chemical, optical, acoustic, mechanical and thermal. Tissue electrical parameters may include bioimpedance, capacitance, and resistance. Tissue chemical parameters may include pH level, blood concentration and temperature. Optical properties can include radio-translucency and response to light. Mechanical properties can include stiffness, compliance, strength and elasticity. Thermal properties can include thermal conductivity and temperature. The sensors employed herein may be configured to detect a parameter of tissue. The following terms can be used interchangeably with "sensor": "transducer", "transmitter", "switch", "transistor" and "actuator". Various types of sensors are envisaged for use with the delivery device described herein. Sensors may or may not require an external power source to operate. The sensor may be an integrated sensor, having signal emission and signal detection modules. The sensor may also comprise separate signal emission and detection modules that may be disposed adjacent to each other, circumferentially around the needle, or axially along the needle, or any other disposition. The sensor may comprise an electronic sensor and may be configured to detect an electrical property of tissue, a mechanical property of tissue or a chemical property of tissue. The sensors may be external to the delivery needle 4, or encapsulated within the delivery needle 4. The sensors may consist of pressure sensors, for example MEMS based pressure sensors configured to detect the force exerted by the surrounding tissue onto the needle as the needle is being inserted through the tissue and towards the target site. An electronic control unit and user interface 55 can be provided with the device, either as part of the positioning mechanism 8 or external to the positioning mechanism and attached via an electronic cable 54. The electronic control unit and user interface 55 may be battery powered or charged with an external power source. LED lights 53 and an electronic display 51 can be provided on the user interface 55 to confer depth and tissue properties to the clinician. The sensors may also be used for diagnostic purposes at the target site, for example to differentiate malignant tissue from healthy tissue. The digital depth gauge 51 and/or the sensors 52 and additional features presented in FIG. 16 may optionally be used in any of the embodiments disclosed herein. The sensors 52 may also be replaced and/or combined with heating or cooling elements to provide a therapeutic effect. For example, radiofrequency, ultrasound or microwave ablation electrodes can be incorporated into the delivery needle 4. Other elements such as coiled electrodes, magnetic electrodes, and other energy delivery elements can be included in the device.

Figure 17:
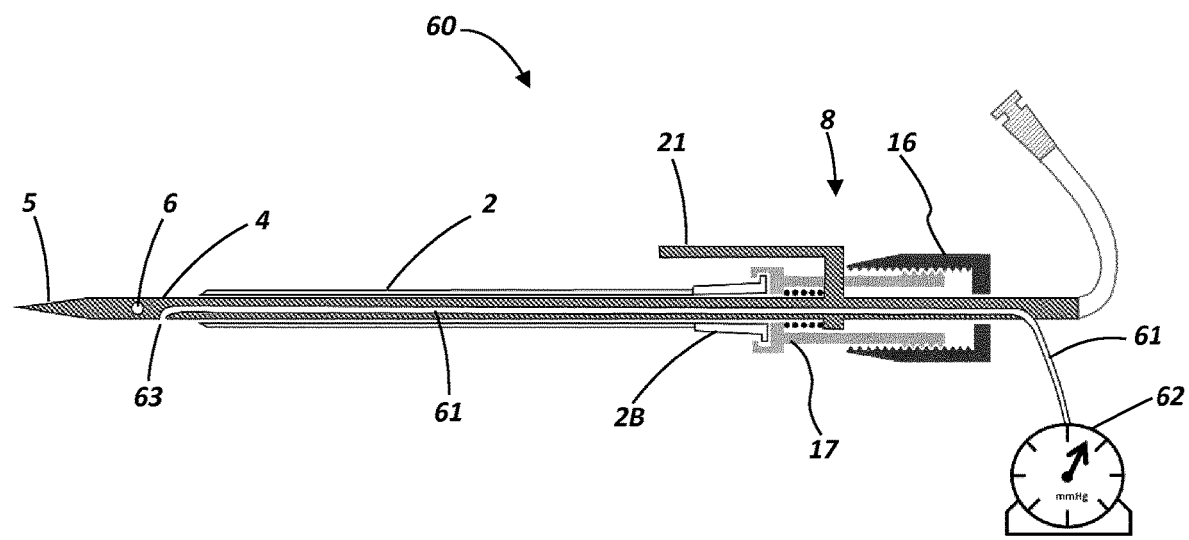
FIG. 17. A lateral view of an embodiment of the delivery device with a pleural pressure measurement and display feature.

FIG. 17 illustrates a medical device according to an additional embodiment of the invention, indicated generally by the reference numeral 60, and in which parts identified with reference to the previous embodiment of FIGS. 8A-8H are assigned the same reference numerals. This embodiment is similar to the embodiment of FIGS. 8A-8H but includes a channel 61 and side port 63 at the distal-most end of the delivery needle 4 for pleural pressure measurement as a means of positioning the hydrogel outlet 6 relative to the pleural cavity. The channel 61 may take the form of a tube which may be internal or external to the delivery needle 4. The channel is attached to a pressure gauge 62 at the proximal end of the device. The pressure gauge 62 may be mechanical or electronic in nature and lie either internal or external to the positioning mechanism 8. These features may be used with any embodiment of the device and system described herein.

Figure 18A:
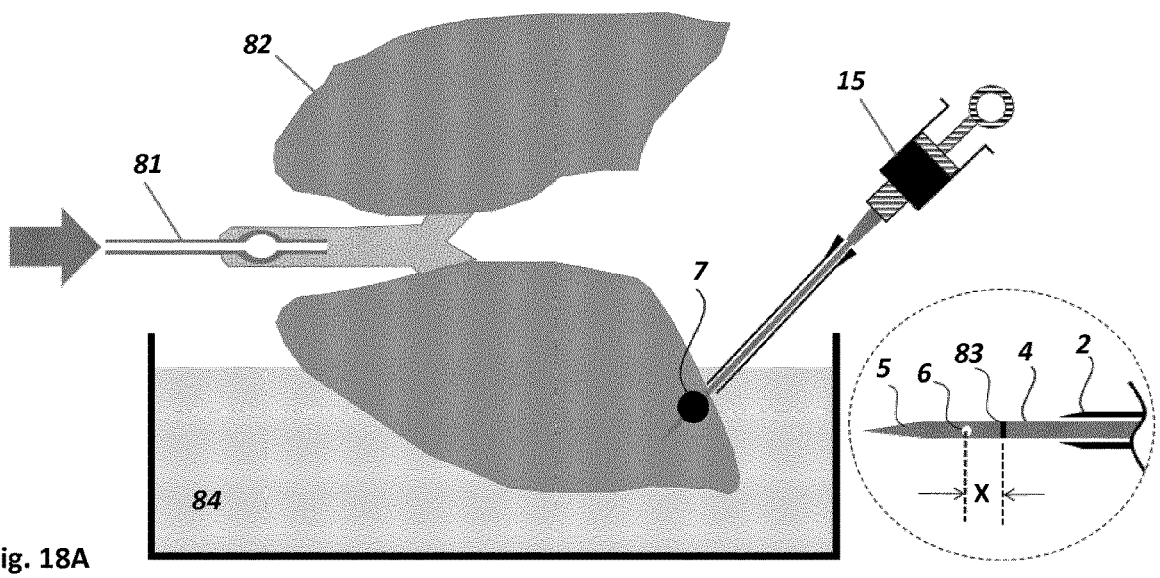
FIGS. 18A-18E. Experimental set-up and results from a series of experiments to evaluate the efficacy of different features of the hydrogel plug.

Without being bound to any theory, FIGS. 18A-18E presents ex vivo study results of variables believed to be desirable to the efficacy of the hydrogel plug seal described herein. FIG. 18A illustrates the experimental set up. An 18G hydrogel delivery needle 4 with 17 G coaxial needle 2, similar in style to the one presented in FIG. 2B was prepared for this study. To determine depth of injection through the hydrogel outlet 6 inside the surface of the lung 82, a visible black line 83 was marked on the external surface of the 18 G delivery needle 4 at a known distance from the hydrogel outlet 6. This line was visually aligned with the surface of the lung to target an injection depth X. Adult (80-120 kg pigs) porcine lungs 82 were procured from a local abattoir and connected to positive pressure ventilation of 11 $cmH_2O$ through an intubation tube 81. Pressure was consistent for all studies conducted. For all tests, a 1 ml syringe 15 comprising a quantity of hydrogel was used to inject the hydrogel plug 7 below the surface of the lung to a distance X through the hydrogel delivery needle 4. Then the hydrogel delivery needle 4 and 17 G coaxial cannula 2 were both advanced through the same hole and through the hydrogel plug 7 into the lung to a depth of 30 mm from the distal-most tip of the coaxial cannula 2. The lung tissue was then inserted into a water bath 84 at room temperature and the needle assembly was withdrawn from the lung tissue while under the surface of the water. The presence of bubbles was noted. The hydrogel seal was determined to have worked on cessation of bubbles coming from the lung. Results are presented in FIGS. 18B-18E as percent efficacy which is equivalent to: 100*((number of bubble free tests)/(total number of tests)). The following is a description of the results from these individual studies. 10 tests were conducted for each test variable and all tests were recorded for future analysis.

Figure 18B:
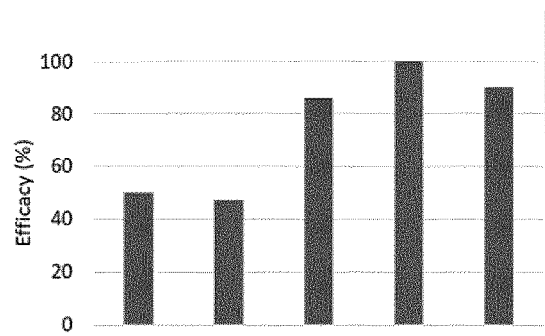

FIG. 18B presents the degree of efficacy with different hydrogel concentration (which can be related to gel viscosity and stiffness as presented later in FIG. 19 and FIG. 20). Hydrogels were created by mixing sodium hyaluronate powder with a molecular weight of 1.8-2 MDa with pure water at various concentrations; 20 mg/ml, 30 mg/ml, 40 mg/ml, 50 mg/ml, 60 mg/ml. The injection depth (2 mm below the surface of the lung), injection volume (500 µl) and injection rate (normal) were all kept constant while the efficacy of the variable concentrations were tested. The results found that at concentrations below 40 mg/ml, the hydrogel seal became less effective in preventing air from leaking from the lung.

Figure 18C:
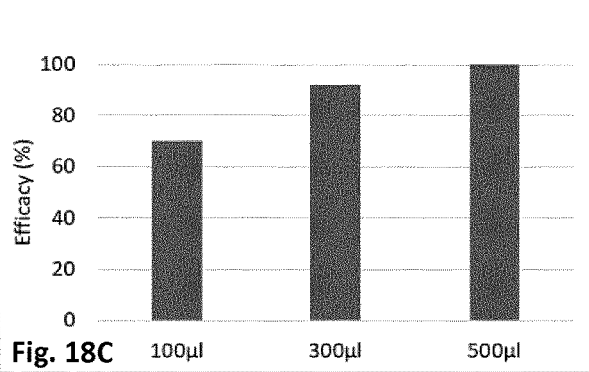

FIG. 18C presents the degree of efficacy with different injection volumes. The hydrogel concentration (60 mg/ml), injection depth (1 mm below the surface of the lung), and injection rate (normal) were all kept constant while the efficacy of variable volumes of hydrogel were tested. Results show a marked reduction in efficacy at a volume of 100 µl compared to 300 µl and 500 µl. Pilot studies were conducted with lower volumes 50 µl and were all ineffective at preventing air leak from the lung.

Figure 18D:
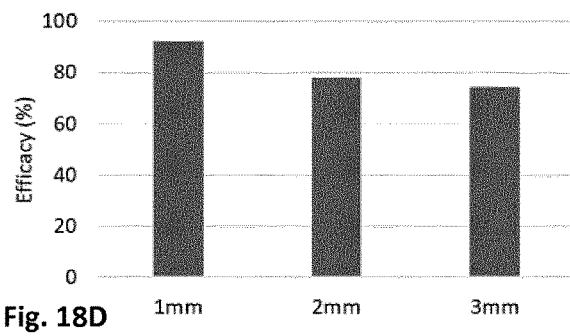

FIG. 18D presents the degree of efficacy with different injection depths. The gel volume (300 µl), gel concentration (60 mg/ml) and injection rate (normal) were all kept constant through this study while the efficacy of varying depths of injection of the hydrogel in the lung were tested. Results show that best results were achieved the closer the gel plug was to the periphery of the lung, up to the visceral pleura. Pilot tests were conducted at deeper injection depths ≥4 mm from the periphery of the lung with further reduced efficacy.

Figure 18E:
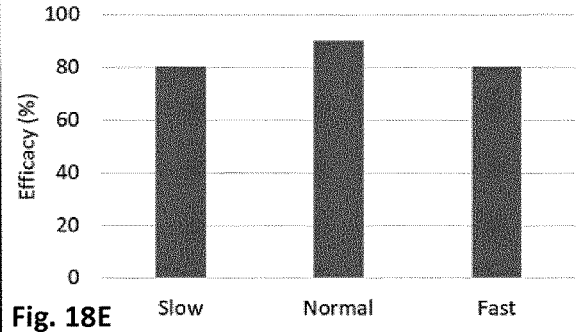

FIG. 18E presents the degree of efficacy of the hydrogel with different rates of injection into the lung. The hydrogel volume (500 µl), gel concentration (60 mg/ml) and gel depth (2 mm below the surface of the lung) were all kept constant during this study while the efficacy was tested for different rates of injection of the hydrogel. Approximate rates of injection were slow (6 secs) normal (3 secs), and fast (<1 sec). Based on the results which showed the best results at a normal injection rate, the relationship between injection rate and efficacy is unclear.

Figure 19:
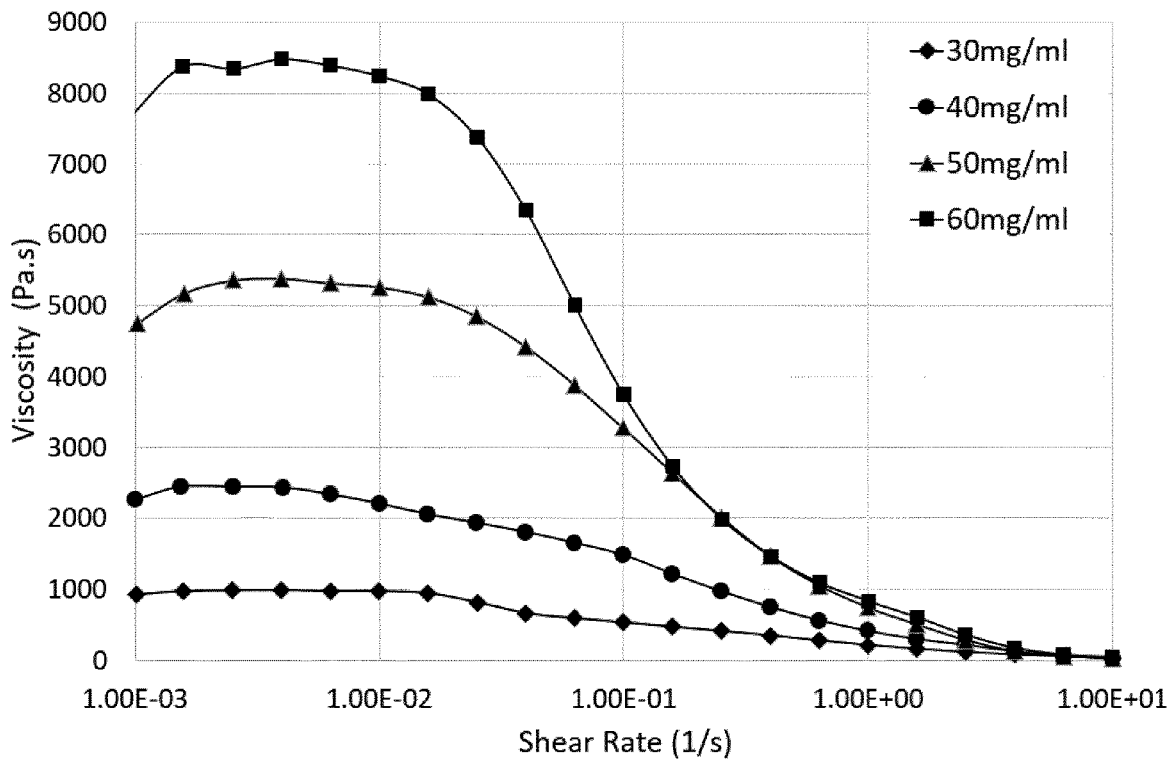
FIG. 19. Graph of viscosity vs. shear rate for hyaluronic acid hydrogels with varying concentration.

FIG. 19 presents viscosity data for gels used in the experiments outlined in FIGS. 18A-18E above. Hydrogels were created by mixing sodium hyaluronate powder with a molecular weight of 1.8-2 MDa with pure water at various concentration. Measurements of viscosity were made using a rheometer Model AR2000 by TA Instruments using a cone and plate geometry of 4 cm, cone-plate angle of 4°, a truncation gap of 112 µm and an analysis temperature of 25° C. Results show an increase in viscosity with increasing hydrogel concentration. The zero-shear rate viscosity for hyaluronic acid hydrogels ranged from approximately 1000 Pa·s for 30 mg/ml to approximately 8000 Pa·s for 60 mg/ml. (1 Pa·s=1000 cP). All gels display shear thinning properties at increased shear rates and all gels have a viscosity of <50 Pa·s at a shear rate of $10 \text{ s}^{-1}$.

Figure 20:
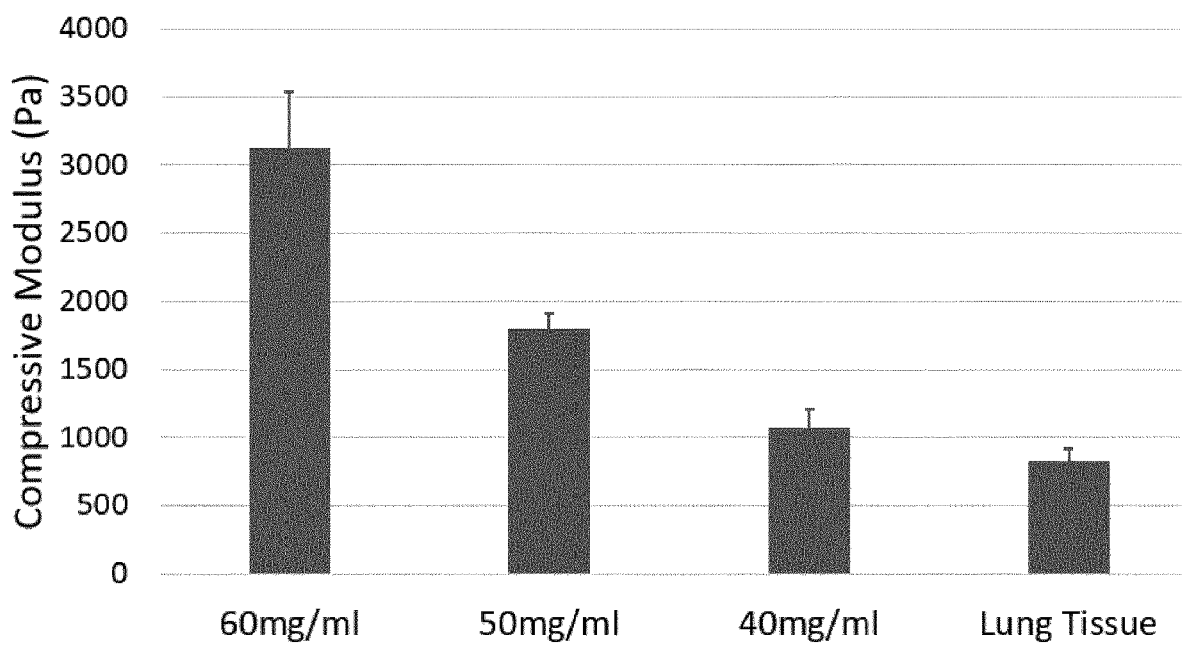
FIG. 20. Bar chart displaying the compressive modulus of hyaluronic acid hydrogels with varying concentration compared to lung tissue.

FIG. 20 presents results of compression testing to determine the stiffness of the hydrogels used in the injection studies presented in FIGS. 18A-18E. Hyaluronic acid hydrogels of increasing concentration were prepared as previously described. Hydrogels were formed into 5 mm thick sheet by pressing the hydrogels into a die and then using a core biopsy punch, 6 mm diameter cylinders with a height of 5 mm were created. To compare the results with lung tissue, equivalent cylindrical samples of lung parenchyma with a diameter of 6 mm and a height of 5 mm were excised from the lung parenchyma at the periphery of cadaveric porcine lungs. Compression tests of the cylindrical samples of hydrogel and lung tissue were performed using a Zwick universal testing machine with a 5N load cell at a strain rate of 3 mm/min. From the results it is evident that all gels have compressive stiffness greater than that of the lung parenchyma. Stiffness of lung tissue was found to be 825±95 Pa. Hydrogel stiffness varies from 1075±125 Pa for 40 mg/ml to 3125±403 Pa for 60 mg/ml. We found that hyaluronic acid hydrogels containing 30 mg/ml were unsuitable for forming cylindrical samples measuring 6 mm diameter therefore are not presented.

Figure 21A:
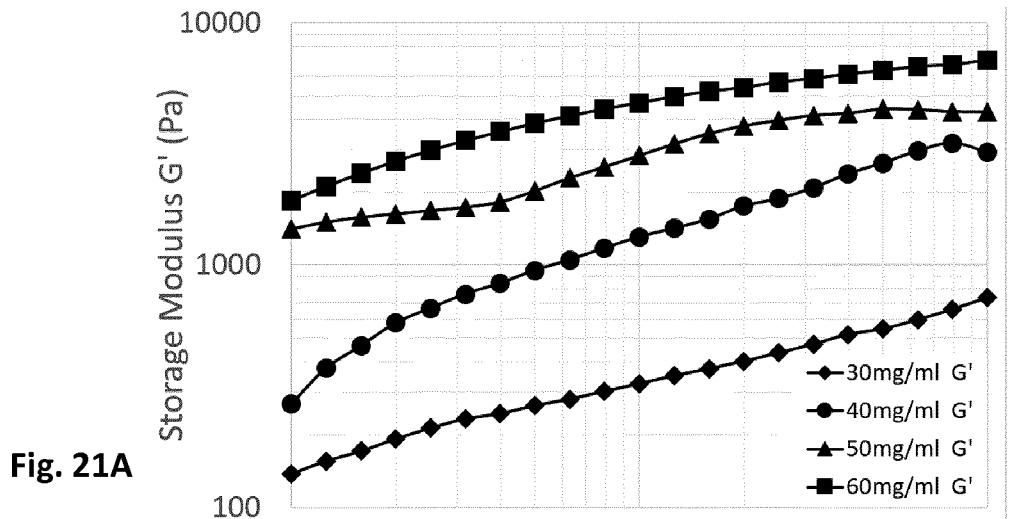
FIGS. 21A-21C. Series of graphs presenting the frequency dependant dynamic viscoelastic properties of hyaluronic acid hydrogels with varying concentration.
Figure 21B:
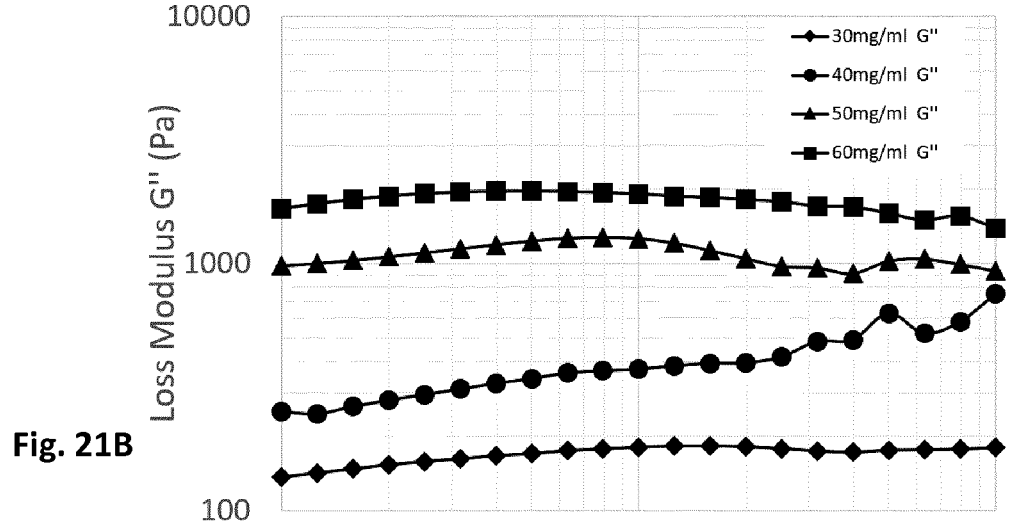
Figure 21C:
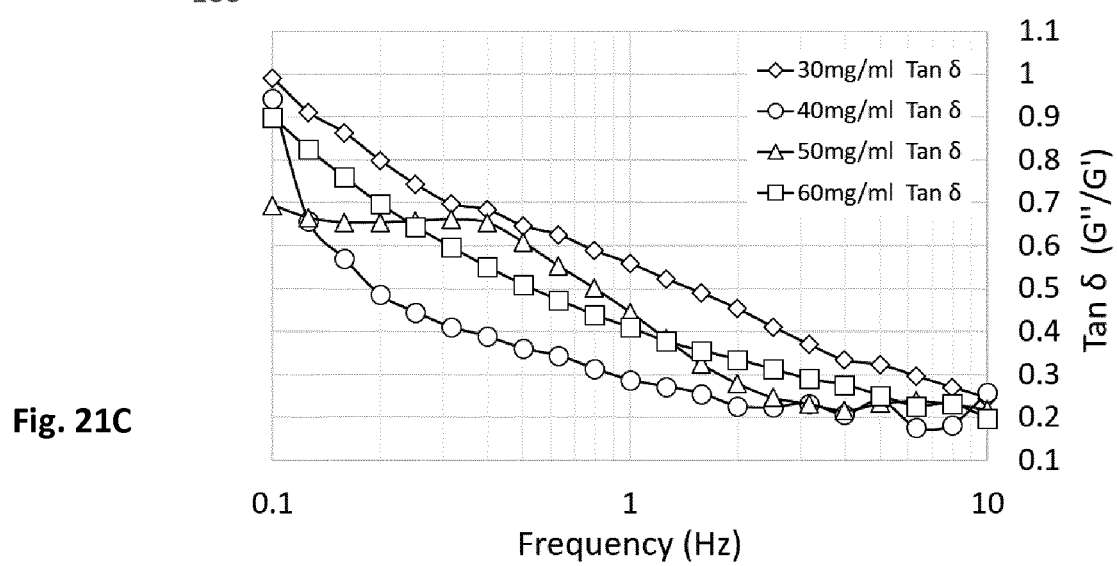

FIGS. 21A-21C presents viscoelastic properties of gels as measured using a dynamic oscillatory test method. The test rheometer used was a model AR2000 by TA Instruments. Dynamic oscillatory tests were conducted under stress control, with a 4 cm cone and plate geometry, a cone angle of 4°, a truncation gap of 112 µm, an analysis temperature of 25° C. and over a frequency range of 0.1-10 Hz. Gels were created by mixing sodium hyaluronate powder with a molecular weight of 1.8-2 MDa with pure water at various concentration; 20 mg/ml, 30 mg/ml, 40 mg/ml, 50 mg/ml, 60 mg/ml. In FIGS. 21A-21C, the dynamic viscoelasticity (storage modulus G', loss modulus G" tangent delta tan δ (G"/G') are presented over the frequency range 0.1-10 Hz. It is evident that G' and G" both increase with increasing gel concentration. For all gels, tan δ is within the range 0.2-0.6 at a frequency of 1 Hz. The lowest concentration gel, 30 mg/ml has the highest tan δ at 1 Hz of approximately 0.55. In a similar series of tests (results not presented), the analysis temperature was increased to 37° C. resulting in no or slight (<5%) variation in values to those presented here using an analysis temperature of 25° C.

Figure 22:
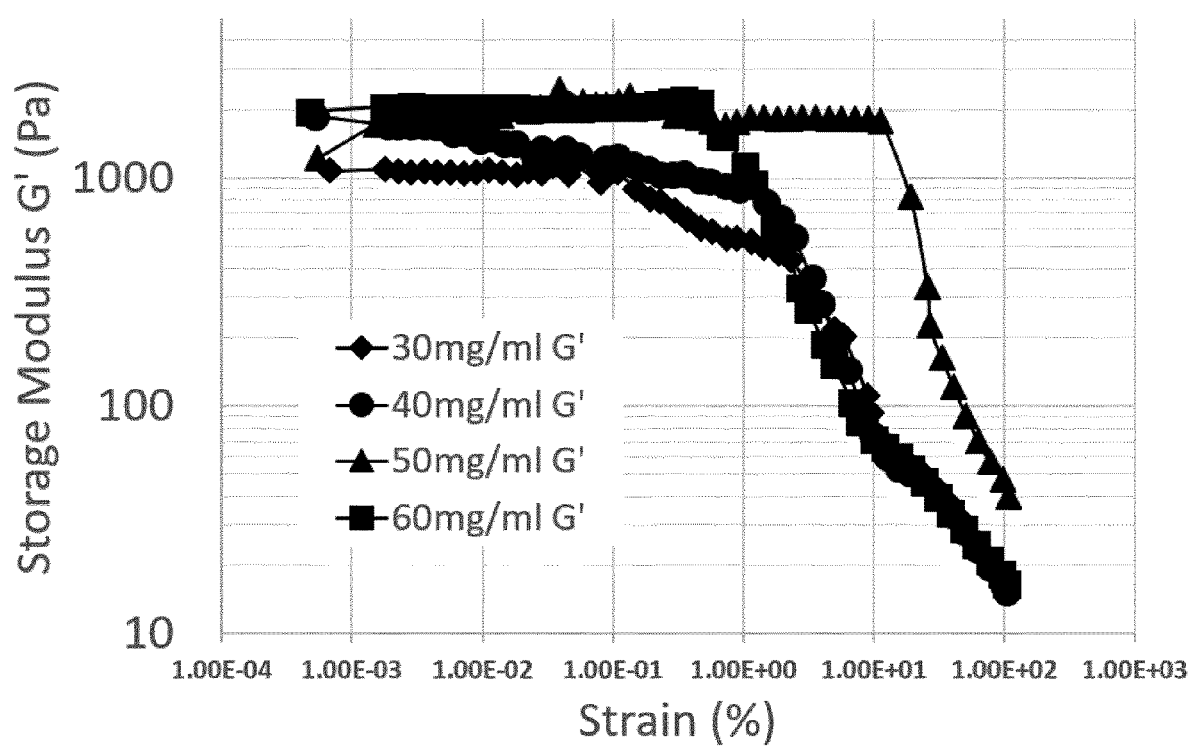
FIG. 22. Graph showing the strain dependant dynamic viscoelastic properties of hyaluronic acid hydrogels with varying concentration.

FIG. 22 shows the strain sweep data for hydrogels as measured using a dynamic oscillatory test. Tests were conducted under stress control, with a 4 cm cone and plate geometry, a cone angle of 4°, a truncation gap of 112 µm, an analysis temperature of 25° C., a frequency of 1 Hz and over a strain range of 0.001-100%. All hydrogels with concentration greater than 30 mg/ml appear relatively stable up to 1% strain. All gels exhibit shear thinning behaviour and all gels demonstrate a storage modulus G' of less than 100 Pa at 100% strain. In a similar series of tests (results not presented), the analysis temperature was increased to 37° C. resulting in no or slight (<5%) variation in values to those presented here using an analysis temperature of 25° C.

Figure 23A:
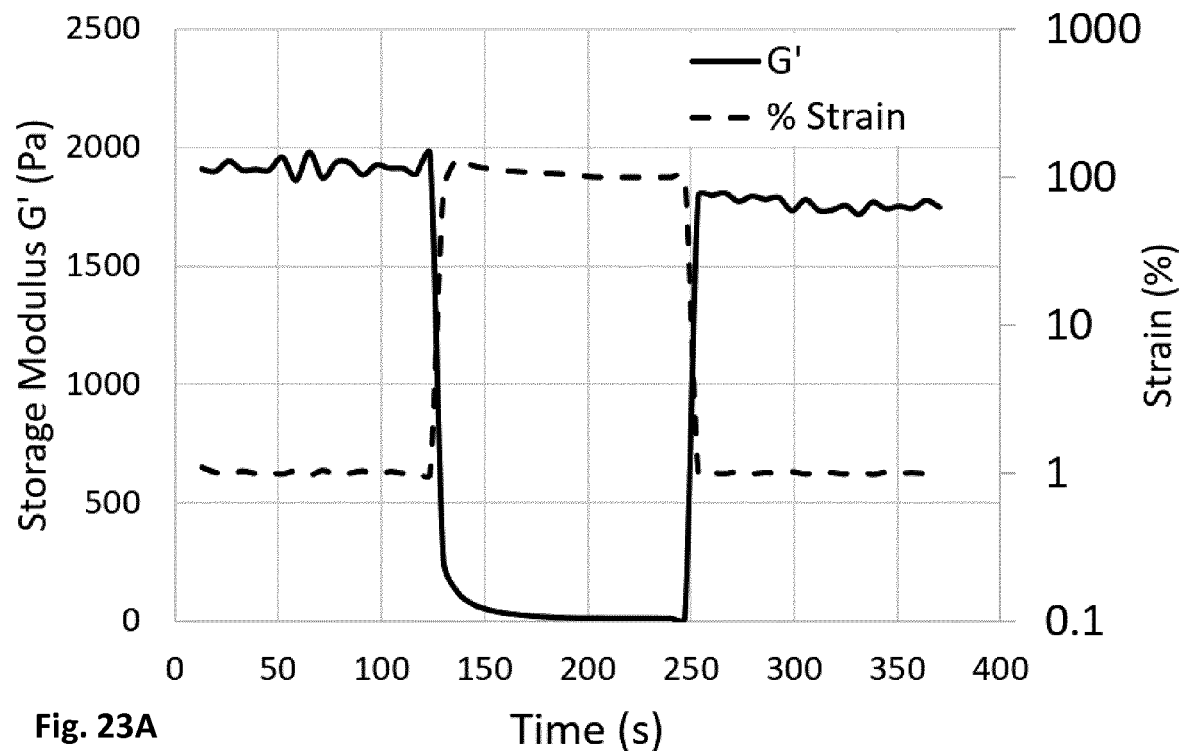
FIG. 23A-23B. Graph illustrating the dynamic viscoelastic properties of a 50 mg/ml hyaluronic acid hydrogel subjected to a stepped strain rate.
Figure 23B:
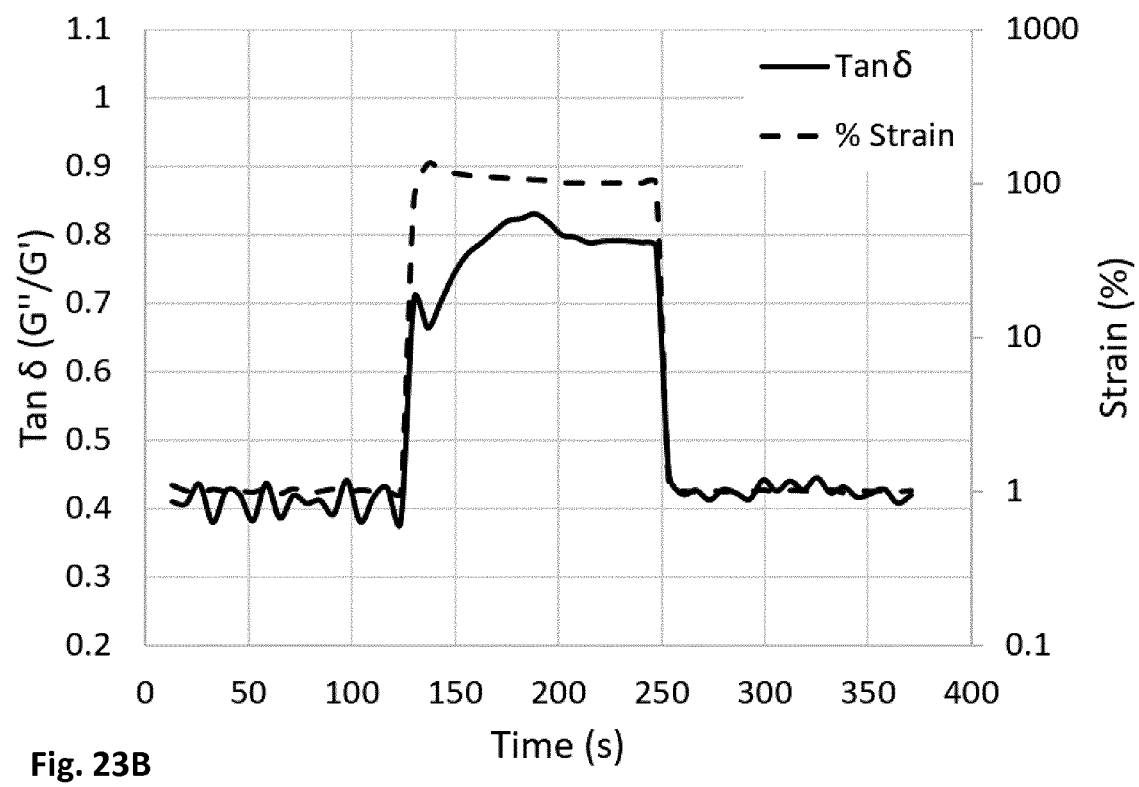

FIGS. 23A-23B shows a test demonstrating the shear thinning and recovery of the gels under cyclical shear stress. A stepped strain test was conducted with a 50 mg/ml HA hydrogel using a 4 cm cone and plate geometry, a cone angle of 4°, a truncation gap of 112 µm, an analysis temperature of 25° C., a frequency of 1 Hz and with a stepped strain rate from 1% to 100% to 1% with a delay of 6 seconds between different strain rates. There is a drop in G' from approx. 1900 Pa at 1% strain to approx. 20 Pa at 100% strain and an increase tan δ from approx. 0.4 at 1% strain to approx. 0.9 at 100% strain. This signifies a significant decrease in stiffness and viscosity with application of high shear strain. Interestingly, there is almost a full recovery in both the G' and tan δ when the strain rate is restored to 1%.

FIGS. 24A-24C presents an analysis of the hydrogel gel plug positioning and volumetric data gathered using a 3D-CAD model generated using SolidWorks®. The analysis presents the size and depth constraints related to delivering a gel plug below the surface of the lung. FIG. 24A shows an image of the 3D-CAD model representing the delivery of a viscous hydrogel plug 7 through an 18G delivery needle 4 the periphery of the lung, just below the lung visceral pleura surface G. The gel plug is injected through an outlet 6 in the delivery needle 4 so that it forms an annular spherical profile around the delivery needle 4. The injection depth of the hydrogel outlet 6 is presented as the distance of the outlet from the lung surface G and is indicated by X. For this analysis, the gel plug 7 is assumed to fill and expand outwards in an idealised radial fashion forming a spherical profile. The centre diameter of the plug is indicated by CØ. When the plug expands to abut the visceral pleura G, it forms a spherical segment that has a circular sealing profile at the visceral pleura G. The diameter of this sealing profile is indicated by SØ. FIG. 24B shows the relationship between the seal diameter at the surface of the lung at different injected volumes and depths. At a shallow injection depth of 1 mm below the surface of the lung, most gel material is present at the surface of the lung. For example, at an injection volume of 500 µl and at a depth of 1 mm, a plug seal of approx. 11.4 mm in diameter is achieved at the surface of the lung. Similarly, at an injection volume of 200 µl and a depth of 1 mm, a plug seal of approx. 8 mm in diameter is achieved at the surface of the lung. The deeper the injection, the less material is present at the surface of the lung, thereby reducing the efficacy of the seal. It is evident from the data that for an injection depth of 5 mm below the surface of the lung, a volume of above 500 µl is required to have any gel present at the surface of the lung. Similarly, for an injection depth of 4 mm, an injection volume above 300 µl is required to have any gel present at the surface of the lung. FIG. 24C presents data on the plug centre diameter at different injection depths and injected volumes. It is intuitive that higher injected volumes lead to higher gel plug diameters. At shallower depths, lower injected volumes are required to achieve an equivalent gel plug centre diameter. To achieve a 12 mm gel plug diameter 556 µl is required at an injection depth of 1 mm, whereas 873 µl is required to achieve an equivalent diameter at an injection depth of 5 mm. Lung tissue is comprised of aerated parenchyma with interconnected pathways to the periphery of the lung. Therefore, any area around the periphery of the lung that is not occluded or sealed may lead to a pneumothorax. The extent and size of the sealing plug is also relevant. Having additional material at the periphery of the lung will create a stronger seal against air leak.

FIG. 25A to FIG. 25C illustrate a method of performing a lung biopsy procedure using a system according to another embodiment of the invention, in which parts with reference to previous embodiments of the invention are assigned the same reference numerals. In this embodiment, the system comprises a coaxial delivery system for delivering a sealing plug of viscoelastic hydrogel that can be delivered either before or after a diagnostic or therapeutic procedure has been carried out. Referring to FIG. 25A, a coaxial cannula 2 is shown spanning the chest wall B and lung tissue D. The biopsy needle has been removed. The cannula 2 in this case has an aperture 2C, which can be comprised of a single aperture or multiple circumferential apertures, that is positioned proximal to it distal tip of the cannula 2. The aperture 2C may be designed in such a way so that it is visible under fluoroscopic guidance by removing a substantial portion of material about the cross-section of the tube about this point or by providing that cross-section of the tube with a radiopaque marker band comprising of high density material. The axial length of the aperture 2C may be approximately 0.3-2 mm. FIG. 25B shows a hydrogel delivery needle 4 inserted into the cannula 2 and adjusted so that the apertures 2C in the cannula are aligned with the hydrogel outlet 6 in the hydrogel delivery needle 4. The hydrogel delivery needle 4 may contain a male luer lock 4B or similar connector that engages with the female luer lock 2B of the coaxial cannula 2. A CT image of the lung is then taken to determine the distance between the aligned apertures and the pleural cavity E. The cannula 2 and needle 4 are then retracted together a distance so that the apertures are position just distal of the pleural cavity E in lung tissue (FIG. 25C). The syringe 15 is then actuated to inject the viscoelastic hydrogel into the lung, where it forms an annular sealing plug 7 around the cannula, within the lung tissue just distal of the pleural cavity E. The needle and cannula are then retracted, where the self-healing property of the hydrogel causes the annular plug to flow together and close, filling the needle tract just distal of the pleural cavity.

Figure 26A:
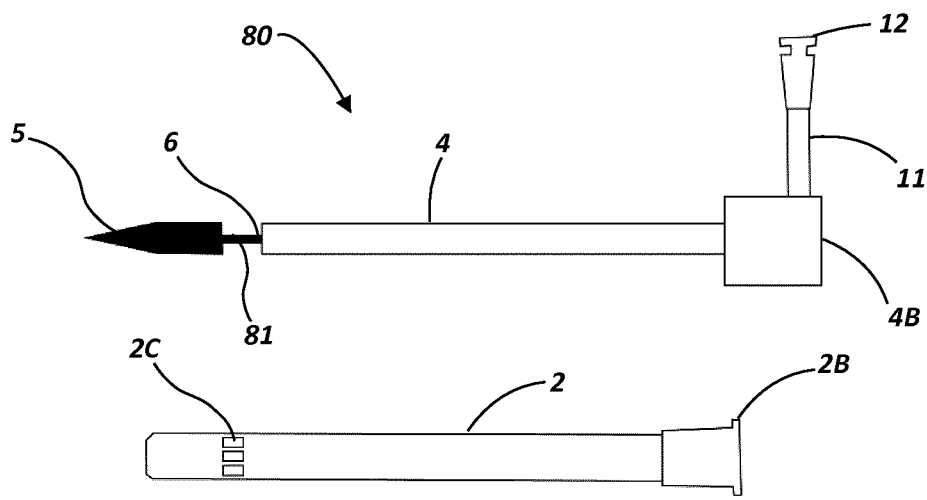
FIGS. 26A-26C. A series of lateral views illustrating an embodiment of the delivery device with a side aperture in the coaxial cannula.
Figure 26B:
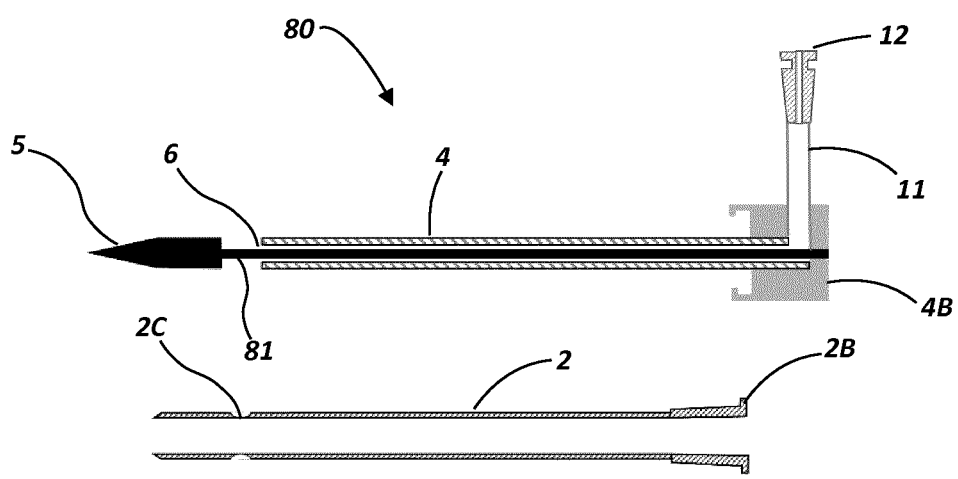
Figure 26C:
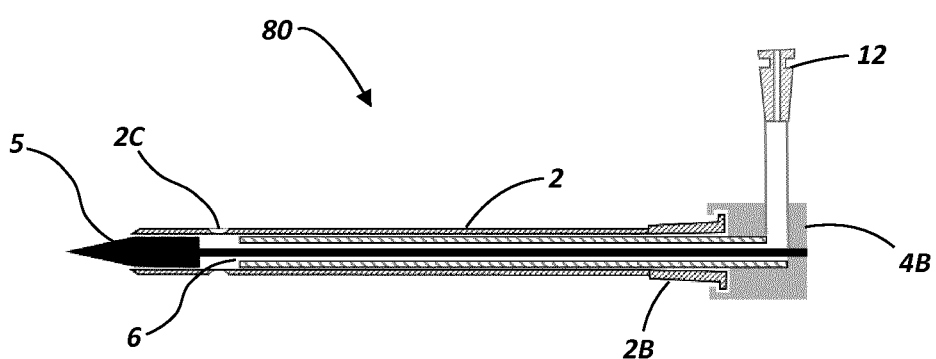

FIG. 26A to FIG. 26C illustrate a medical device according to an additional embodiment of the invention, indicated generally by the reference numeral 80, and in which parts identified with reference to the previous embodiments (including FIG. 25A to FIG. 25C) are assigned the same reference numerals. FIG. 26B shows the cross-sectional view of FIG. 26A. The medical device 80 comprises a cannula 2 that has a proximal hub 2B and an aperture 2C located proximal to the distal most tip of the cannula 2. The medical device 80 also comprises a delivery needle 4 with a hydrogel outlet 6 at its distal most tip. The delivery needle 4 is connected to a male luer lock 4B at its proximal end. A polymer tubing 11 fluidically connected to the delivery needle 4 via the male luer lock 4B terminates in a connector such as a luer lock 12 which is configured for attachment to a hydrogel delivery syringe. A central rod 81 connects to the male luer lock 4B and extends through the central lumen of the delivery needle 4 and beyond the distal end of the delivery needle 4 where it forms (or is bonded to) a piercing tip 5. The central rod 81 may be constructed from a material that is radiolucent to x-rays such as a stiff plastic or composite material. FIG. 26C presented in cross-section) shows the medical device whereby the delivery needle 4 is inserted through the cannula 2. The piercing tip 5 of the delivery needle assembly extends beyond the distal most tip of the cannula 2. The hydrogel outlet 6 of the delivery needle 4 lies proximal to the aperture 2C of the cannula 2. During a radiographically guided procedure (such as a CT guided procedure), this medical device configuration will provide the advantage of radiolucency about the aperture 2C and allow the clinician to position the aperture 2C for delivery of a sealing hydrogel plug. When a hydrogel material is injected, it will be extruded through the hydrogel outlet 6 and then through the aperture 2C. It will be prevented from passing through the tip of the cannula 2 by the fact that the piercing tip 5 predominately fills the internal lumen of the cannula 2.

Figure 27A:
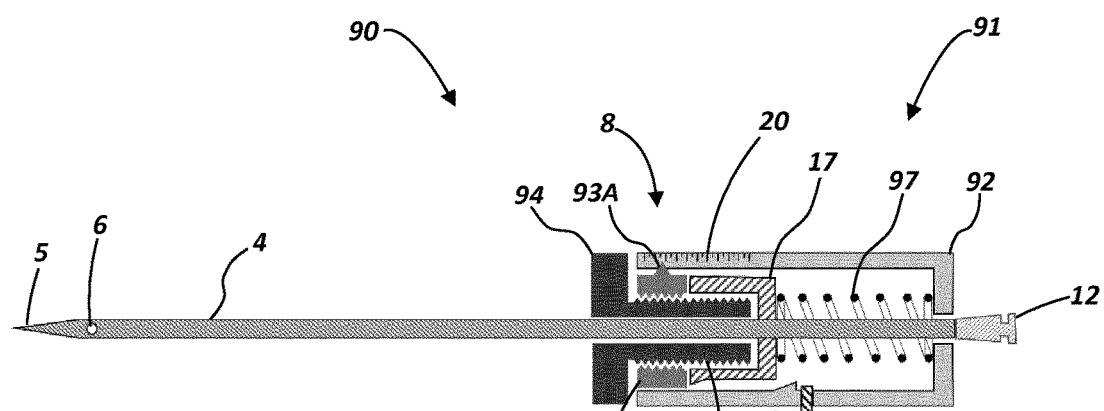
FIGS. 27A-27B. A series of lateral views illustrating an embodiment of the delivery device with a firing mechanism.
Figure 27B:
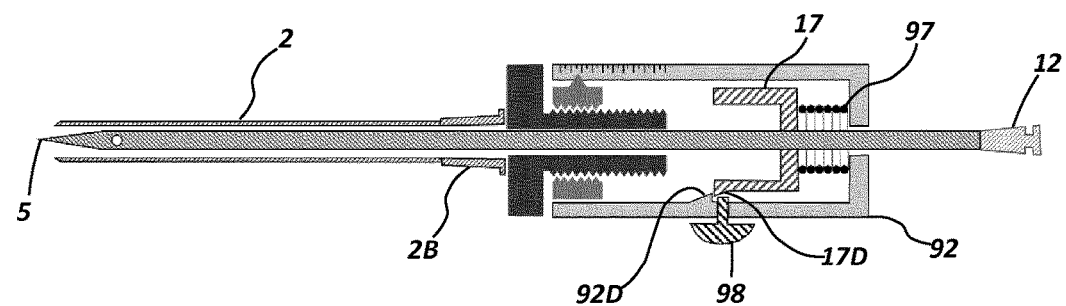

FIG. 27A and FIG. 27B illustrate a medical device according to an additional embodiment of the invention, indicated generally by the reference numeral 90, and in which parts identified with reference to the previous embodiments (including FIGS. 8A-8H) are assigned the same reference numerals. This embodiment is similar to the embodiment of FIGS. 8A-8H but additionally incorporates a firing mechanism 91 that is designed to advance the delivery needle tip 5 and side port 6 to a certain depth beyond the distal tip of the coaxial cannula 2. The advantage of providing a firing mechanism with the delivery needle is to avoid potential tenting of the organ membranes, for example the lung pleural membranes, when positioning the delivery side port 6 to below the surface of the lung or other organ. Tenting involves inward depression of the membranes and can potentially be caused by slow advancement of the delivery needle. Similar to the embodiments described in FIG. 8A-8H, the embodiment 90 provides a fixed housing 16 that is bonded to the delivery needle 4. The fixed housing 16 is free to move inside a handle 92 and the fixed housing 16 is kept in an advanced position by a compression spring 97 that is maintained in a compressed state between the proximal face of the fixed housing 16 and the internal proximal face of the handle 92. The compression spring 97 forces the fixed housing against a positioning mechanism 8 housed at the front of the handle 92 and incorporated into the handle 92. The positioning mechanism 8 is comprised of a leadscrew type mechanism that includes a front rotatable screw 94 with external thread 95 and engages with the internal thread of a movable carriage 93 with a depth indicator 93A. By rotating the screw 94, a user can move the position of the movable carriage 93 relative to a graduated scale 20 provided with the handle 92. This positioning mechanism 8 effectively provides the firing mechanism 91 with a variable depth setting to alter the distance that the needle tip and side port extend from the distal most face of the firing mechanism 91 (and coaxial cannula 2) when fired. As shown in FIG. 27B, to engage the firing mechanism 91 the delivery needle 4 is retracted by pulling on the luer lock 12 that is bonded to the delivery needle 4. When the delivery needle 4 is in the fully retracted position and the spring 97 fully compressed, an outward facing catch 17D on the movable hub 17 engages with an inward facing catch 92D on the handle 92 and prevents the forward motion of the delivery needle 4. In this configuration the needle is primed. FIG. 27B also shows the delivery needle 4 advanced through a coaxial cannula 2 so that the distal most face of the firing mechanism 91 abuts the proximal most face of the coaxial cannula luer lock 2B. In this configuration the needle tip 5 of the delivery needle should be either just at the distal most tip of the coaxial cannula 2 or proximal to the distal most tip of the coaxial cannula 2. To fire the needle forward, a button

98 is provided that when pushed will disengage the catches (92D, 17D) of the movable hub 17 from the handle 92.

Based on the results presented in both FIGS. 18A-18E and FIGS. 24A-24C the ideal depth of hydrogel delivery would be approximately 1 mm below the surface of the lung. However, for a number of reasons it may be difficult to target this depth using the delivery device described herein. FIG. 9 shows a CT scan of a measurement of distance P which is the distance from the distal-most tip of the coaxial cannula to the pleural cavity E. Errors in P measurement may be due to a shadow effect at the distal tip of the coaxial cannula. Errors may also be due to the CT scanner not scanning perpendicular to the axis of the coaxial cannula and scanning at an angle $\Theta$. In this instance P will be underestimated by the value. For these reasons a target depth greater than 1 mm is preferred. A target depth of 0.1-6 mm, preferably 1-4 mm is regarded as an appropriate target injection depth.

EXAMPLES

Example 1: A biphasic viscoelastic hydrogel comprising hyaluronic acid and crosslinked gelatin was created using the following method. Type A porcine derived gelatin (300Bloom) was dissolved fully in water at 7% w/v at 40° C. and allowed to set at 4° C. overnight. The resulting gel were subsequently freeze dried by freezing at −40° C. and drying at 25° C. under a constant vacuum of 0.1 mbar. The dried constructs were then heated under vacuum conditions (0.001 mbar) for 24 hours at 140° C. to induce crosslinking. The sponge was then roughly diced before being milled to form a fine powder using a cryo-mill (Model: 75 Spex SamplePrep, LLC.). The powder was sieved using a 125 μm sieve and the resultant powders had a powder particle size distribution of Dx10=7.4 μm, Dx50=32.8 μm, Dx90=95 μm as measured using a Mastersizer 3000 laser diffraction particle size analyser (Malvern Panalyticlal ltd). The dehydrothermally crosslinked gelatin powder was mixed with sodium hyaluronate powder (molecular weight: 1.8-2 MDa) and the powder mixture was hydrated with phosphate buffered saline solution at the following concentration: Gelatin: 130 mg/ml, Sodium hyaluronate:35 mg/ml. The resulting hydrogel was loaded into a syringe. The hydrogel was employed to prevent pneumothorax during a CT-guided transthoracic needle biopsy procedure as outlined in FIG. 8A-8F. This procedure was performed in a porcine model. The hydrogel formed an annular sealing plug around the needle during the biopsy procedure and after the needles were withdrawn, the hydrogel self-healed to prevent pneumothorax. The hydrogel persisted at the site for at least 1 week as was evidence from CT-scan follow-up.

Example 2: A biphasic viscoelastic hydrogel comprising hyaluronic acid and crosslinked gelatin was created using the following method. A type A porcine derived gelatin powder (300bloom) was ground to a fine powder using a cryo-mill (Model: 75 Spex SamplePrep, LLC.). The powder was sieved using a 125 μm sieve and the resultant powders had a powder particle size distribution of Dx10=5.4 μm, Dx50=35.5 μm, Dx90=90 μm as measured using a Mastersizer 3000 laser diffraction particle size analyser (Malvern Panalyticlal ltd). The resultant fine powder was heat treated under vacuum conditions (0.001 mbar) for 24 hours at 160° C. to induce crosslinking. The DHT crosslinked gelatin powder was mixed with sodium hyaluronate powder (molecular weight: 1.8-2 MDa) and the powder mixture was hydrated with phosphate buffered saline solution at the following concentration: Gelatin: 100 mg/ml, Sodium hyaluronate: 45 mg/ml. The resulting hydrogel was loaded into a syringe. The hydrogel was employed to prevent pneumothorax during a CT-guided transthoracic needle biopsy procedure similar to that outlined in FIG. 8A-8F. This procedure was performed in a porcine model. The hydrogel formed an annular sealing plug around the needle during the biopsy procedure and after the needles were withdrawn, the hydrogel self-healed to prevent pneumothorax.

Using the above method, various concentrations of the biphasic gel were evaluated rheologically and experimentally. The measurement of the dynamic viscoelasticity and dynamic viscosity of the hydrogels was made using a rheometer Model AR2000 manufactured by TA Instruments under the following conditions.

Method of measurement: oscillation test method, strain control
Measuring temperature: 25° C.
Geometry: 4° cone plate angle
Measuring geometry: 4 cm
Truncation gap: 112 μm
Frequency: 1 Hz

| Crosslinked Gelatin Concentration | Sodium Hyaluronate Concentration | Storage Modulus @ 1 Hz & 1% Strain | Tanδ @ 1 Hz & 1% Strain | Zero shear viscosity | Viscosity @ 100 s$^{-1}$ |
|---|---|---|---|---|---|
| 100 mg/ml | 45 mg/ml | 5,813 Pa | 0.4 | 18,367 Pa·s | 6.8 Pa·s |
| 150 mg/ml | 45 mg/ml | 11,667 Pa | 0.27 | 43,317 Pa·s | 10.0 Pa·s |
| 100 mg/ml | 35 mg/ml | 2,722 Pa | 0.45 | 6,700 Pa·s | 4.2 Pa·s |
| 150 mg/ml | 35 mg/ml | 6,406 Pa | 0.37 | 14,150 Pa·s | 5.9 Pa·s |

In a preferred embodiment, the viscoelastic hydrogel is capable of preventing pneumothorax during procedures requiring transthoracic needle access by being injected just below the visceral pleura of the lung and by having the following properties:

1. The hydrogel has low enough viscosity under shear stress exerted by the syringe to enable the hydrogel to be injected to the target site through a needle, catheter or other luminal device.

2. Once exiting the needle the hydrogel undergoes a rapid thixotropic recovery to a stiffness sufficient to prevent infiltration of lung tissue.

3. Once the needle has been removed, an element of viscous flow enables the gel to flow back to form a single entity. The gel flows back to fill the void left by the needle in the lung tissue and in the visceral pleura. It may achieve this by having a sufficient flowable nature which is preferably dependent on having a high tan δ.

4. The gel has sufficient rigidity and storage modulus (G') that it is not prematurely ejected from the lung and remains at the delivery site until healing has occurred.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A system for sealing a channel in lung tissue created during a minimally invasive percutaneous procedure, comprising:
a medical device comprising a hydrogel delivery needle with a hydrogel outlet, and a coaxial cannula having an inner lumen configured for receipt of the hydrogel delivery needle, and
an injectable hydrogel provided in a syringe configured for fluidic connection to a proximal end of the hydrogel delivery needle,
wherein the injectable hydrogel is a viscoelastic shear-thinning hydrogel configured to exhibit sufficient stiffness after needle delivery to avoid lung tissue infiltration and push lung tissue away from the delivery needle,
in which the injectable viscoelastic shear-thinning hydrogel exhibits a storage modulus (G') of at least 400 Pa in dynamic viscoelasticity measured by a rheometer at 1 Hz and 1% strain rate at 25° C.,
in which the injectable viscoelastic shear-thinning hydrogel comprises a crosslinked polymer.

2. A system according to claim 1, in which the injectable viscoelastic shear-thinning hydrogel exhibits a tan δ (G"/G') from 0.1 to 0.8 in dynamic viscoelasticity measured by a rheometer at 1 Hz and 1% strain rate at 25° C.

3. A system according to claim 1, in which the injectable viscoelastic shear-thinning hydrogel exhibits a compressive modulus of greater than that of lung tissue.

4. A system according to claim 1, in which the shear-thinning viscoelastic hydrogel is configured to exhibit an in-vivo residence time of at least 1 week.

5. A system according to claim 1, in which the hydrogel outlet is disposed on a side of the hydrogel delivery needle proximal to the tip.

6. A system according to claim 1, in which the viscoelastic hydrogel comprises a continuous phase comprising continuous phase polymer and a dispersed phase comprising micron-sized insoluble polymer particles.

7. A system according to claim 1, in which the viscoelastic hydrogel comprises a continuous phase comprising continuous phase polymer and a dispersed phase comprising micron-sized insoluble polymer particles, and in which the micron-sized insoluble polymer particles have an average dimension of less than 100 microns.

8. A system according to claim 1, in which the viscoelastic hydrogel comprises a continuous phase comprising continuous phase polymer and a dispersed phase comprising micron-sized insoluble polymer particles, in which the continuous phase polymer comprises hyaluronic acid (HA) or a salt thereof.

9. A system according to claim 1, in which the viscoelastic hydrogel comprises a continuous phase comprising continuous phase polymer and a dispersed phase comprising micron-sized insoluble polymer particles, and in which the micron-sized insoluble polymer particles are formed of crosslinked gelatin.

10. A system according to claim 1, in which the viscoelastic hydrogel comprises a continuous phase comprising continuous phase polymer and a dispersed phase comprising micron-sized insoluble polymer particles, and in which the viscoelastic hydrogel comprises 2-20% micron-sized insoluble polymer particles (w/v).

11. A system according to claim 1, in which the hydrogel delivery needle comprises a piercing tip.

12. A system according to claim 1, in which the viscoelastic hydrogel comprises a continuous phase comprising continuous phase polymer and a dispersed phase comprising micron-sized insoluble polymer particles, in which the continuous phase polymer comprises hyaluronic acid (HA) or a salt thereof, and in which the HA or salt thereof is not crosslinked and the micron-sized insoluble polymer particles are dehydrothermally crosslinked.

13. A system according to claim 1, in which the viscoelastic hydrogel comprises a continuous phase comprising continuous phase polymer and a dispersed phase comprising micron-sized insoluble polymer particles, in which micron-sized insoluble polymer particles are crosslinked gelatin particles.

14. A system according to claim 1, in which the system further comprises a syringe configured for fluidic connection to the hydrogel delivery needle, and in which the viscoelastic hydrogel is provided in the syringe.

15. A system according to claim 1, which further comprises an adjustable positioning mechanism configured to limit the advancement depth of the hydrogel delivery needle through the coaxial cannula as indicated by a measurement scale forming part of the medical device, in which the adjustable positioning mechanism comprises a fixed housing attached to the hydrogel delivery needle, a movable hub mounted to the needle for axial movement along the hydrogel delivery needle relative to the fixed housing and having a distal-most face configured to abut a proximal face of the coaxial cannula luer lock.

16. A system according to claim 1, which further comprises an adjustable positioning mechanism configured to limit the advancement depth of the hydrogel delivery needle through the coaxial cannula as indicated by a measurement scale forming part of the medical device, in which the measurement scale-is provided with the adjustable positioning mechanism and is configured to indicate an injection depth P of the hydrogel outlet and whereby the hydrogel outlet is positioned a distance P+X distal to the distal-most tip of the coaxial cannula when the distal-most face-of the adjustable positioning mechanism fully abuts the proximal face of the coaxial cannula.

17. A system according to claim 1, in which the system further comprises a core needle with penetrating distal tip configured for insertion through the inner lumen of the coaxial cannula and attachment to the coaxial cannula luer lock.

18. A system according to claim 1, in which the hydrogel delivery needle includes a radiopaque or radiolucent marker in which the radiopaque or radiolucent marker is optionally disposed distal to the hydrogel outlet.

* * * * *